(12) United States Patent
Israel et al.

(10) Patent No.: US 6,593,109 B1
(45) Date of Patent: Jul. 15, 2003

(54) RECOMBINANT BONE MORPHOGENETIC PROTEIN HETERODIMERS, COMPOSITIONS AND METHODS OF USE

(75) Inventors: David Israel, Concord, MA (US); Neil M. Wolfman, Dover, MA (US)

(73) Assignee: Genetics Institute, Inc., Cambridge, MA (US)

(*) Notice: Subject to any disclaimer, the term of this patent is extended or adjusted under 35 U.S.C. 154(b) by 150 days.

(21) Appl. No.: 09/780,601

(22) Filed: Feb. 9, 2001

Related U.S. Application Data

(60) Division of application No. 08/469,411, filed on Jun. 6, 1995, now Pat. No. 6,190,880, which is a continuation-in-part of application No. 07/864,692, filed on Apr. 7, 1992, now abandoned, which is a continuation-in-part of application No. 07/787,496, filed on Nov. 4, 1991, now abandoned.

(30) Foreign Application Priority Data

Nov. 2, 1992 (WO) .............................. PCT/US92/09430

(51) Int. Cl.[7] .......................... C12N 15/18; C12N 5/10; C12N 5/12; C07K 14/51

(52) U.S. Cl. .............. 435/69.1; 435/252.3; 435/252.33; 435/255.1; 435/320.1; 435/325; 435/70.2; 530/350; 530/399; 536/23.5

(58) Field of Search .......................... 435/69.1, 252.3, 435/252.33, 255.1, 320.1, 325, 70.2, 69.4, 172.3, 255.2; 530/350, 399; 536/23.5, 23.51

(56) References Cited

U.S. PATENT DOCUMENTS

| | | | |
|---|---|---|---|
| 4,294,753 A | 10/1981 | Urist | |
| 4,434,094 A | 2/1984 | Seyedin et al. | |
| 4,455,256 A | 6/1984 | Urist | |
| 4,563,350 A | 1/1986 | Nathan | |
| 4,608,199 A | 8/1986 | Caplan et al. | |
| 4,627,982 A | 12/1986 | Seyedin et al. | |
| 4,681,763 A | 7/1987 | Nathanson | |
| 4,737,578 A | 4/1988 | Evans | |
| 4,761,471 A | 8/1988 | Urist | |
| 4,769,328 A | 9/1988 | Murray et al. | |
| 4,774,228 A | 9/1988 | Seyedin | |
| 4,774,322 A | 9/1988 | Seyedin | |
| 4,789,732 A | 12/1988 | Urist | |
| 4,798,885 A | 1/1989 | Mason | |
| 4,804,744 A | 2/1989 | Sen | |
| 4,810,691 A | 3/1989 | Seyedin | |
| 4,843,063 A | 6/1989 | Seyedin | |
| 4,886,747 A | 12/1989 | Derynck | |
| 4,908,204 A | 3/1990 | Robinson et al. | |
| 4,968,590 A | 11/1990 | Kuberasampath et al. | |
| 4,992,274 A | 2/1991 | Robinson et al. | |
| 5,011,691 A | 4/1991 | Oppermann | |
| 5,106,626 A | 4/1992 | Parsons et al. | |
| 5,106,748 A | 4/1992 | Wozney et al. | |
| 5,108,753 A | 4/1992 | Kuberasampath | |
| 5,141,905 A | 8/1992 | Rosen et al. | |
| 5,166,058 A | 11/1992 | Wang et al. | |
| 5,187,076 A | 2/1993 | Wozney et al. | |
| 5,187,263 A | 2/1993 | Murray et al. | |
| 5,208,219 A | 5/1993 | Ogawa et al. | |
| 5,258,494 A | 11/1993 | Oppermann | |
| 5,266,683 A | 11/1993 | Oppermann et al. | |
| 5,284,756 A | 2/1994 | Grinna et al. | |
| 5,399,346 A | 3/1995 | Anderson et al. | |

FOREIGN PATENT DOCUMENTS

| | | |
|---|---|---|
| CA | 2 017466 | 5/1990 |
| EP | 33 6760 A2 | 6/1989 |
| EP | 4 165 78 A2 | 5/1990 |
| EP | 4 094 72 A1 | 11/1990 |
| EP | 433225 | 6/1991 |
| EP | 0 626 451 A2 | 5/1994 |
| WO | WO 89/10409 | 2/1989 |
| WO | WO 89/09787 | 10/1989 |
| WO | WO 89/09788 | 10/1989 |
| WO | WO 90/03733 | 4/1990 |
| WO | WO 90/11366 | 10/1990 |
| WO | WO 91/02744 | 3/1991 |
| WO | WO 91/05802 | 5/1991 |
| WO | WO 93/00049 | 7/1991 |
| WO | WO 91/18047 | 11/1991 |
| WO | WO 91/18098 | 11/1991 |

OTHER PUBLICATIONS

Urist et al., *Science* 220:680–686 (1983).
Luyten et al., *The Journal of Biological Chemistry* 264(23):13377–13380 (Aug. 15, 1989).
Sampath, et al., *Proc. Natl Acad. Sci* 84:7109–7113 (1987).
Ozkaynak et al., *The EMBO Journal* v.9 No. 7:2085–2093 (1990).
Lyons et al., *Proc. Natl. Acad. Sci (USA)* 86:4554–4558 (Jun. 1989).
Hammonds et al., *Molecular Endocrinology* 5:149–155 (1991).
Celeste et al., *Proc. Natl. Acad. Sci (USA)* 87:9843–9847 (Dec. 1990).
Sampath et al., *J. Biological Chemistry* 265:13198–13205 (1990).
Wang et al., *Proc. Natl. Acad. Sci (USA)* 87:2220–2224 (Mar. 1990).
Wang et al., *J. Cell Biochem. Suppl. 15 Part E*:161 Abstract (1991).
Wozney, *Prog. Growth Factor Res.* 1(4):267–280 (1989).
Wozney et al., *J. of Cell Biochem Suppl. 16F*:76 Abstract (1992).

*Primary Examiner*—Gary Kunz
*Assistant Examiner*—Stephen Gucker
(74) *Attorney, Agent, or Firm*—Finnegan, Henderson, Farabow, Garrett, and Dunner, LLP

(57) ABSTRACT

The present invention relates to a methods for producing recombinant heterodimeric BMP proteins useful in the field of treating bone defects, healing bone injury and in wound healing in general. The invention also relates to the recombinant heterodimers and compositions containing them.

15 Claims, 30 Drawing Sheets

```
            10         20         30         40         50         60         70
     GTCGACTCTA GAGTGTGTGT CAGCACTTGG CTGGGGACTT CTTGAACTTG CAGGGAGAAT AACTTGCGCA 80         90        100        110        120        130        140
     CCCCACTTTG CGCCGGTGCC TTTGCCCCAG CGGAGCCTGC TTCGCCATCT CCGAGCCCCA CCGCCCCTCC 150        160        170        180        190        200        210
     ACTCCTCGGC CTTGCCCGAC ACTGAGACGC TGTTCCCAGC GTGAAAAGAG AGACTGCGCG GCCGGCACCC 220        230        240        250        260        270        280
     GGGAGAAGGA GGAGGCAAAG AAAAGGAACG GACATTCGGT CCTTGCGCCA GGTCCTTTGA CCAGAGTTTT 290        300        310        320        330        340        350
     TCCATGTGGA CGCTCTTTCA ATGGACGTGT CCCCGCGTGC TTCTTAGACG GACTGCGGTC TCCTAAAGGT (1)              370              385              400
     CGACC ATG GTG GCC GGG ACC CGC TGT CTT CTA GCG TTG CTG CTT CCC CAG GTC
           MET Val Ala Gly Thr Arg Cys Leu Leu Ala Leu Leu Leu Pro Gln Val 415              430              445
     CTC CTG GGC GGC GCG GCT GGC CTC GTT CCG GAG CTG GGC CGC AGG AAG TTC GCG
     Leu Leu Gly Gly Ala Ala Gly Leu Val Pro Glu Leu Gly Arg Arg Lys Phe Ala
                                            (24)
     460              475              490              505
     GCG GCG TCG TCG GGC CGC CCC TCA TCC CAG CCC TCT GAC GAG GTC CTG AGC GAG
     Ala Ala Ser Ser Gly Arg Pro Ser Ser Gln Pro Ser Asp Glu Val Leu Ser Glu 520              535              550              565
     TTC GAG TTG CGG CTG CTC AGC ATG TTC GGC CTG AAA CAG AGA CCC ACC CCC AGC
     Phe Glu Leu Arg Leu Leu Ser MET Phe Gly Leu Lys Gln Arg Pro Thr Pro Ser 580              595              610
     AGG GAC GCC GTG GTG CCC CCC TAC ATG CTA GAC CTG TAT CGC AGG CAC TCA GGT
     Arg Asp Ala Val Val Pro Pro Tyr MET Leu Asp Leu Tyr Arg Arg His Ser Gly 625              640              655              670
     CAG CCG GGC TCA CCC GCC CCA GAC CAC CGG TTG GAG AGG GCA GCC AGC CGA GCC
     Gln Pro Gly Ser Pro Ala Pro Asp His Arg Leu Glu Arg Ala Ala Ser Arg Ala
```

FIG. 1

```
                685                    700                    715
AAC ACT GTG CGC AGC TTC CAC CAT GAA GAA TCT TTG GAA GAA CTA CCA GAA ACG
Asn Thr Val Arg Ser Phe His His Glu Glu Ser Leu Glu Glu Leu Pro Glu Thr 730                    745                    760                    775
AGT GGG AAA ACA ACC CGG AGA TTC TTC TTT AAT TTA AGT TCT ATC CCC ACG GAG
Ser Gly Lys Thr Thr Arg Arg Phe Phe Phe Asn Leu Ser Ser Ile Pro Thr Glu 790                    805                    820                835
GAG TTT ATC ACC TCA GCA GAG CTT CAG GTT TTC CGA GAA CAG ATG CAA GAT GCT
Glu Phe Ile Thr Ser Ala Glu Leu Gln Val Phe Arg Glu Gln MET Gln Asp Ala 850                    865                    880
TTA GGA AAC AAT AGC AGT TTC CAT CAC CGA ATT AAT ATT TAT GAA ATC ATA AAA
Leu Gly Asn Asn Ser Ser Phe His His Arg Ile Asn Ile Tyr Glu Ile Ile Lys 895                    910                    925                    940
CCT GCA ACA GCC AAC TCG AAA TTC CCC GTG ACC AGA CTT TTG GAC ACC AGG TTG
Pro Ala Thr Ala Asn Ser Lys Phe Pro Val Thr Arg Leu Leu Asp Thr Arg Leu 995                    970                    985
GTG AAT CAG AAT GCA AGC AGG TGG GAA AGT TTT GAT GTC ACC CCC GCT GTG ATG
Val Asn Gln Asn Ala Ser Arg Trp Glu Ser Phe Asp Val Thr Pro Ala Val MET 1000                   1015                   1030                   1045
CGG TGG ACT GCA CAG GGA CAC GCC AAC CAT GGA TTC GTG GTG GAA GTG GCC CAC
Arg Trp Thr Ala Gln Gly His Ala Asn His Gly Phe Val Val Glu Val Ala His 1060                   1075                   1090                   1105
TTG GAG GAG AAA CAA GGT GTC TCC AAG AGA CAT GTT AGG ATA AGC AGG TCT TTG
Leu Glu Glu Lys Gln Gly Val Ser Lys Arg His Val Arg Ile Ser Arg Ser Leu
                                                                    (249)
CAC CAA GAT GAA CAC AGC TGG TCA CAG ATA AGG CCA TTG CTA GTA ACT TTT GGC
His Gln Asp Glu His Ser Trp Ser Gln Ile Arg Pro Leu Leu Val Thr Phe Gly
                                                                    (266)
    1165                   1180                   1195                   1210
CAT GAT GGA AAA GGG CAT CCT CTC CAC AAA AGA GAA AAA CGT CAA GCC AAA CAC
His Asp Gly Lys Gly His Pro Leu His lys Arg Glu Lys Arg Gln Ala Lys His
                                                                    (283)
        1225                   1240                   1255
AAA CAG CGG AAA CGC CTT AAG TCC AGC TGT AAG AGA CAC CCT TTG TAC GTG GAC
Lys Gln Arg Lys Arg Leu Lys Ser Ser Cys Lys Arg His Pro Leu Tyr Val Asp
                                    (296)
1270                   1285                   1300                   1315
TTC AGT GAC GTG GGG TGG AAT GAC TGG ATT GTG GCT CCC CCG GGG TAT CAC GCC
Phe Ser Asp Val Gly Trp Asn Asp Trp Ile Val Ala Pro Pro Gly Tyr His Ala
```

FIG. 1 (CON'T)

```
        1330                    1345                    1360                    1375
TTT TAC TGC CAC GGA GAA TGC CCT TTT CCT CTG GCT GAT CAT CTG AAC TCC ACT
Phe Tyr Cys His Gly Glu Cys Pro Phe Pro Leu Ala Asp His Leu Asn Ser Thr 1390                    1405                    1420
AAT CAT GCC ATT GTT CAG ACG TTG GTC AAC TCT GTT AAC TCT AAG ATT CCT AAG
Asn His Ala Ile Val Gln Thr Leu Val Asn Ser Val Asn Ser Lys Ile Pro Lys 1435                    1450                    1465                    1480
GCA TGC TGT GTC CCG ACA GAA CTC AGT GCT ATC TCG ATG CTG TAC CTT GAC GAG
Ala Cys Cys Val Pro Thr Glu Leu Ser Ala Ile Ser MET Leu Tyr Leu Asp Glu 1495                    1510                    1525
AAT GAA AAG GTT GTA TTA AAG AAC TAT CAG GAC ATG GTT GTG GAG GGT TGT GGG
Asn Glu Lys Val Val Leu Lys Asn Tyr Gln Asp MET Val Val Glu Gly Cys Gly

1540(396)    1553       1563       1573       1583       1593       1603
TGT CGC TAGTACAGCA AAATTAAATA CATAAATATA TATATATATA TATATTTTAG AAAAAAGAAA
Cys Arg

AAAA
```

FIG. 1 (CON'T)

```
         10         20         30         40         50         60         70
CTCTAGAGGG CAGAGGAGGA GGGAGGGAGG GAAGGAGCGC GGAGCCCGGC CCGGAAGCTA GGTGAGTGTG 80         90        100        110        120        130        140
GCATCCGAGC TGAGGGACGC GAGCCTGAGA CGCCGCTGCT GCTCCGGCTG AGTATCTAGC TTGTCTCCCC 150        160        170        180        190        200        210
GATGGGATTC CCGTCCAAGC TATCTCGAGC CTGCAGCGCC ACAGTCCCCG GCCCTCGCCC AGGTTCACTG 220        230        240        250        260        270        280
CAACCGTTCA GAGGTCCCCA GGAGCTGCTG CTGGCGAGCC CGCTACTGCA GGGACCTATG GAGCCATTCC 290        300        310        320        330        340        350
GTAGTGCCAT CCCGAGCAAC GCACTGCTGC AGCTTCCCTG AGCCTTTCCA GCAAGTTTGT TCAAGATTGG 360        370        380        390        400        (1)
CTGTCAAGAA TCATGGACTG TTATTATATG CCTTGTTTTC TGTCAAGACA CC ATG ATT CCT
                                                          MET Ile Pro
       417                 432                 447                 462
GGT AAC CGA ATG CTG ATG GTC GTT TTA TTA TGC CAA GTC CTG CTA GGA GGC GCG
Gly Asn Arg MET Leu Met Val Val Leu Leu Cys Gln Val Leu Leu Gly Gly Ala 477                 492                 507
AGC CAT GCT AGT TTG ATA CCT GAG ACG GGG AAG AAA AAA GTC GCC GAG ATT CAG
Ser His Ala Ser Leu Ile Pro Glu Thr Gly Lys Lys Lys Val Ala Glu Ile Gln 522                 537                 552                 567
GGC CAC GCG GGA GGA CGC CGC TCA GGG CAG AGC CAT GAG CTC CTG CGG GAC TTC
Gly His Ala Gly Gly Arg Arg Ser Gly Gln Ser His Glu Leu Leu Arg Asp Phe 582                 597                 612                 627
GAG GCG ACA CTT CTG CAG ATG TTT GGG CTG CGC CGC CGC CCG CAG CCT AGC AAG
Glu Ala Thr Leu Leu Gln MET Phe Gly Leu Arg Arg Arg Pro Gln Pro Ser Lys 642                 657                 672
AGT GCC GTC ATT CCG GAC TAC ATG CGG GAT CTT TAC CGG CTT CAG TCT GGG GAG
Ser Ala Val Ile Pro Asp Tyr MET Arg Asp Leu Tyr Arg Leu Gln Ser Gly Glu
```

FIG. 2

```
      687                    702                    717                    732
GAG GAG GAA GAG CAG ATC CAC AGC ACT GGT CTT GAG TAT CCT GAG CGC CCG GCC
Glu Glu Glu Glu Gln Ile His Ser Thr Gly Leu Glu Tyr Pro Glu Arg Pro Ala 747                    762                    777
AGC CGG GCC AAC ACC GTG AGG AGC TTC CAC CAC GAA GAA CAT CTG GAG AAC ATC
Ser Arg Ala Asn Thr Val Arg Ser Phe His His Glu Glu His Leu Glu Asn Ile 792                    807                    822                    837
CCA GGG ACC AGT GAA AAC TCT GCT TTT CGT TTC CTC TTT AAC CTC AGC AGC ATC
Pro Gly Thr Ser Glu Asn Ser Ala Phe Arg Phe Leu Phe Asn Leu Ser Ser Ile 852                    867                    882                    897
CCT GAG AAC GAG GTG ATC TCC TCT GCA GAG CTT CGG CTC TTC CGG GAG CAG GTG
Pro Glu Asn Glu Val Ile Ser Ser Ala Glu Leu Arg Leu Phe Arg Glu Gln Val 912                    927                    942
GAC CAG GGC CCT GAT TGG GAA AGG GGC TTC CAC CGT ATA AAC ATT TAT GAG GTT
Asp Gln Gly Pro Asp Trp Glu Arg Gly Phe His Arg Ile Asn Ile Tyr Glu Val 957                    972                    987                   1002
ATG AAG CCC CCA GCA GAA GTG GTG CCT GGG CAC CTC ATC ACA CGA CTA CTG GAC
MET Lys Pro Pro Ala Glu Val Val Pro Gly His Leu Ile Thr Arg Leu Leu Asp 1017                   1032                   1047
ACG AGA CTG GTC CAC CAC AAT GTG ACA CGG TGG GAA ACT TTT GAT GTG AGC CCT
Thr Arg Leu Val His His Asn Val Thr Arg Trp Glu Thr Phe Asp Val Ser Pro 1062                   1077                   1092                   1107
GCG GTC CTT CGC TGG ACC CGG GAG AAG CAG CCA AAC TAT GGG CTA GCC ATT GAG
Ala Val Leu Arg Trp Thr Arg Glu Lys Gln Pro Asn Tyr Gly Leu Ala Ile Glu 1122                   1137                   1152                   1167
GTG ACT CAC CTC CAT CAG ACT CGG ACC CAC CAG GGC CAG CAT GTC AGG ATT AGC
Val Thr His Leu His Gln Thr Arg Thr His Gln Gly Gln His Val Arg Ile Ser 1182                   1197                   1212
CGA TCG TTA CCT CAA GGG AGT GGG AAT TGG GCC CAG CTC CGG CCC CTC CTG GTC
Arg Ser Leu Pro Gln Gly Ser Gly Asn Trp Ala Gln Leu Arg Pro Leu Leu Val 1227                   1242                   1257                   1272
ACC TTT GGC CAT GAT GGC CGG GGC CAT GCC TTG ACC CGA CGC CGG AGG GCC AAG
Thr Phe Gly His Asp Gly Arg Gly His Ala Leu Thr Arg Arg Arg Arg Ala Lys 1287                   1302                   1317
CGT AGC CCT AAG CAT CAC TCA CAG CGG GCC AGG AAG AAG AAT AAG AAC TGC CGG
Arg Ser Pro Lys His His Ser Gln Arg Ala Arg Lys Lys Asn Lys Asn Cys Arg
    (293)
```

FIG. 2 (CON'T)

```
1332              1347              1362              1377
CGC CAC TCG CTC TAT GTG GAC TTC AGC GAT GTG GGC TGG AAT GAC TGG ATT GTG
Arg His Ser Leu Tyr Val Asp Phe Ser Asp Val Gly Trp Asn Asp Trp Ile Val 1392              1407              1422              1437
GCC CCA CCA GGC TAC CAG GCC TTC TAC TGC CAT GGG GAC TGC CCC TTT CCA CTG
Ala Pro Pro Gly Tyr Gln Ala Phe Tyr Cys His Gly Asp Cys Pro Phe Pro Leu 1452              1467              1482
GCT GAC CAC CTC AAC TCA ACC AAC CAT GCC ATT GTG CAG ACC CTG GTC AAT TCT
Ala Asp His Leu Asn Ser Thr Asn His Ala Ile Val Gln Thr Leu Val Asn Ser 1497              1512              1527              1542
GTC AAT TCC AGT ATC CCC AAA GCC TGT TGT GTG CCC ACT GAA CTG AGT GCC ATC
Val Asn Ser Ser Ile Pro Lys Ala Cys Cys Val Pro Thr Glu Leu Ser Ala Ile 1557              1572              1587
TCC ATG CTG TAC CTG GAT GAG TAT GAT AAG GTG GTA CTG AAA AAT TAT CAG GAG
Ser MET Leu Tyr Leu Asp Glu Tyr Asp Lys Val Val Leu Lys Asn Tyr Gln Glu 1602              1617   (408)  1636        1646        1656
ATG GTA GTA GAG GGA TGT GGG TGC CGC TGAGATCAGG CAGTCCTTGA GGATAGACAG
MET Val Val Glu Gly Cys Gly Cys Arg 1666       1676       1686       1696       1706       1716       1726
ATATACACAC CACACACACA CACCACATAC ACCACACACA CACGTTCCCA TCCACTCACC CACACACTAC 1736       1746       1756       1766       1776       1786       1796
ACAGACTGCT TCCTTATAGC TGGACTTTTA TTTAAAAAAA AAAAAAAAAA AATGGAAAAA ATCCCTAAAC 1806       1816       1826       1836       1846       1856       1866
ATTCACCTTG ACCTTATTTA TGACTTTACG TGCAAATGTT TTGACCATAT TGATCATATA TTTTGACAAA 1876       1886       1896       1906       1916       1926       1936
ATATATTTAT AACTACGTAT TAAAGAAAA AAATAAAATG AGTCATTATT TTAAAAAAAA AAAAAAACT

1946
CTAGAGTCGA CGGAATTC
```

FIG. 2 (CON'T)

```
                10           20           30           40           50
         GTGACCGAGC  GGCGCGGACG  GCCGCCTGCC  CCCTCTGCCA  CCTGGGGCGG 60           70           80           90         99
         TGCGGGCCCG  GAGCCCGGAG  CCCGGGTAGC  GCGTAGAGCC  GGCGCG ATG
                                                               MET
                                                               (1)

108           117           126           135          144
CAC GTG CGC TCA CTG CGA GCT GCG GCG CCG CAC AGC TTC GTG GCG
His Val Arg Ser Leu Arg Ala Ala Ala Pro His Ser Phe Val Ala 153           162           171           180          189
CTC TGG GCA CCC CTG TTC CTG CTG CGC TCC GCC CTG GCC GAC TTC
Leu Trp Ala Pro Leu Phe Leu Leu Arg Ser Ala Leu Ala Asp Phe 198           207           216           225          234
AGC CTG GAC AAC GAG GTG CAC TCG AGC TTC ATC CAC CGG CGC CTC
Ser Leu Asp Asn Glu Val His Ser Ser Phe Ile His Arg Arg Leu 243           252           261           270          279
CGC AGC CAG GAG CGG CGG GAG ATG CAG CGC GAG ATC CTC TCC ATT
Arg Ser Gln Glu Arg Arg Glu MET Gln Arg Glu Ile Leu Ser Ile 288           297           306           315          324
TTG GGC TTG CCC CAC CGC CCG CGC CCG CAC CTC CAG GGC AAG CAC
Leu Gly Leu Pro His Arg Pro Arg Pro His Leu Gln Gly Lys His 333           342           351           360          369
AAC TCG GCA CCC ATG TTC ATG CTG GAC CTG TAC AAC GCC ATG GCG
Asn Ser Ala Pro MET Phe MET Leu Asp Leu Tyr Asn Ala MET Ala 378           387           396           405          414
GTG GAG GAG GGC GGC GGG CCC GGC GGC CAG GGC TTC TCC TAC CCC
Val Glu Glu Gly Gly Gly Pro Gly Gly Gln Gly Phe Ser Tyr Pro 423           432           441           450          459
TAC AAG GCC GTC TTC AGT ACC CAG GGC CCC CCT CTG GCC AGC CTG
Tyr Lys Ala Val Phe Ser Thr Gln Gly Pro Pro Leu Ala Ser Leu 468           477           486           495          504
CAA GAT AGC CAT TTC CTC ACC GAC GCC GAC ATG GTC ATG AGC TTC
Gln Asp Ser His Phe Leu Thr Asp Ala Asp MET Val MET Ser Phe 513           522           531           540          549
GTC AAC CTC GTG GAA CAT GAC AAG GAA TTC TTC CAC CCA CGC TAC
Val Asn Leu Val Glu His Asp Lys Glu Phe Phe His Pro Arg Tyr
```

FIG. 3

```
        558              567              576              585              594
CAC CAT CGA GAG TTC CGG TTT GAT CTT TCC AAG ATC CCA GAA GGG
His His Arg Glu Phe Arg Phe Asp Leu Ser Lys Ile Pro Glu Gly 603              612              621              630              639
GAA GCT GTC ACG GCA GCC GAA TTC CGG ATC TAC AAG GAC TAC ATC
Glu Ala Val Thr Ala Ala Glu Phe Arg Ile Tyr Lys Asp Tyr Ile 648              657              666              675              684
CGG GAA CGC TTC GAC AAT GAG ACG TTC CGG ATC AGC GTT TAT CAG
Arg Glu Arg Phe Asp Asn Glu Thr Phe Arg Ile Ser Val Tyr Gln 693              702              711              720              729
GTG CTC CAG GAG CAC TTG GGC AGG GAA TCG GAT CTC TTC CTG CTC
Val Leu Gln Glu His Leu Gly Arg Glu Ser Asp Leu Phe Leu Leu 738              747              756              765              774
GAC AGC CGT ACC CTC TGG GCC TCG GAG GAG GGC TGG CTG GTG TTT
Asp Ser Arg Thr Leu Trp Ala Ser Glu Glu Gly Trp Leu Val Phe 783              792              801              810              819
GAC ATC ACA GCC ACC AGC AAC CAC TGG GTG GTC AAT CCG CGG CAC
Asp Ile Thr Ala Thr Ser Asn His Trp Val Val Asn Pro Arg His 828              837              846              855              864
AAC CTG GGC CTG CAG CTC TCG GTG GAG ACG CTG GAT GGG CAG AGC
Asn Leu Gly Leu Gln Leu Ser Val Glu Thr Leu Asp Gly Gln Ser 873              882              891              900              909
ATC AAC CCC AAG TTG GCG GGC CTG ATT GGG CGG CAC GGG CCC CAG
Ile Asn Pro Lys Leu Ala Gly Leu Ile Gly Arg His Gly Pro Gln 918              927              936              945              954
AAC AAG CAG CCC TTC ATG GTG GCT TTC TTC AAG GCC ACG GAG GTC
Asn Lys Gln Pro Phe MET Val Ala Phe Phe Lys Ala Thr Glu Val 963              972              981              990              999
CAC TTC CGC AGC ATC CGG TCC ACG GGG AGC AAA CAG CGC AGC CAG
His Phe Arg Ser Ile Arg Ser Thr Gly Ser Lys Gln Arg Ser Gln
                            (293)
       1008             1017             1026             1035             1044
AAC CGC TCC AAG ACG CCC AAG AAC CAG GAA GCC CTG CGG ATG GCC
Asn Arg Ser Lys Thr Pro Lys Asn Gln Glu Ala Leu Arg MET Ala 1053             1062             1071             1080             1089
AAC GTG GCA GAG AAC AGC AGC AGC GAC CAG AGG CAG GCC TGT AAG
Asn Val Ala Glu Asn Ser Ser Ser Asp Gln Arg Gln Ala Cys Lys
```

*FIG. 3 (CON'T)*

```
             1098          1107         1116         1125         1134
AAG CAC GAG CTG TAT GTC AGC TTC CGA GAC CTG GGC TGG CAG GAC
Lys His Glu Leu Tyr Val Ser Phe Arg Asp leu Gly Trp Gln Asp 1143          1152         1161         1170         1179
TGG ATC ATC GCG CCT GAA GGC TAC GCC GCC TAC TAC TGT GAG GGG
Trp Ile Ile Ala Pro Glu Gly Tyr Ala Ala Tyr Tyr Cys Glu Gly 1188          1197         1206         1215         1224
GAG TGT GCC TTC CCT CTG AAC TCC TAC ATG AAC GCC ACC AAC CAC
Glu Cys Ala Phe Pro Leu Asn Ser Tyr MET Asn Ala Thr Asn His 1233          1242         1251         1260         1269
GCC ATC GTG CAG ACG CTG GTC CAC TTC ATC AAC CCG GAA ACG GTG
Ala Ile Val Gln Thr Leu Val His Phe Ile Asn Pro Glu Thr Val 1278          1287         1296         1305         1314
CCC AAG CCC TGC TGT GCG CCC ACG CAG CTC AAT GCC ATC TCC GTC
Pro Lys Pro Cys Cys Ala Pro Thr Gln Leu Asn Ala Ile Ser Val 1323          1332         1341         1350         1359
CTC TAC TTC GAT GAC AGC TCC AAC GTC ATC CTG AAG AAA TAC AGA
Leu Tyr Phe asp Asp Ser Ser Asn Val Ile Leu lys Lys Tyr Arg 1368          1377         1386              1399
AAC ATG GTG GTC CGG GCC TGT GGC TGC CAC TAGCTCCTCC
Asn MET VAl Val Arg Ala Cys Gly Cys His
                                        (431)

1409         1419        1429         1439       1448
GAGAATTCAG ACCCTTTGGG GCCAAGTTTT TCTGGATCCT CCATTGCTC
```

FIG. 3 (CON'T)

```
                  10         20         30         40         50
         CGACCATGAG AGATAAGGAC TGAGGGCCAG GAAGGGGAAG CGAGCCCGCC 60         70         80         90        100
         GAGAGGTGGC GGGGACTGCT CACGCCAAGG GCCACAGCGG CCGCGCTCCG 110        120        130        140        150
         GCCTCGCTCC GCCGCTCCAC GCCTCGCGGG ATCCGCGGGG GCAGCCCGGC 159        168        177        186        195
         CGGGCGGGG ATG CCG GGG CTG GGG CGG AGG GCG CAG TGG CTG TGC
                   MET Pro Gly Leu Gly Arg Arg Ala Gln Trp Leu cys
                   (1)

204        213        222        231        240
         TGG TGG TGG GGG CTG CTG TGC AGC TGC TGC GGG CCC CCG CCG CTG
         Trp Trp Trp Gly Leu Leu Cys Ser Cys Cys Gly Pro Pro Pro Leu 249        258        267        276        285
         CGG CCG CCC TTG CCC GCT GCC GCG GCC GCC GCC GCC GGG GGG CAG
         Arg Pro Pro Leu pro Ala Ala Ala Ala Ala Ala Ala Gly Gly Gln 294        303        312        321        330
         CTG CTG GGG GAC GGC GGG AGC CCC GGC CGC ACG GAG CAG CCG CCG
         Leu Leu Gly Asp Gly Gly Ser Pro Gly Arg Thr Glu Gln Pro Pro 339        348        357        366        375
         CCG TCG CCG CAG TCC TCC TCG GGC TTC CTG TAC CGG CGG CTC AAG
         Pro Ser Pro Gln Ser Ser Ser Gly Phe Leu Tyr Arg Arg Leu Lys 384        393        402        411        420
         ACG CAG GAG AAG CGG GAG ATG CAG AAG GAG ATC TTG TCG GTG CTG
         Thr Gln Glu Lys Arg Glu MET gln Lys Glu Ile Leu Ser Val Leu 429        438        447        456        465
         GGG CTC CCG CAC CGG CCC CGG CCC CTG CAC GGC CTC CAA CAG CCG
         Gly Leu Pro His Arg Pro Arg Pro Leu His Gly Leu Gln Gln Pro
```

FIG. 4

```
      474           483           492           501           510
CAG CCC CCG GCG CTC CGG CAG CAG GAG GAG CAG CAG CAG CAG CAG
Gln Pro Pro Ala Leu Arg Gln Gln Glu glu Gln Gln Gln Gln Gln 519           528           537           546           555
CAG CTG CCT CGC GGA GAG CCC CCT CCC GGG CGA CTG AAG TCC GCG
Gln Leu Pro Arg Gly Glu Pro Pro Pro Gly Arg Leu Lys Ser Ala 564           573           582           591           600
CCC CTC TTC ATG CTG GAT CTG TAC AAC GCC CTG TCC GCC GAC AAC
Pro Leu Phe MET Leu Asp Leu Tyr Asn Ala Leu Ser Ala Asp Asn 609           618           627           636           645
GAC GAG GAC GGG GCG TCG GAG GGG GAG AGG CAG CAG TCC TGG CCC
Asp Glu asp Gly Ala Ser Glu Gly Glu Arg Gln Gln Ser Trp Pro 654           663           672           681           690
CAC GAA GCA GCC AGC TCG TCC CAG CGT CGG CAG CCG CCC CCG GGC
His Glu Ala Ala Ser Ser Ser Gln Arg Arg Gln Pro Pro Pro Gly 699           708           717           726           735
GCC GCG CAC CCG CTC AAC CGC AAG AGC CTT CTG GCC CCC GGA TCT
Pro Pro Gly Ala Ala His Pro Leu Asn Arg Lys Ser Leu Leu Ala 744           753           762           771           780
GGC AGC GGC GGC GCG TCC CCA CTG ACC AGC GCG CAG GAC AGC GCC
Gly Ser Gly Gly Ala Ser Pro Leu Thr Ser Ala Gln Asp Ser Ala 789           798           807           816           825
TTC CTC AAC GAC GCG GAC ATG GTC ATG AGC TTT GTG AAC CTG GTG
Phe Leu Asn Asp Ala Asp MET Val MET Ser Phe Val Asn Leu Val 834           843           852           861           870
GAG TAC GAC AAG GAG TTC TCC CCT CGT CAG CGA CAC CAC AAA GAG
Glu Tyr Asp Lys Glu Phe Ser Pro Arg Gln Arg His His Lys Glu 879           888           897           906           915
TTC AAG TTC AAC TTA TCC CAG ATT CCT GAG GGT GAG GTG GTG ACG
Phe Lys Phe Asn leu Ser Gln Ile Pro Glu Gly Glu Val Val Thr 924           933           942           951           960
GCT GCA GAA TTC CGC ATC TAC AAG GAC TGT GTT ATG GGG AGT TTT
Phe Arg Ile Tyr Lys Asp Cys Val MEt Ala Ala Glu Gly Ser Phe
```

FIG. 4 (CON'T)

```
            969           978           987           996          1005
AAA AAC CAA ACT TTT CTT ATC AGC ATT TAT CAA GTC TTA CAG GAG
Lys Asn Gln Thr Phe Leu Ile Ser Ile Tyr Gln Val Leu Gln Glu 1014          1023          1032          1041          1050
CAT CAG CAC AGA GAC TCT GAC CTG TTT TTG TTG GAC ACC CGT GTA
His Gln His Arg Asp Ser Asp Leu Phe Leu Leu Asp Thr Arg Val 1059          1068          1077          1086          1095
GTA TGG GCC TCA GAA GAA GGC TGG CTG GAA TTT GAC ATC ACG GCC
Val Trp Ala Ser Glu Glu Gly Trp Leu Glu Phe Asp Ile Thr Ala 1104          1113          1122          1131          1140
ACT AGC AAT CTG TGG GTT GTG ACT CCA CAG CAT AAC ATG GGG CTT
Thr Ser Asn Leu Trp Val Val Thr Pro Gln His Asn MET Gly Leu 1149          1158          1167          1176          1185
CAG CTG AGC GTG GTG ACA AGG GAT GGA GTC CAC GTC CAC CCC CGA
Gln Leu Ser Val Val Thr Arg Asp Gly Val His Val His Pro Arg 1194          1203          1212          1221          1230
GCC GCA GGC CTG GTG GGC AGA GAC GGC CCT TAC GAT AAG CAG CCC
Ala Ala Gly Leu Val Gly Arg Asp Gly Pro Tyr Asp Lys Gln Pro 1239          1248          1257          1266          1275
TTC ATG GTG GCT TTC TTC AAA GTG AGT GAG GTC CAC GTG CGC ACC
Phe MET Val Ala Phe Phe Lys Val Ser Glu Val His Val Arg Thr 1284          1293          1302          1311          1320
ACC AGG TCA GCC TCC AGC CGG CGC CGA CAA CAG AGT CGT AAT CGC
Thr Arg Ser Ala Ser Ser Arg Arg Arg Gln Gln Ser Arg Asn Arg
                                       (382)
           1329          1338          1347          1356          1365
TCT ACC CAG TCC CAG GAC GTG GCG CGG GTC TCC AGT GCT TCA GAT
Ser Thr Gln Ser Gln Asp Val Ala Arg Val Ser Ser Ala Ser Asp
(388)
           1374          1383          1392          1401          1410
TAC AAC AGC AGT GAA TTG AAA ACA GCC TGC AGG AAG CAT GAG CTG
Tyr Asn Ser Ser Glu Leu Lys Thr Ala Cys Arg Lys His Glu Leu
                                                    (412)
           1419          1428          1437          1446          1455
TAT GTG AGT TTC CAA GAC CTG GGA TGG CAG GAC TGG ATC ATT GCA
Tyr Val Ser Phe Gln Asp Leu Gly Trp Gln Asp Trp Ile Ile Ala
```

FIG. 4 (CON'T)

```
      1464          1473          1482          1491          1500
CCC AAG GGC TAT GCT GCC AAT TAC TGT GAT GGA GAA TGC TCC TTC
Pro Lys Gly Tyr Ala Ala Asn Tyr Cys Asp Gly Glu Cys Ser Phe 1509          1518          1527          1536          1545
CCA CTC AAC GCA CAC ATG AAT GCA ACC AAC CAC GCG ATT GTG CAG
Pro Leu Asn Ala His MET Asn Ala Thr Asn His Ala Ile Val Gln 1554          1563          1572          1581          1590
ACC TTG GTT CAC CTT ATG AAC CCC GAG TAT GTC CCC AAA CCG TGC
Thr Leu Val His Leu MET Asn Pro Glu Tyr Val Pro Lys Pro Cys 1599          1608          1617          1626          1635
TGT GCG CCA ACT AAG CTA AAT GCC ATC TCG GTT CTT TAC TTT GAT
Cys Ala Pro Thr Lys Leu Asn Ala Ile Ser Val Leu Tyr Phe Asp 1644          1653          1662          1671          1680
GAC AAC TCC AAT GTC ATT CTG AAA AAA TAC AGG AAT ATG GTT GTA
Asp Asn Ser Asn Val Ile Leu Lys Lys Tyr Arg Asn MET Val Val 1689          1698         1708          1718          1728
AGA GCT TGT GGA TGC CAC TAACTCGAAA CCAGATGCTG GGACACACA
Arg Ala Cys Gly Cys His
                  (513)
      1738         1748          1758          1768          1778
TTCTGCCTTG GATTCCTAGA TTACATCTGC CTTAAAAAAA CACGGAAGCA 1788          1798          1808          1818          1828
CAGTTGGAGG TGGGACGATG AGACTTTGAA ACTATCTCAT GCCAGTGCCT 1838          1848          1858          1868          1878
TATTACCCAG GAAGATTTTA AAGGACCTCA TTAATAATTT GCTCACTTGG 1888          1898          1908          1918          1928
TAAATGACGT GAGTAGTTGT TGGTCTGTAG CAAGCTGAGT TTGGATGTCT 1938          1948          1958          1968          1978
GTAGCATAAG GTCTGGTAAC TGCAGAAACA TAACCGTGAA GCTCTTCCTA 1988          1998          2008          2018          2028
CCCTCCTCCC CCAAAAACCC ACCAAAATTA GTTTTAGCTG TAGATCAAGC 2038          2048          2058          2068          2078
TATTTGGGGT GTTTGTTAGT AAATAGGGAA AATAATCTCA AGGAGTTAA 2088          2098          2108          2118          2128
ATGTATTCTT GGCTAAAGGA TCAGCTGGTT CAGTACTGTC TATCAAAGGT
```

FIG. 4 (CON'T)

```
        2138        2148        2158        2168        2178
AGATTTTACA  GAGAACAGAA  ATCGGGGAAG  TGGGGGGAAC  GCCTCTGTTC 2188        2198        2208        2218        2228
AGTTCATTCC  CAGAAGTCCA  CAGGACGCAC  AGCCCAGGCC  ACAGCCAGGG 2238        2248        2258        2268        2278
CTCCACGGGG  CGCCCTTGTC  TCAGTCATTG  CTGTTGTATG  TTCGTGCTGG 2288        2298        2308        2318        2328
AGTTTTGTTG  GTGTGAAAAT  ACACTTATTT  CAGCCAAAAC  ATACCATTTC 2338        2348        2358        2368        2378
TACACCTCAA  TCCTCCATTT  GCTGTACTCT  TTGCTAGTAC  CAAAAGTAGA 2388        2398        2408        2418        2428
CTGATTACAC  TGAGGTGAGG  CTACAAGGGG  TGTGTAACCG  TGTAACACGT 2438        2448        2458        2458        2478
GAAGGCAGTG  CTCACCTCTT  CTTTACCAGA  ACGGTTCTTT  GACCAGCACA 2488        2498        2508        2518        2528
TTAACTTCTG  GACTGCCGGC  TCTAGTACCT  TTTCAGTAAA  GTGGTTCTCT 2538        2548        2558        2568        2578
GCCTTTTTAC  TATACAGCAT  ACCACGCCAC  AGGGTTAGAA  CCAACGAAGA 2588        2598        2608        2618        2628
AAATAAAATG  AGGGTGCCCA  GCTTATAAGA  ATGGTGTTAG  GGGGATGAGC 2638        2648        2658        2668        2678
ATGCTGTTTA  TGAACGGAAA  TCATGATTTC  CCTGTAGAAA  GTGAGGCTCA 2688        2698        2708        2718        2728
GATTAAATTT  TAGAATATTT  TCTAAATGTC  TTTTTCACAA  TCATGTGACT 2738        2748        2758        2768        2778
GGGAAGGCAA  TTTCATACTA  AACTGATTAA  ATAATACATT  TATAATCTAC 2788        2798        2808        2818        2828
AACTGTTTGC  ACTTACAGCT  TTTTTTGTAA  ATATAAACTA  TAATTTATTG 2838        2848        2858        2868        2878
TCTATTTTAT  ATCTGTTTTG  CTGTGGCGTT  GGGGGGGGGG  CCGGGCTTTT 2888        2898        2908        2918
GGGGGGGGGG  GTTTGTTTGG  GGGGTGTCGT  GGTGTGGGCG  GGCGG
```

FIG. 4 (CON'T)

```
         10         20         30         40         50
CTGGTATATT TGTGCCTGCT GGAGGTGGAA TTAACAGTAA GAAGGAGAAA 60         70         80         90        100
GGGATTGAAT GGACTTACAG GAAGGATTTC AAGTAAATTC AGGGAAACAC 110        120        130        140        150
ATTTACTTGA ATAGTACAAC CTAGAGTATT ATTTTACACT AAGACGACAC 160        170        180        190        200
AAAAGATGTT AAAGTTATCA CCAAGCTGCC GGACAGATAT ATATTCCAAC 210        220        230        240        250
ACCAAGGTGC AGATCAGCAT AGATCTGTGA TTCAGAAATC AGGATTTGTT 260        270        280        290        300
TTGGAAAGAG CTCAAGGGTT GAGAAGAACT CAAAAGCAAG TGAAGATTAC 310        320        330        340        350
TTTGGGAACT ACAGTTTATC AGAAGATCAA CTTTTGCTAA TTCAAATACC 360        370        380        390        400
AAAGGCCTGA TTATCATAAA TTCATATAGG AATGCATAGG TCATCTGATC 410        420        430        440        450
AAATAATATT AGCCGTCTTC TGCTACATCA ATGCAGCAAA AACTCTTAAC 460        470        480        490        500
AACTGTGGAT AATTGGAAAT CTGAGTTTCA GCTTTCTTAG AAATAACTAC 510        520        530        540        550
TCTTGACATA TTCCAAAATA TTTAAAATAG GACAGGAAAA TCGGTGAGGA 560        570        580        590        600
TGTTGTGCTC AGAAATGTCA CTGTCATGAA AATAGGTAA ATTTGTTTTT 610        620        630        640        650
TCAGCTACTG GGAAACTGTA CCTCCTAGAA CCTTAGGTTT TTTTTTTTT 660        670        680        690        700
AAGAGGACAA GAAGGACTAA AAATATCAAC TTTTGCTTTT GGACAAAA
```

FIG. 5

```
701             710             719             728             737
ATG CAT CTG ACT GTA TTT TTA CTT AAG GGT ATT GTG GGT TTC CTC
MET His Leu Thr Val Phe Leu Leu Lys Gly Ile Val Gly Phe Leu
(1)
746             755             764             773             782
TGG AGC TGC TGG GTT CTA GTG GGT TAT GCA AAA GGA GGT TTG GGA
Trp Ser Cys Trp Val Leu Val Gly Tyr Ala Lys Gly Gly Leu Gly 791             800             809             818             827
GAC AAT CAT GTT CAC TCC AGT TTT ATT TAT AGA AGA CTA CGG AAC
Asp Asn His Val His Ser Ser Phe Ile Tyr Arg Arg Leu Arg Asn 836             845             854             863             872
CAC GAA AGA CGG GAA ATA CAA AGG GAA ATT CTC TCT ATC TTG GGT
His Glu Arg Arg Glu Ile Gln arg Glu Ile Leu Ser Ile Leu Gly 881             890             899             908             917
TTG CCT CAC AGA CCC AGA CCA TTT TCA CCT GGA AAA ATG ACC AAT
Leu Pro His Arg Pro Arg Pro Phe Ser Pro Gly Lys Gln Ala Ser 926             935             944             953             962
CAA GCG TCC TCT GCA CCT CTC TTT ATG CTG GAT CTC TAC AAT GCC
Ser Ala Pro Leu Phe MET Leu Asp Leu Tyr Asn Ala MET Thr Asn 971             980             989             998             1007
GAA GAA AAT CCT GAA GAG TCG GAG TAC TCA GTA AGG GCA TCC TTG
Glu Glu Asn Pro Glu Glu Ser Glu Tyr Ser Val Arg Ala Ser Leu 1016            1025            1034            1043            1052
GCA GAA GAG ACC AGA GGG GCA AGA AAG GGA TAC CCA GCC TCT CCC
Ala Glu Glu Thr Arg Gly Ala Arg Lys Gly Tyr Pro Ala Ser Pro 1061            1070            1079            1088            1097
AAT GGG TAT CCT CGT CGC ATA CAG TTA TCT CGG ACG ACT CCT CTG
Asn Gly Tyr Pro Arg Arg Ile Gln Leu Ser Arg Thr Thr Pro Leu 1106            1115            1124            1133            1142
ACC ACC CAG AGT CCT CCT CTA GCC AGC CTC CAT GAT ACC AAC TTT
Thr Thr Gln Ser Pro Pro Leu Ala Ser Leu His Asp Thr Asn Phe 1151            1160            1169            1178            1187
CTG AAT GAT GCT GAC ATG GTC ATG AGC TTT GTC AAC TTA GTT GAA
Leu Asn Asp Ala Asp MET Val MET Ser Phe Val Asn Leu Val Glu 1196            1205            1214            1223            1232
AGA GAC AAG GAT TTT TCT CAC CAG CGA AGG CAT TAC AAA GAA TTT
Arg Asp Lys Asp Phe Ser His Gln Arg Arg His Tyr Lys Glu Phe
```

FIG. 5 (CON'T)

```
1241            1250            1259            1268            1277
 CGA TTT GAT CTT ACC CAA ATT CCT CAT GGA GAG GCA GTG ACA GCA
 Arg Phe Asp Leu Thr Gln Ile Pro His Gly Glu Ala Val Thr Ala 1286            1295            1304            1313            1322
 GCT GAA TTC CGG ATA TAC AAG GAC CGG AGC AAC AAC CGA TTT GAA
 Ala Glu Phe Arg Ile Tyr Lys Asp Arg Ser Asn Asn Arg Phe Glu 1331            1340            1349            1358            1367
 AAT GAA ACA ATT AAG ATT AGC ATA TAT CAA ATC ATC AAG GAA TAC
 Asn Glu Thr Ile Lys Ile Ser Ile Tyr Gln Ile Ile Lys Glu Tyr 1376            1385            1394            1403            1412
 ACA AAT AGG GAT GCA GAT CTG TTC TTG TTA GAC ACA AGA AAG GCC
 Thr Asn Arg Asp Ala Asp Leu Phe Leu Leu Asp Thr Arg Lus Ala 1421            1430            1439            1448            1457
 CAA GCT TTA GAT GTG GGT TGG CTT GTC TTT GAT ATC ACT GTG ACC
 Gln Ala Leu Asp Val Gly Trp Leu Val Phe Asp Ile Thr Val Thr 1466            1475            1484            1493            1502
 AGC AAT CAT TGG GTG ATT AAT CCC CAG AAT AAT TTG GGC TTA CAG
 Ser Asn His Trp Val Ile Asn Pro Gln Asn Asn Leu Gly Leu Gln 1511            1520            1529            1538            1547
 CTC TGT GCA GAA ACA GGG GAT GGA CGC AGT ATC AAC GTA AAA TCT
 Leu Cys Ala Glu Thr Gly Asp Gly Arg Ser Ile Asn Val Lys Ser 1556            1565            1574            1583            1592
 GCT GGT CTT GTG GGA AGA CAG GGA CCT CAG TCA AAA CAA CCA TTC
 Ala Gly Leu Val Gly Arg Gln Gly Pro Gln Ser Lys Gln Pro Phe 1601            1610            1619            1628            1637
 ATG GTG GCC TTC TTC AAG GCG AGT GAG GTA CTT CTT CGA TCC GTG
 MET Val Ala Phe Phe Lys Ala Ser Glu VAl Leu Leu Arg Ser Val 1646            1655            1664            1673            1682
 AGA GCA GCC AAC AAA CGA AAA AAT CAA AAC CGC AAT AAA TCC AGC
 Arg Ala Ala Asn Lys Arg Lys Asn Gln Asn Arg Asn Lys Ser Ser
                                                     (329)
1691            1700            1709            1718            1727
 TCT CAT CAG GAC TCC TCC AGA ATG TCC AGT GTT GGA GAT TAT AAC
 Ser His Gln Asp Ser Ser Arg MET Ser Ser Val Gly Asp Tyr Asn
                  (337)
```

FIG. 5 (CON'T)

```
1736           1745           1754           1763           1722
ACA AGT GAG CAA AAA CAA GCC TGT AAG AAG CAC GAA CTC TAT GTG
Thr Ser Glu Gln Lys Gln Ala Cys Lys Lys His Glu Leu Tyr Val
                                         (356)

1781           1790           1799           1808           1817
AGC TTC CGG GAT CTG GGA TGG CAG GAC TGG ATT ATA GCA CCA GAA
Ser Phe Arg Asp Leu Gly Trp Gln Asp Trp Ile Ile Ala Pro Glu
(362)
1826           1835           1844           1853           1862
GGA TAC GCT GCA TTT TAT TGT GAT GGA GAA TGT TCT TTT CCA CTT
Gly Tyr Ala Ala Phe Tyr Cys Asp Gly Glu Cys Ser Phe Pro Leu 1871           1880           1889           1898           1907
AAC GCC CAT ATG AAT GCC ACC AAC CAC GCT ATA GTT CAG ACT CTG
Asn Ala His MET Asn Ala Thr Asn His Ala Ile Val Gln Thr Leu 1916           1925           1934           1943           1952
GTT CAT CTG ATG TTT CCT GAC CAC GTA CCA AAG CCT TGT TGT GCT
Val His Leu MET Phe Pro Asp His Val Pro Lys Pro Cys Cys Ala 1961           1970           1979           1988           1997
CCA ACC AAA TTA AAT GCC ATC TCT GTT CTG TAC TTT GAT GAC AGC
Pro Thr Lys Leu Asn Ala Ile Ser Val Leu Tyr Phe Asp Asp Ser 2006           2015           2024           2033           2042
TCC AAT GTC ATT TTG AAA AAA TAT AGA AAT ATG GTA GTA CGC TCA
Ser Asn Val Ile Leu Lys Lys Tyr Arg Asn MET Val Val Arg Ser 2051           2060      2070       2080       2090       2100
TGT GGC TGC CAC TAATATTAAA TAATATTGAT AATAACAAAA AGATCTGTAT
Cys Gly Cys His
              (454)
       2110       2120       2130       2140       2150
TAAGGTTTAT GGCTGCAATA AAAAGCATAC TTTCAGACAA ACAGAAAAAA AAA
```

FIG. 5 (CON'T)

```
       (1)
GAATTCC GAG CCC CAT TGG AAG GAG TTC CGC TTT GAC CTG ACC CAG ATC CCG GCT
        Glu Pro His Trp Lys Glu Phe Arg Phe Asp Leu Thr Gln Ile Pro Ala
                                              (10)

GGG GAG GCG GTC ACA GCT GCG GAG TTC CGG ATT TAC AAG GTG CCC AGC ATC CAC
Gly Glu Ala Val Thr Ala Ala Glu Phe Arg Ile Tyr Lys Val Pro Ser Ile His
            (20)                                (30)

CTG CTC AAC AGG ACC CTC CAC GTC AGC ATG TTC CAG GTG GTC CAG GAG CAG TCC
Leu Leu Asn Arg Thr Leu His Val Ser Met Phe Gln Val Val Gln Glu Gln Ser
                (40)                                    (50)

AAC AGG GAG TCT GAC TTG TTC TTT TTG GAT CTT CAG ACG CTC CGA GCT GGA GAC
Asn Arg Glu Ser Asp Leu Phe Phe Leu Asp Leu Gln Thr Leu Arg Ala Gly Asp
                        (60)                                        (70)

GAG GGC TGG CTG GTG CTG GAT GTC ACA GCA GCC AGT GAC TGC TGG TTG CTG AAG
Glu Gly Typ Leu Val Leu Asp Val Thr Ala Ala Ser Asp Cyc Trp Leu Leu Lys
                                    (80)

CGT CAC AAG GAC CTG GGA CTC CGC CTC TAT GTG GAG ACT GAG GAT GGG CAC AGC
Arg His Lys Asp Leu Gly Lue Arg Leu Tyr Val Glu Thr Glu Asp Gly His Ser
    (90)                                    (100)

GTG GAT CCT GGC CTG GCC GGC CTG CTG GGT CAA CGG GCC CCA CGC TCC CAA CAG
Val Asp Pro Gly Leu Ala Gly Leu Leu Gly Gln Arg Ala Pro Arg Ser Gln Gln
            (110)                                   (120)

CCT TTC GTG GTC ACT TTC TTC AGG GCC AGT CCG AGT CCC ATC CGC ACC CCT CGG
Pro Phe Val Val Thr Phe Phe Arg Ala Ser Pro Ser Pro Ile Arg Thr Pro Arg
                (130)                                   (140)

GCA GTG AGG CCA CTG AGG AGG AGG CAG CCG AAG AAA AGC AAC GAG CTG CCG CAG
Ala Val Arg Pro Leu Arg Arg Arg Gln Pro Lys Lys Ser Asn Glu Leu Pro Gln
                            (150)                                   (160)

GCC AAC CGA CTC CCA GGG ATC TTT GAT GAC GTC CAC GGC TCC CAC GGC CGG CAG
Ala Asn Arg Leu Pro Gly Ile Phe Asp Asp Val His Gly Ser His Gly Arg Gln
                                (170)

GTC TGC CGT CGG CAC GAG CTC TAC GTC AGC TTC CAG GAC CTT GGC TGG CTG GAC
Val Cys Arg Arg His Glu Leu Tyr Val Ser Phe Gln Asp Leu Gly Trp Leu Asp
    (180)                                       (190)

TGG GTC ATC GCC CCC CAA GGC TAC TCA GCC TAT TAC TGT GAG GGG GAG TGC TCC
Trp Val Ile Ala Pro Gln Gly Tyr Ser Ala Tyr Tyr Cys Glu Gly Glu Cys Ser
            (200)                                   (210)

TTC CCG CTG GAC TCC TGC ATG AAC GCC ACC AAC CAC GCC ATC CTG CAG TCC CTG
Phe Pro Leu Asp Ser Cys Met Asn Ala Thr Asn His Ala Ile Leu Gln Ser Leu
                    (220)                                       (230)
```

FIG. 6

```
GTG CAC CTG ATG AAG CCA AAC GCA GTC CCC AAG GCG TGC TGT GCA CCC ACC AAG
Val His Leu Met Lys Pro Asn Ala Val Pro Lys Ala Cys Cys Ala Pro Thr Lys
                            (240)                                  (250)

CTG AGC GCC ACC TCT GTG CTC TAC TAT GAC AGC AGC AAC AAC GTC ATC CTG CGC
Leu Ser Ala Thr Ser Val Leu Tyr Tyr Asp Ser Ser Asn Asn Val Ile Leu Arg
                                (260)

AAG CAC CGC AAC ATG GTG GTC AAG GCC TGC GGC TGC CAC TGAGTCAGCCCGCCCAGC
Lys His Arg Asn Met Val Val Lys Ala Cys Gly Cys His
    (270)                                     (280)

CCTACTGCAGCCACCCTTCTCATCTGGATCGGGCCCTGCAGAGGCAGAAAACCCTTAAATGCTGTCACAG

CTCAAGCAGGAGTGTCAGGGGCCCTCACTCTCGGTGCCTACTTCCTGTCAGGCTTCTGGGAATTC
```

FIG. 6 (CON'T)

```
GACGAAAGGG CCTCGTGATA CGCCTATTTT TATAGGTTAA TGTCATGATA ATAATGGTTT    60
CTTAGACGTC AGGTGGCACT TTTCGGGGAA ATGTGCGCGG AACCCCTATT TGTTTATTTT   120
TCTAAATACA TTCAAATATG TATCCGCTCA TGAGACAATA ACCCTGATAA ATGCTTCAAT   180
AATATTGAAA AGGAAGAGT ATGAGTATTC AACATTTCCG TGTCGCCCTT ATTCCCTTTT    240
TTGCGGCATT TTGCCTTCCT GTTTTGCTC ACCCAGAAAC GCTGGTGAAA GTAAAAGATG    300
CTGAAGATCA GTTGGGTGCA CGAGTGGGTT ACATCGAACT GGATCTCAAC AGCGGTAAGA   360
TCCTTGAGAG TTTTCGCCCC GAAGAACGTT TTCCAATGAT GAGCACTTTT AAAGTTCTGC   420
TATGTGGCGC GGTATTATCC CGTATTGACG CCGGGCAAGA GCAACTCGGT CGCCGCATAC   480
ACTATTCTCA GAATGACTTG GTTGAGTACT CACCAGTCAC AGAAAAGCAT CTTACGGATG   520
GCATGACAGT AAGAGAATTA TGCAGTGCTG CCATAACCAT GAGTGATAAC ACTGCGGCCA   600
ACTTACTTCT GACAACGATC GGAGGACCGA AGGAGCTAAC CGCTTTTTTG CACAACATGG   660
GGGATCATGT AACTCGCCTT GATCGTTGGG AACCGGAGCT GAATGAAGCC ATACCAAACG   720
ACGAGCGTGA CACCACGATG CCTGTAGCAA TGGCAACAAC GTTGCGCAAA CTATTAACTG   780
GCGAACTACT TACTCTAGCT TCCCGGCAAC AATTAATAGA CTGGATGGAG GCGGATAAAG   840
TTGCAGGACC ACTTCTGCGC TCGGCCCTTC CGGCTGGCTG GTTTATTGCT GATAAATCTG   900
GAGCCGGTGA GCGTGGGTCT CGCGGTATCA TTGCAGCACT GGGGCCAGAT GGTAAGCCCT   960
CCCGTATCGT AGTTATCTAC ACGACGGGGA GTCAGGCAAC TATGGATGAA CGAAATAGAC  1020
AGATCGCTGA GATAGGTGCC TCACTGATTA AGCATTGGTA ACTGTCAGAC CAAGTTTACT  1080
CATATATACT TTAGATTGAT TTAAAACTTC ATTTTTAATT TAAAAGGATC TAGGTGAAGA  1140
TCCTTTTTGA TAATCTCATG ACCAAAATCC CTTAACGTGA GTTTTCGTTC CACTGAGCGT  1200
CAGACCCCGT AGAAAAGATC AAAGGATCTT CTTGAGATCC TTTTTTTCTG CGCGTAATCT  1260
GCTGCTTGCA ACAAAAAAA CCACCGCTAC CAGCGGTGGT TTGTTTGCCG GATCAAGAGC  1320
TACCAACTCT TTTTCCGAAG GTAACTGGCT TCAGCAGAGC GCAGATACCA AATACTGTCC  1380
TTCTAGTGTA GCCGTAGTTA GGCCACCACT TCAAGAACTC TGTAGCACCG CCTACATACC  1440
TCGCTCTGCT AATCCTGTTA CCAGTGGCTG CTGCCAGTGG CGATAAGTCG TGTCTTACCG  1500
GGTTGGACTC AAGACGATAG TTACCGGATA AGGCGCAGCG GTCGGGCTGA ACGGGGGGTT  1560
CGTGCACACA GCCCAGCTTG GAGCGAACGA CCTACACCGA ACTGAGATAC CTACAGCGTG  1620
AGCATTGAGA AAGCGCCACG CTTCCCGAAG GGAGAAAGGC GGACAGGTAT CCGGTAAGCG  1680
GCAGGGTCGG AACAGGAGAG CGCACGAGGG AGCTTCCAGG GGGAAACGCC TGGTATCTTT  1740
ATAGTCCTGT CGGGTTTCGC CACCTCTGAC TTGAGCGTCG ATTTTTGTGA TGCTCGTCAG  1800
GGGGGCGGAG CCTATGGAAA AACGCCAGCA ACGCGGCCTT TTTACGGTTC CTGGCCTTTT  1860
GCTGGCCTTT TGCTCACATG TTCTTTCCTG CGTTATCCCC TGATTCTGTG ATAACCGTA   1920
```

*FIG. 7*

```
TTACCGCCTT TGAGTGAGCT GATACCGCTC GCCGCAGCCG AACGACCGAG CGCAGCGAGT 1980
CAGTGAGCGA GGAAGCGGAA GAGCGCCCAA TACGCAAACC GCCTCTCCCC GCGCGTTGGC 2040
CGATTCATTA ATGCAGAATT GATCTCTCAC CTACCAAACA ATGCCCCCCT GCAAAAAATA 2100
AATTCATATA AAAACATAC AGATAACCAT CTGCGGTGAT AAATTATCTC TGGCGGTGTT 2160
GACATAAATA CCACTGGCGG TGATACTGAG CACATCAGCA GGACGCACTG ACCACCATGA 2220
AGGTGACGCT CTTAAAAATT AAGCCCTGAA GAAGGGCAGC ATTCAAAGCA GAAGGCTTTG 2280
GGGTGTGTGA TACGAAACGA AGCATTGGCC GTAAGTGCGA TTCCGGATTA GCTGCCAATG 2340
TGCCAATCGC GGGGGGTTTT CGTTCAGGCA TACAACTGCC ACACACCACC AAAGCTAACT 2400
GACAGGAGAA TCCAGATGGA TGCACAAACA CGCCGCCGCG AACGTCGCGC AGAGAAACAG 2460
GCTCAATGGA AAGCAGCAAA TCCCCTGTTG GTTGGGGTAA GCGCAAAACC AGTTCCGAAA 2520
GATTTTTTTA ACTATAAACG CTGATGGAAG CGTTTATGCG GAAGAGGTAA AGCCCTTCCC 2580
GAGTAACAAA AAACAACAG CATAAATAAC CCCGCTCTTA CACATTCCAG CCCTGAAAAA 2640
GGGCATCAAA TTAAACCACA CCTATGGTGT ATGCATTTAT TTGCATACAT TCAATCAATT 2700
GTTATCTAAG GAAATACTTA CATATGCAAG CTAAACATAA ACAACGTAAA CGTCTGAAAT 2760
CTAGCTGTAA GAGACACCCT TTGTACGTGG ACTTCAGTGA CGTGGGGTGG AATGACTGGA 2820
TTGTGGCTCC CCCGGGGTAT CACGCCTTTT ACTGCCACGG AGAATGCCCT TTTCCTCTGG 2880
CTGATCATCT GAACTCCACT AATCATGCCA TTGTTCAGAC GTTGGTCAAC TCTGTTAACT 2940
CTAAGATTCC TAAGGCATGC TGTGTCCCGA CAGAACTCAG TGCTATCTCG ATGCTGTACC 3000
TTGACGAGAA TGAAAAGGTT GTATTAAAGA ACTATCAGGA CATGGTTGTG GAGGGTTGTG 3060
GGTGTCGCTA GTACAGCAAA ATTAAATACA TAAATATATA TATATATATA TATTTTAGAA 3120
AAAAGAAAAA AATCTAGAGT CGACCTGCAG TAATCGTACA GGGTAGTACA AATAAAAAAG 3180
GCACGTCAGA TGACGTGCCT TTTTTCTTGT GAGCAGTAAG CTTGGCACTG GCCGTCGTTT 3240
TACAACGTCG TGACTGGGAA AACCCTGGCG TTACCCAACT TAATCGCCTT GCAGCACATC 3300
CCCCTTTCGC CAGCTGGCGT AATAGCGAAG AGGCCCGCAC CGATCGCCCT TCCCAACAGT 3360
TGCGCAGCCT GAATGGCGAA TGGCGCCTGA TGCGGTATTT TCTCCTTACG CATCTGTGCG 3420
GTATTTCACA CCGCATATAT GGTGCACTCT CAGTACAATC TGCTCTGATG CCGCATAGTT 3480
AAGCCAGCCC CGACACCCGC CAACACCCGC TGACGCGCCC TGACGGGCTT GTCTGCTCCC 3540
GGCATCCGCT TACAGACAAG CTGTGACCGT CTCCGGGAGC TGCATGTGTC AGAGGTTTTC 3600
ACCGTCATCA CCGAAACGCG CGA                                      3623
```

FIG. 7 (CON'T)

```
          10         20         30         40         50         60         70
AGATCTTGAA AACACCCGGG CCACACACGC CGCGACCTAC AGCTCTTTCT CAGCGTTGGA GTGGAGACGG 80         90        100        110        120        130        140
CGCCCGCAGC GCCCTGCGCG GGTGAGGTCC GCGCAGCTGC TGGGGAAGAG CCCACCTGTC AGGCTGCGCT 150        160        170        180        190        200        210
GGGTCAGCGC AGCAAGTGGG GCTGGCCGCT ATCTCGCTGC ACCCGGCCGC GTCCCGGGCT CCGTGCGCCC 220        230        240        250        260        270        280
TCGCCCCAGC TGGTTTGGAG TTCAACCCTC GGCTCCGCCG CCGGCTCCTT GCGCCTTCGG AGTGTCCCGC 290        300        310        320    (1)         335
AGCGACGCCG GGAGCCGACG CGCCGCGCGG GTACCTAGCC ATG GCT GGG GCG AGC AGG CTG CTC
                                             MET Ala Gly Ala Ser Arg Leu Leu 350              365              380              395
TTT CTG TGG CTG GGC TGC TTC TGC GTG AGC CTG GCG CAG GGA GAG AGA CCG AAG CCA
Phe Leu Trp Leu Gly Cys Phe Cys Val Ser Leu Ala Gln Gly Glu Arg Pro Lys Pro 410              425              440              455
CCT TTC CCG GAG CTC CGC AAA GCT GTG CCA GGT GAC CGC ACG GCA GGT GGT GGC CCG
Pro Phe Pro Glu Leu Arg Lys Ala Val Pro Gly Asp Arg Thr Ala Gly Gly Gly Pro 470              485              500              515
GAC TCC GAG CTG CAG CCG CAA GAC AAG GTC TCT GAA CAC ATG CTG CGG CTC TAT GAC
Asp Ser Glu Leu Gln Pro Gln Asp Lys Val Ser Glu His MET Leu Arg Leu Tyr Asp 530              545              560
AGG TAC AGC ACG GTC CAG GCG GCC CGG ACA CCG GGC TCC CTG GAG GGA GGC TCG CAG
Arg Tyr Ser Thr Val Gln Ala Ala Arg Thr Pro Gly Ser Leu Glu Gly Gly Ser Gln 575              590              605              620
CCC TGG CGC CCT CGG CTC CTG CGC GAA GGC AAC ACG GTT CGC AGC TTT CGG GCG GCA
Pro Trp Arg Pro Arg Leu Leu Arg Glu Gly Asn Thr Val Arg Ser Phe Arg Ala Ala 635              650              665              680
GCA GCA GAA ACT CTT GAA AGA AAA GGA CTG TAT ATC TTC AAT CTG ACA TCG CTA ACC
Ala Ala Glu Thr Leu Glu Arg Lys Gly Leu Tyr Ile Phe Asn Leu Thr Ser Leu Thr 695              710              725              740
AAG TCT GAA AAC ATT TTG TCT GCC ACA CTG TAT TTC TGT ATT GGA GAG CTA GGA AAC
Lys Ser Glu Asn Ile Leu Ser Ala Thr Leu Tyr Phe Cys Ile Gly Glu Leu Gly Asn
```

*FIG. 11*

```
     1430                1445      (377)      1460                1475
TGC GCC AGG AGA TAC CTC AAG GTA GAC TTT GCA GAT ATT GGC TGG AGT GAA TGG ATT
Cys Ala Arg Arg Tyr Leu Lys Val Asp Phe Ala Asp Ile Gly Trp Ser Glu Trp Ile 1490                1505                1520                1535
ATC TCC CCC AAG TCC TTT GAT GCC TAT TAT TGC TCT GGA GCA TGC CAG TTC CCC ATG
Ile Ser Pro Lys Ser Phe Asp Ala Tyr Tyr Cys Ser Gly Ala Cys Gln Phe Pro MET 1550                1565                1580                1595
CCA AAG TCT TTG AAG CCA TCA AAT CAT GCT ACC ATC CAG AGT ATA GTG AGA GCT GTG
Pro Lys Ser Leu Lys Pro Ser Asn His Ala Thr Ile Gln Ser Ile Val Arg Ala Val 1610                1625                1640                1655
GGG GTC GTT CCT GGG ATT CCT GAG CCT TGC TGT GTA CCA GAA AAG ATG TCC TCA CTC
Gly Val Val Pro Gly Ile Pro Glu Pro Cys Cys Val Pro Glu Lys MET Ser Ser Leu 1670                1685                1700
AGT ATT TTA TTC TTT GAT GAA AAT AAG AAT GTA GTG CTT AAA GTA TAC CCT AAC ATG
Ser Ile Leu Phe Phe Asp Glu Asn Lys Asn Val Val Leu Lys Val Tyr Pro Asn MET 1715            1730       (472)    1746       1756       1766       1776
ACA GTA GAG TCT TGC GCT TGC AGA TAACCTGGCA AAGAACTCAT TTGAATGCTT AATTCAATCT
Thr Val Glu Ser Cys Ala Cys Arg

1786
CTAGAGTCGA CGGAATTC
```

FIG. 11 (CON'T)

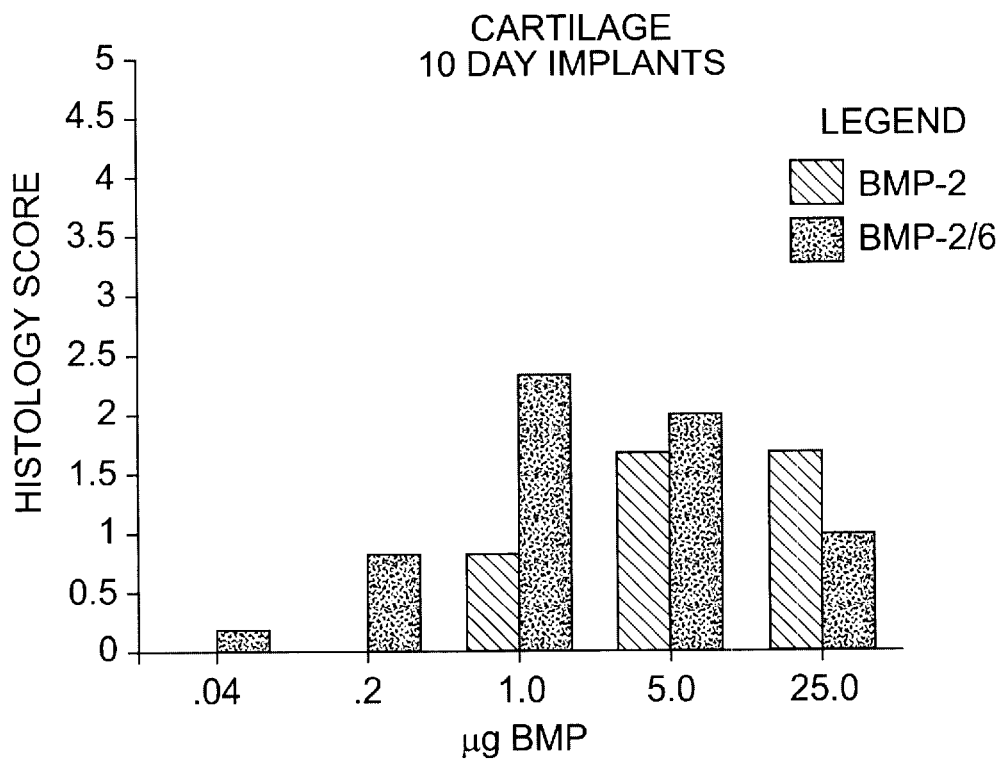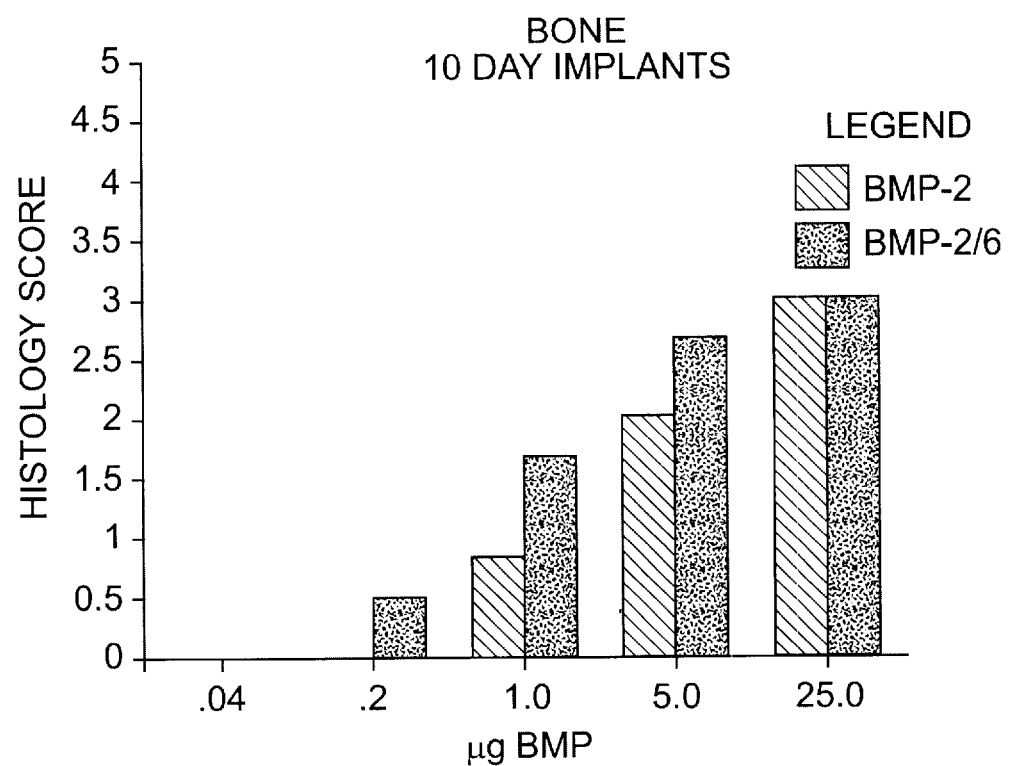
FIG. 13

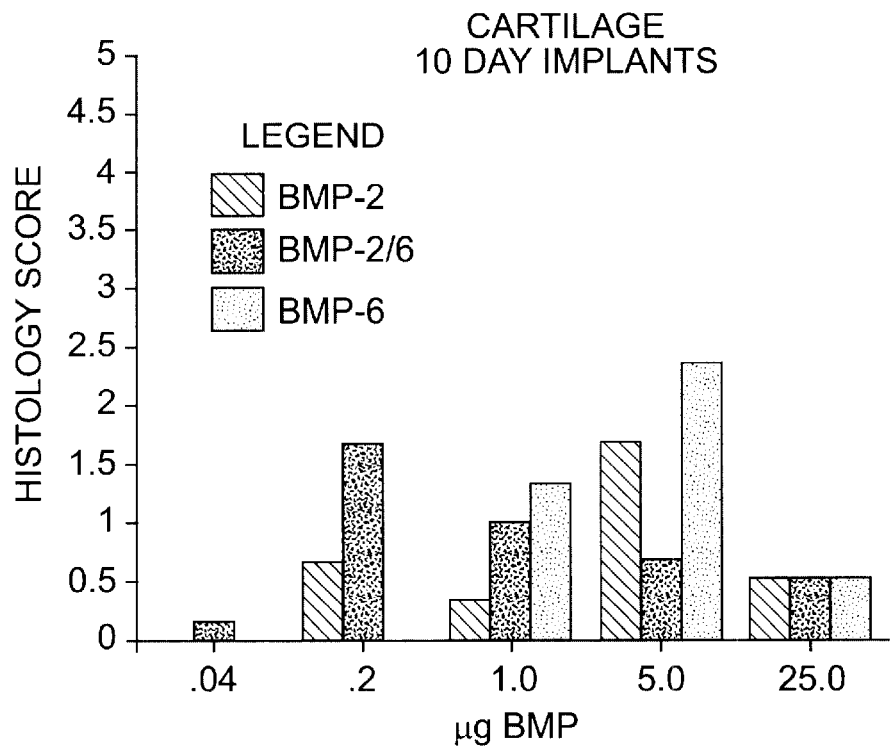
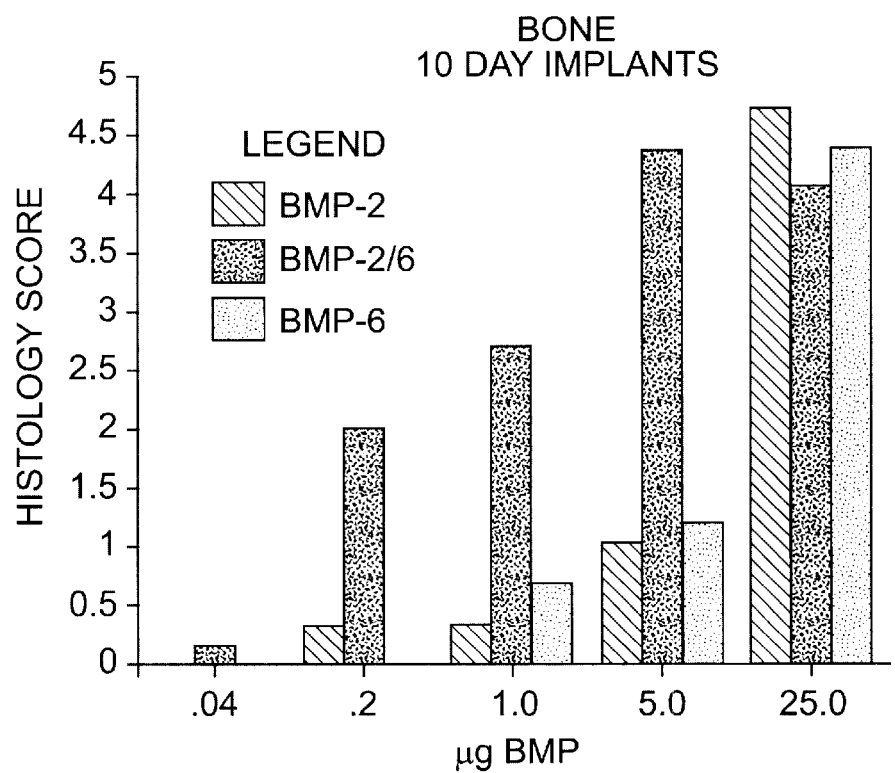
FIG. 14

SEQUENCE LISTING (1) GENERAL INFORMATION:

(iii) NUMBER OF SEQUENCES: 30

(2) INFORMATION FOR SEQ ID NO: 1:

(i) SEQUENCE CHARACTERISTICS:
      (A) LENGTH: 1607 base pairs
      (B) TYPE: nucleic acid
      (C) STRANDEDNESS: double
      (D) TOPOLOGY: unknown (ii) MOLECULE TYPE: DNA (genomic)

(ix) FEATURE:
      (A) NAME/KEY: CDS
      (B) LOCATION: 356..1543

(xi) SEQUENCE DESCRIPTION: SEQ ID NO: 1:

```
GTCGACTCTA GAGTGTGTGT CAGCACTTGG CTGGGGACTT CTTGAACTTG CAGGGAGAAT        60

AACTTGCGCA CCCCACTTTG CGCCGGTGCC TTTGCCCCAG CGGAGCCTGC TTCGCCATCT       120

CCGAGCCCCA CCGCCCCTCC ACTCCTCGGC CTTGCCCGAC ACTGAGACGC TGTTCCCAGC       180

GTGAAAAGAG AGACTGCGCG GCCGGCACCC GGGAGAAGGA GGAGGCAAAG AAAAGGAACG       240

GACATTCGGT CCTTGCGCCA GGTCCTTTGA CCAGAGTTTT TCCATGTGGA CGCTCTTTCA       300

ATGGACGTGT CCCCGCGTGC TTCTTAGACG GACTGCGGTC TCCTAAAGGT CGACC ATG        358
                                                            Met
                                                             1

GTG GCC GGG ACC CGC TGT CTT CTA GCG TTG CTG CTT CCC CAG GTC CTC        406
Val Ala Gly Thr Arg Cys Leu Leu Ala Leu Leu Leu Pro Gln Val Leu
  5                  10                  15
```

```
CTG GGC GGC GCG GCT GGC CTC GTT CCG GAG CTG GGC CGC AGG AAG TTC    454
Leu Gly Gly Ala Ala Gly Leu Val Pro Glu Leu Gly Arg Arg Lys Phe
             20                  25                  30

GCG GCG GCG TCG TCG GGC CGC CCC TCA TCC CAG CCC TCT GAC GAG GTC    502
Ala Ala Ala Ser Ser Gly Arg Pro Ser Ser Gln Pro Ser Asp Glu Val
         35                  40                  45

CTG AGC GAG TTC GAG TTG CGG CTG CTC AGC ATG TTC GGC CTG AAA CAG    550
Leu Ser Glu Phe Glu Leu Arg Leu Leu Ser Met Phe Gly Leu Lys Gln
50                  55                  60                  65

AGA CCC ACC CCC AGC AGG GAC GCC GTG GTG CCC CCC TAC ATG CTA GAC    598
Arg Pro Thr Pro Ser Arg Asp Ala Val Val Pro Pro Tyr Met Leu Asp
                 70                  75                  80

CTG TAT CGC AGG CAC TCA GGT CAG CCG GGC TCA CCC GCC CCA GAC CAC    646
Leu Tyr Arg Arg His Ser Gly Gln Pro Gly Ser Pro Ala Pro Asp His
             85                  90                  95

CGG TTG GAG AGG GCA GCC AGC CGA GCC AAC ACT GTG CGC AGC TTC CAC    694
Arg Leu Glu Arg Ala Ala Ser Arg Ala Asn Thr Val Arg Ser Phe His
         100                 105                 110

CAT GAA GAA TCT TTG GAA GAA CTA CCA GAA ACG AGT GGG AAA ACA ACC    742
His Glu Glu Ser Leu Glu Glu Leu Pro Glu Thr Ser Gly Lys Thr Thr
     115                 120                 125

CGG AGA TTC TTC TTT AAT TTA AGT TCT ATC CCC ACG GAG GAG TTT ATC    790
Arg Arg Phe Phe Phe Asn Leu Ser Ser Ile Pro Thr Glu Glu Phe Ile
130                 135                 140                 145

ACC TCA GCA GAG CTT CAG GTT TTC CGA GAA CAG ATG CAA GAT GCT TTA    838
Thr Ser Ala Glu Leu Gln Val Phe Arg Glu Gln Met Gln Asp Ala Leu
                 150                 155                 160

GGA AAC AAT AGC AGT TTC CAT CAC CGA ATT AAT ATT TAT GAA ATC ATA    886
Gly Asn Asn Ser Ser Phe His His Arg Ile Asn Ile Tyr Glu Ile Ile
             165                 170                 175

AAA CCT GCA ACA GCC AAC TCG AAA TTC CCC GTG ACC AGA CTT TTG GAC    934
Lys Pro Ala Thr Ala Asn Ser Lys Phe Pro Val Thr Arg Leu Leu Asp
         180                 185                 190

ACC AGG TTG GTG AAT CAG AAT GCA AGC AGG TGG GAA ACT TTT GAT GTC    982
Thr Arg Leu Val Asn Gln Asn Ala Ser Arg Trp Glu Thr Phe Asp Val
     195                 200                 205

ACC CCC GCT GTG ATG CGG TGG ACT GCA CAG GGA CAC GCC AAC CAT GGA    1030
Thr Pro Ala Val Met Arg Trp Thr Ala Gln Gly His Ala Asn His Gly
210                 215                 220                 225

TTC GTG GTG GAA GTG GCC CAC TTG GAG GAG AAA CAA GGT GTC TCC AAG    1078
Phe Val Val Glu Val Ala His Leu Glu Glu Lys Gln Gly Val Ser Lys
                 230                 235                 240

AGA CAT GTT AGG ATA AGC AGG TCT TTG CAC CAA GAT GAA CAC AGC TGG    1126
Arg His Val Arg Ile Ser Arg Ser Leu His Gln Asp Glu His Ser Trp
             245                 250                 255

TCA CAG ATA AGG CCA TTG CTA GTA ACT TTT GGC CAT GAT GGA AAA GGG    1174
Ser Gln Ile Arg Pro Leu Leu Val Thr Phe Gly His Asp Gly Lys Gly
         260                 265                 270

CAT CCT CTC CAC AAA AGA GAA AAA CGT CAA GCC AAA CAC AAA CAG CGG    1222
His Pro Leu His Lys Arg Glu Lys Arg Gln Ala Lys His Lys Gln Arg
     275                 280                 285

AAA CGC CTT AAG TCC AGC TGT AAG AGA CAC CCT TTG TAC GTG GAC TTC    1270
Lys Arg Leu Lys Ser Ser Cys Lys Arg His Pro Leu Tyr Val Asp Phe
290                 295                 300                 305

AGT GAC GTG GGG TGG AAT GAC TGG ATT GTG GCT CCC CCG GGG TAT CAC    1318
Ser Asp Val Gly Trp Asn Asp Trp Ile Val Ala Pro Pro Gly Tyr His
                 310                 315                 320

GCC TTT TAC TGC CAC GGA GAA TGC CCT TTT CCT CTG GCT GAT CAT CTG    1366
Ala Phe Tyr Cys His Gly Glu Cys Pro Phe Pro Leu Ala Asp His Leu
```

```
                     325                 330                 335
AAC TCC ACT AAT CAT GCC ATT GTT CAG ACG TTG GTC AAC TCT GTT AAC       1414
Asn Ser Thr Asn His Ala Ile Val Gln Thr Leu Val Asn Ser Val Asn
            340                 345                 350

TCT AAG ATT CCT AAG GCA TGC TGT GTC CCG ACA GAA CTC AGT GCT ATC       1462
Ser Lys Ile Pro Lys Ala Cys Cys Val Pro Thr Glu Leu Ser Ala Ile
355                 360                 365

TCG ATG CTG TAC CTT GAC GAG AAT GAA AAG GTT GTA TTA AAG AAC TAT       1510
Ser Met Leu Tyr Leu Asp Glu Asn Glu Lys Val Val Leu Lys Asn Tyr
370                 375                 380                 385

CAG GAC ATG GTT GTG GAG GGT TGT GGG TGT CGC TAGTACAGCA AAATTAAA       1563
Gln Asp Met Val Val Glu Gly Cys Gly Cys Arg
                390                 395

CATAAATATA TATATATA TATATTTTAG AAAAAAGAAA AAAA                        1607

(2) INFORMATION FOR SEQ ID NO: 2:

(i) SEQUENCE CHARACTERISTICS:
        (A) LENGTH: 396 amino acids
        (B) TYPE: amino acid
        (D) TOPOLOGY: linear (ii) MOLECULE TYPE: protein (xi) SEQUENCE DESCRIPTION: SEQ ID NO: 2:

Met Val Ala Gly Thr Arg Cys Leu Leu Ala Leu Leu Leu Pro Gln Val
 1               5                  10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Thr Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255
```

```
Trp Ser Gln Ile Arg Pro Leu Leu Val Thr Phe Gly His Asp Gly Lys
        260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
        290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
                340                 345                 350

Asn Ser Lys Ile Pro Lys Ala Cys Cys Val Pro Thr Glu Leu Ser Ala
                355                 360                 365

Ile Ser Met Leu Tyr Leu Asp Glu Asn Glu Lys Val Val Leu Lys Asn
        370                 375                 380

Tyr Gln Asp Met Val Val Glu Gly Cys Gly Cys Arg
385                 390                 395

(2) INFORMATION FOR SEQ ID NO: 3:

(i) SEQUENCE CHARACTERISTICS:
        (A) LENGTH: 1954 base pairs
        (B) TYPE: nucleic acid
        (C) STRANDEDNESS: double
        (D) TOPOLOGY: unknown (ii) MOLECULE TYPE: DNA (genomic)

(ix) FEATURE:
        (A) NAME/KEY: CDS
        (B) LOCATION: 403..1626

(xi) SEQUENCE DESCRIPTION: SEQ ID NO: 3:

CTCTAGAGGG CAGAGGAGGA GGGAGGGAGG GAAGGAGCGC GGAGCCCGGC CCGGAAGCTA      60

GGTGAGTGTG CATCCGAGC TGAGGGACGC GAGCCTGAGA CGCCGCTGCT GCTCCGGCTG     120

AGTATCTAGC TTGTCTCCCC GATGGGATTC CCGTCCAAGC TATCTCGAGC CTGCAGCGCC    180

ACAGTCCCCG GCCCTCGCCC AGGTTCACTG CAACCGTTCA GAGGTCCCCA GGAGCTGCTG    240

CTGGCGAGCC CGCTACTGCA GGACCTATG GAGCCATTCC GTAGTGCCAT CCCGAGCAAC     300

GCACTGCTGC AGCTTCCCTG AGCCTTTCCA GCAAGTTTGT TCAAGATTGG CTGTCAAGAA    360

TCATGGACTG TTATTATATG CCTTGTTTTC TGTCAAGACA CC ATG ATT CCT GGT      414
                                                Met Ile Pro Gly
                                                 1

AAC CGA ATG CTG ATG GTC GTT TTA TTA TGC CAA GTC CTG CTA GGA GGC     462
Asn Arg Met Leu Met Val Val Leu Leu Cys Gln Val Leu Leu Gly Gly
 5                  10                  15                  20

GCG AGC CAT GCT AGT TTG ATA CCT GAG ACG GGG AAG AAA AAA GTC GCC     510
Ala Ser His Ala Ser Leu Ile Pro Glu Thr Gly Lys Lys Lys Val Ala
                25                  30                  35

GAG ATT CAG GGC CAC GCG GGA GGA CGC CGC TCA GGG CAG AGC CAT GAG     558
Glu Ile Gln Gly His Ala Gly Gly Arg Arg Ser Gly Gln Ser His Glu
            40                  45                  50

CTC CTG CGG GAC TTC GAG GCG ACA CTT CTG CAG ATG TTT GGG CTG CGC     606
Leu Leu Arg Asp Phe Glu Ala Thr Leu Leu Gln Met Phe Gly Leu Arg
        55                  60                  65

CGC CGC CCG CAG CCT AGC AAG AGT GCC GTC ATT CCG GAC TAC ATG CGG     654
Arg Arg Pro Gln Pro Ser Lys Ser Ala Val Ile Pro Asp Tyr Met Arg
```

```
              70                  75                  80
GAT CTT TAC CGG CTT CAG TCT GGG GAG GAG GAG GAA GAG CAG ATC CAC         702
Asp Leu Tyr Arg Leu Gln Ser Gly Glu Glu Glu Glu Glu Gln Ile His
 85                  90                  95                 100

AGC ACT GGT CTT GAG TAT CCT GAG CGC CCG GCC AGC CGG GCC AAC ACC         750
Ser Thr Gly Leu Glu Tyr Pro Glu Arg Pro Ala Ser Arg Ala Asn Thr
                    105                 110                 115

GTG AGG AGC TTC CAC CAC GAA GAA CAT CTG GAG AAC ATC CCA GGG ACC         798
Val Arg Ser Phe His His Glu Glu His Leu Glu Asn Ile Pro Gly Thr
                120                 125                 130

AGT GAA AAC TCT GCT TTT CGT TTC CTC TTT AAC CTC AGC AGC ATC CCT         846
Ser Glu Asn Ser Ala Phe Arg Phe Leu Phe Asn Leu Ser Ser Ile Pro
            135                 140                 145

GAG AAC GAG GTG ATC TCC TCT GCA GAG CTT CGG CTC TTC CGG GAG CAG         894
Glu Asn Glu Val Ile Ser Ser Ala Glu Leu Arg Leu Phe Arg Glu Gln
        150                 155                 160

GTG GAC CAG GGC CCT GAT TGG GAA AGG GGC TTC CAC CGT ATA AAC ATT         942
Val Asp Gln Gly Pro Asp Trp Glu Arg Gly Phe His Arg Ile Asn Ile
165                 170                 175                 180

TAT GAG GTT ATG AAG CCC CCA GCA GAA GTG GTG CCT GGG CAC CTC ATC         990
Tyr Glu Val Met Lys Pro Pro Ala Glu Val Val Pro Gly His Leu Ile
                185                 190                 195

ACA CGA CTA CTG GAC ACG AGA CTG GTC CAC CAC AAT GTG ACA CGG TGG        1038
Thr Arg Leu Leu Asp Thr Arg Leu Val His His Asn Val Thr Arg Trp
                200                 205                 210

GAA ACT TTT GAT GTG AGC CCT GCG GTC CTT CGC TGG ACC CGG GAG AAG        1086
Glu Thr Phe Asp Val Ser Pro Ala Val Leu Arg Trp Thr Arg Glu Lys
            215                 220                 225

CAG CCA AAC TAT GGG CTA GCC ATT GAG GTG ACT CAC CTC CAT CAG ACT        1134
Gln Pro Asn Tyr Gly Leu Ala Ile Glu Val Thr His Leu His Gln Thr
        230                 235                 240

CGG ACC CAC CAG GGC CAG CAT GTC AGG ATT AGC CGA TCG TTA CCT CAA        1182
Arg Thr His Gln Gly Gln His Val Arg Ile Ser Arg Ser Leu Pro Gln
245                 250                 255                 260

GGG AGT GGG AAT TGG GCC CAG CTC CGG CCC CTC CTG GTC ACC TTT GGC        1230
Gly Ser Gly Asn Trp Ala Gln Leu Arg Pro Leu Leu Val Thr Phe Gly
                265                 270                 275

CAT GAT GGC CGG GGC CAT GCC TTG ACC CGA CGC CGG AGG GCC AAG CGT        1278
His Asp Gly Arg Gly His Ala Leu Thr Arg Arg Arg Arg Ala Lys Arg
                280                 285                 290

AGC CCT AAG CAT CAC TCA CAG CGG GCC AGG AAG AAG AAT AAG AAC TGC        1326
Ser Pro Lys His His Ser Gln Arg Ala Arg Lys Lys Asn Lys Asn Cys
            295                 300                 305

CGG CGC CAC TCG CTC TAT GTG GAC TTC AGC GAT GTG GGC TGG AAT GAC        1374
Arg Arg His Ser Leu Tyr Val Asp Phe Ser Asp Val Gly Trp Asn Asp
        310                 315                 320

TGG ATT GTG GCC CCA CCA GGC TAC CAG GCC TTC TAC TGC CAT GGG GAC        1422
Trp Ile Val Ala Pro Pro Gly Tyr Gln Ala Phe Tyr Cys His Gly Asp
325                 330                 335                 340

TGC CCC TTT CCA CTG GCT GAC CAC CTC AAC TCA ACC AAC CAT GCC ATT        1470
Cys Pro Phe Pro Leu Ala Asp His Leu Asn Ser Thr Asn His Ala Ile
                345                 350                 355

GTG CAG ACC CTG GTC AAT TCT GTC AAT TCC AGT ATC CCC AAA GCC TGT        1518
Val Gln Thr Leu Val Asn Ser Val Asn Ser Ser Ile Pro Lys Ala Cys
                360                 365                 370

TGT GTG CCC ACT GAA CTG AGT GCC ATC TCC ATG CTG TAC CTG GAT GAG        1566
Cys Val Pro Thr Glu Leu Ser Ala Ile Ser Met Leu Tyr Leu Asp Glu
            375                 380                 385

TAT GAT AAG GTG GTA CTG AAA AAT TAT CAG GAG ATG GTA GTA GAG GGA        1614
```

```
Tyr Asp Lys Val Val Leu Lys Asn Tyr Gln Glu Met Val Val Glu Gly
    390                 395                 400

TGT GGG TGC CGC TGAGATCAGG CAGTCCTTGA GGATAGACAG ATATACACAC         1666
Cys Gly Cys Arg
405

CACACACACA CACCACATAC ACCACACACA CACGTTCCCA TCCACTCACC CACACACTAC   1726

ACAGACTGCT TCCTTATAGC TGGACTTTTA TTTAAAAAAA AAAAAAAAAA AATGGAAAAA   1786

ATCCCTAAAC ATTCACCTTG ACCTTATTTA TGACTTTACG TGCAAATGTT TTGACCATAT   1846

TGATCATATA TTTTGACAAA ATATATTTAT AACTACGTAT TAAAAGAAAA AAATAAAATG   1906

AGTCATTATT TTAAAAAAAA AAAAAAAACT CTAGAGTCGA CGGAATTC               1954

(2) INFORMATION FOR SEQ ID NO: 4:

(i) SEQUENCE CHARACTERISTICS:
        (A) LENGTH: 408 amino acids
        (B) TYPE: amino acid
        (D) TOPOLOGY: linear (ii) MOLECULE TYPE: protein (xi) SEQUENCE DESCRIPTION: SEQ ID NO: 4:

Met Ile Pro Gly Asn Arg Met Leu Met Val Val Leu Leu Cys Gln Val
 1               5                  10                  15

Leu Leu Gly Gly Ala Ser His Ala Ser Leu Ile Pro Glu Thr Gly Lys
                20                  25                  30

Lys Lys Val Ala Glu Ile Gln Gly His Ala Gly Gly Arg Arg Ser Gly
            35                  40                  45

Gln Ser His Glu Leu Leu Arg Asp Phe Glu Ala Thr Leu Leu Gln Met
        50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                85                  90                  95

Glu Gln Ile His Ser Thr Gly Leu Glu Tyr Pro Glu Arg Pro Ala Ser
            100                 105                 110

Arg Ala Asn Thr Val Arg Ser Phe His His Glu Glu His Leu Glu Asn
        115                 120                 125

Ile Pro Gly Thr Ser Glu Asn Ser Ala Phe Arg Phe Leu Phe Asn Leu
130                 135                 140

Ser Ser Ile Pro Glu Asn Glu Val Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
            180                 185                 190

Gly His Leu Ile Thr Arg Leu Leu Asp Thr Arg Leu Val His His Asn
        195                 200                 205

Val Thr Arg Trp Glu Thr Phe Asp Val Ser Pro Ala Val Leu Arg Trp
210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
            260                 265                 270
```

```
Val Thr Phe Gly His Asp Gly Arg Gly His Ala Leu Thr Arg Arg Arg
        275                 280                 285

Arg Ala Lys Arg Ser Pro Lys His His Ser Gln Arg Ala Arg Lys Lys
        290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
                340                 345                 350

Asn His Ala Ile Val Gln Thr Leu Val Asn Ser Val Asn Ser Ser Ile
        355                 360                 365

Pro Lys Ala Cys Cys Val Pro Thr Glu Leu Ser Ala Ile Ser Met Leu
370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
                405
```

(2) INFORMATION FOR SEQ ID NO: 5:

(i) SEQUENCE CHARACTERISTICS:
        (A) LENGTH: 1448 base pairs
        (B) TYPE: nucleic acid
        (C) STRANDEDNESS: double
        (D) TOPOLOGY: unknown (ii) MOLECULE TYPE: DNA (genomic)

(ix) FEATURE:
        (A) NAME/KEY: CDS
        (B) LOCATION: 97..1389

(xi) SEQUENCE DESCRIPTION: SEQ ID NO: 5:

```
GTGACCGAGC GGCGCGGACG GCCGCCTGCC CCCTCTGCCA CCTGGGGCGG TGCGGGCCCG        60

GAGCCCGGAG CCCGGGTAGC GCGTAGAGCC GGCGCG ATG CAC GTG CGC TCA CTG        114
                                       Met His Val Arg Ser Leu
                                         1               5

CGA GCT GCG GCG CCG CAC AGC TTC GTG GCG CTC TGG GCA CCC CTG TTC        162
Arg Ala Ala Ala Pro His Ser Phe Val Ala Leu Trp Ala Pro Leu Phe
             10                  15                  20

CTG CTG CGC TCC GCC CTG GCC GAC TTC AGC CTG GAC AAC GAG GTG CAC        210
Leu Leu Arg Ser Ala Leu Ala Asp Phe Ser Leu Asp Asn Glu Val His
         25                  30                  35

TCG AGC TTC ATC CAC CGG CGC CTC CGC AGC CAG GAG CGG CGG GAG ATG        258
Ser Ser Phe Ile His Arg Arg Leu Arg Ser Gln Glu Arg Arg Glu Met
     40                  45                  50

CAG CGC GAG ATC CTC TCC ATT TTG GGC TTG CCC CAC CGC CCG CGC CCG        306
Gln Arg Glu Ile Leu Ser Ile Leu Gly Leu Pro His Arg Pro Arg Pro
 55                  60                  65                  70

CAC CTC CAG GGC AAG CAC AAC TCG GCA CCC ATG TTC ATG CTG GAC CTG        354
His Leu Gln Gly Lys His Asn Ser Ala Pro Met Phe Met Leu Asp Leu
                 75                  80                  85

TAC AAC GCC ATG GCG GTG GAG GAG GGC GGC GGG CCC GGC GGC CAG GGC        402
Tyr Asn Ala Met Ala Val Glu Glu Gly Gly Gly Pro Gly Gly Gln Gly
             90                  95                 100

TTC TCC TAC CCC TAC AAG GCC GTC TTC AGT ACC CAG GGC CCC CCT CTG        450
Phe Ser Tyr Pro Tyr Lys Ala Val Phe Ser Thr Gln Gly Pro Pro Leu
        105                 110                 115
```

```
                                                         -continued

GCC AGC CTG CAA GAT AGC CAT TTC CTC ACC GAC GCC GAC ATG GTC ATG        498
Ala Ser Leu Gln Asp Ser His Phe Leu Thr Asp Ala Asp Met Val Met
    120                 125                 130

AGC TTC GTC AAC CTC GTG GAA CAT GAC AAG GAA TTC TTC CAC CCA CGC        546
Ser Phe Val Asn Leu Val Glu His Asp Lys Glu Phe Phe His Pro Arg
135                 140                 145                 150

TAC CAC CAT CGA GAG TTC CGG TTT GAT CTT TCC AAG ATC CCA GAA GGG        594
Tyr His His Arg Glu Phe Arg Phe Asp Leu Ser Lys Ile Pro Glu Gly
                155                 160                 165

GAA GCT GTC ACG GCA GCC GAA TTC CGG ATC TAC AAG GAC TAC ATC CGG        642
Glu Ala Val Thr Ala Ala Glu Phe Arg Ile Tyr Lys Asp Tyr Ile Arg
        170                 175                 180

GAA CGC TTC GAC AAT GAG ACG TTC CGG ATC AGC GTT TAT CAG GTG CTC        690
Glu Arg Phe Asp Asn Glu Thr Phe Arg Ile Ser Val Tyr Gln Val Leu
            185                 190                 195

CAG GAG CAC TTG GGC AGG GAA TCG GAT CTC TTC CTG CTC GAC AGC CGT        738
Gln Glu His Leu Gly Arg Glu Ser Asp Leu Phe Leu Leu Asp Ser Arg
200                 205                 210

ACC CTC TGG GCC TCG GAG GAG GGC TGG CTG GTG TTT GAC ATC ACA GCC        786
Thr Leu Trp Ala Ser Glu Glu Gly Trp Leu Val Phe Asp Ile Thr Ala
215                 220                 225                 230

ACC AGC AAC CAC TGG GTG GTC AAT CCG CGG CAC AAC CTG GGC CTG CAG        834
Thr Ser Asn His Trp Val Val Asn Pro Arg His Asn Leu Gly Leu Gln
                235                 240                 245

CTC TCG GTG GAG ACG CTG GAT GGG CAG AGC ATC AAC CCC AAG TTG GCG        882
Leu Ser Val Glu Thr Leu Asp Gly Gln Ser Ile Asn Pro Lys Leu Ala
        250                 255                 260

GGC CTG ATT GGG CGG CAC GGG CCC CAG AAC AAG CAG CCC TTC ATG GTG        930
Gly Leu Ile Gly Arg His Gly Pro Gln Asn Lys Gln Pro Phe Met Val
            265                 270                 275

GCT TTC TTC AAG GCC ACG GAG GTC CAC TTC CGC AGC ATC CGG TCC ACG        978
Ala Phe Phe Lys Ala Thr Glu Val His Phe Arg Ser Ile Arg Ser Thr
280                 285                 290

GGG AGC AAA CAG CGC AGC CAG AAC CGC TCC AAG ACG CCC AAG AAC CAG       1026
Gly Ser Lys Gln Arg Ser Gln Asn Arg Ser Lys Thr Pro Lys Asn Gln
295                 300                 305                 310

GAA GCC CTG CGG ATG GCC AAC GTG GCA GAG AAC AGC AGC AGC GAC CAG       1074
Glu Ala Leu Arg Met Ala Asn Val Ala Glu Asn Ser Ser Ser Asp Gln
                315                 320                 325

AGG CAG GCC TGT AAG AAG CAC GAG CTG TAT GTC AGC TTC CGA GAC CTG       1122
Arg Gln Ala Cys Lys Lys His Glu Leu Tyr Val Ser Phe Arg Asp Leu
        330                 335                 340

GGC TGG CAG GAC TGG ATC ATC GCG CCT GAA GGC TAC GCC GCC TAC TAC       1170
Gly Trp Gln Asp Trp Ile Ile Ala Pro Glu Gly Tyr Ala Ala Tyr Tyr
            345                 350                 355

TGT GAG GGG GAG TGT GCC TTC CCT CTG AAC TCC TAC ATG AAC GCC ACC       1218
Cys Glu Gly Glu Cys Ala Phe Pro Leu Asn Ser Tyr Met Asn Ala Thr
360                 365                 370

AAC CAC GCC ATC GTG CAG ACG CTG GTC CAC TTC ATC AAC CCG GAA ACG       1266
Asn His Ala Ile Val Gln Thr Leu Val His Phe Ile Asn Pro Glu Thr
375                 380                 385                 390

GTG CCC AAG CCC TGC TGT GCG CCC ACG CAG CTC AAT GCC ATC TCC GTC       1314
Val Pro Lys Pro Cys Cys Ala Pro Thr Gln Leu Asn Ala Ile Ser Val
                395                 400                 405

CTC TAC TTC GAT GAC AGC TCC AAC GTC ATC CTG AAG AAA TAC AGA AAC       1362
Leu Tyr Phe Asp Asp Ser Ser Asn Val Ile Leu Lys Lys Tyr Arg Asn
        410                 415                 420

ATG GTG GTC CGG GCC TGT GGC TGC CAC TAGCTCCTCC GAGAATTCAG            1409
Met Val Val Arg Ala Cys Gly Cys His
425                 430
```

ACCCTTTGGG GCCAAGTTTT TCTGGATCCT CCATTGCTC     1448

(2) INFORMATION FOR SEQ ID NO: 6:

(i) SEQUENCE CHARACTERISTICS:
        (A) LENGTH: 431 amino acids
        (B) TYPE: amino acid
        (D) TOPOLOGY: linear (ii) MOLECULE TYPE: protein (xi) SEQUENCE DESCRIPTION: SEQ ID NO: 6:

```
Met His Val Arg Ser Leu Arg Ala Ala Ala Pro His Ser Phe Val Ala
 1               5                  10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
        50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
               100                 105                 110

Thr Gln Gly Pro Pro Leu Ala Ser Leu Gln Asp Ser His Phe Leu Thr
            115                 120                 125

Asp Ala Asp Met Val Met Ser Phe Val Asn Leu Val Glu His Asp Lys
        130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
```

```
                340                 345                 350
Gly Tyr Ala Ala Tyr Tyr Cys Glu Gly Glu Cys Ala Phe Pro Leu Asn
            355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430
```

(2) INFORMATION FOR SEQ ID NO: 7:

(i) SEQUENCE CHARACTERISTICS:
        (A) LENGTH: 2923 base pairs
        (B) TYPE: nucleic acid
        (C) STRANDEDNESS: double
        (D) TOPOLOGY: circular (ii) MOLECULE TYPE: cDNA to mRNA (iii) HYPOTHETICAL: NO (vi) ORIGINAL SOURCE:
        (A) ORGANISM: Homo sapiens
        (F) TISSUE TYPE: Human placenta (vii) IMMEDIATE SOURCE:
        (A) LIBRARY: Stratagene catalog #936203 Human placenta
            cDNA library
        (B) CLONE: BMP6C35

(viii) POSITION IN GENOME:
        (C) UNITS: bp (ix) FEATURE:
        (A) NAME/KEY: CDS
        (B) LOCATION: 160..1701

(ix) FEATURE:
        (A) NAME/KEY: mat_peptide
        (B) LOCATION: 1282..1698

(ix) FEATURE:
        (A) NAME/KEY: mRNA
        (B) LOCATION: 1..2923

(xi) SEQUENCE DESCRIPTION: SEQ ID NO: 7:

```
CGACCATGAG AGATAAGGAC TGAGGGCCAG GAAGGGGAAG CGAGCCCGCC GAGAGGTGGC      60

GGGGACTGCT CACGCCAAGG GCCACAGCGG CCGCGCTCCG GCCTCGCTCC GCCGCTCCAC     120

GCCTCGCGGG ATCCGCGGGG GCAGCCCGGC CGGGCGGGG ATG CCG GGG CTG GGG       174
                                           Met Pro Gly Leu Gly
                                           -374            -370

CGG AGG GCG CAG TGG CTG TGC TGG TGG TGG GGG CTG CTG TGC AGC TGC       222
Arg Arg Ala Gln Trp Leu Cys Trp Trp Trp Gly Leu Leu Cys Ser Cys
            -365                 -360                 -355

TGC GGG CCC CCG CCG CTG CGG CCG CCC TTG CCC GCT GCC GCG GCC GCC       270
Cys Gly Pro Pro Pro Leu Arg Pro Pro Leu Pro Ala Ala Ala Ala Ala
            -350                 -345                 -340

GCC GCC GGG GGG CAG CTG CTG GGG GAC GGC GGG AGC CCC GGC CGC ACG       318
Ala Ala Gly Gly Gln Leu Leu Gly Asp Gly Gly Ser Pro Gly Arg Thr
            -335                 -330                 -325

GAG CAG CCG CCG CCG TCG CCG CAG TCC TCC TCG GGC TTC CTG TAC CGG       366
Glu Gln Pro Pro Pro Ser Pro Gln Ser Ser Ser Gly Phe Leu Tyr Arg
        -320                 -315                 -310
```

-continued

```
CGG CTC AAG ACG CAG GAG AAG CGG GAG ATG CAG AAG GAG ATC TTG TCG      414
Arg Leu Lys Thr Gln Glu Lys Arg Glu Met Gln Lys Glu Ile Leu Ser
-305             -300            -295            -290

GTG CTG GGG CTC CCG CAC CGG CCC CGG CCC CTG CAC GGC CTC CAA CAG      462
Val Leu Gly Leu Pro His Arg Pro Arg Pro Leu His Gly Leu Gln Gln
        -285            -280            -275

CCG CAG CCC CCG GCG CTC CGG CAG CAG GAG GAG CAG CAG CAG CAG CAG      510
Pro Gln Pro Pro Ala Leu Arg Gln Gln Glu Glu Gln Gln Gln Gln Gln
        -270            -265            -260

CAG CTG CCT CGC GGA GAG CCC CCT CCC GGG CGA CTG AAG TCC GCG CCC      558
Gln Leu Pro Arg Gly Glu Pro Pro Pro Gly Arg Leu Lys Ser Ala Pro
        -255            -250            -245

CTC TTC ATG CTG GAT CTG TAC AAC GCC CTG TCC GCC GAC AAC GAC GAG      606
Leu Phe Met Leu Asp Leu Tyr Asn Ala Leu Ser Ala Asp Asn Asp Glu
        -240            -235            -230

GAC GGG GCG TCG GAG GGG GAG AGG CAG CAG TCC TGG CCC CAC GAA GCA      654
Asp Gly Ala Ser Glu Gly Glu Arg Gln Gln Ser Trp Pro His Glu Ala
-225            -220            -215            -210

GCC AGC TCG TCC CAG CGT CGG CAG CCG CCC CCG GGC GCC GCG CAC CCG      702
Ala Ser Ser Ser Gln Arg Arg Gln Pro Pro Pro Gly Ala Ala His Pro
        -205            -200            -195

CTC AAC CGC AAG AGC CTT CTG GCC CCC GGA TCT GGC AGC GGC GGC GCG      750
Leu Asn Arg Lys Ser Leu Leu Ala Pro Gly Ser Gly Ser Gly Gly Ala
        -190            -185            -180

TCC CCA CTG ACC AGC GCG CAG GAC AGC GCC TTC CTC AAC GAC GCG GAC      798
Ser Pro Leu Thr Ser Ala Gln Asp Ser Ala Phe Leu Asn Asp Ala Asp
        -175            -170            -165

ATG GTC ATG AGC TTT GTG AAC CTG GTG GAG TAC GAC AAG GAG TTC TCC      846
Met Val Met Ser Phe Val Asn Leu Val Glu Tyr Asp Lys Glu Phe Ser
        -160            -155            -150

CCT CGT CAG CGA CAC CAC AAA GAG TTC AAG TTC AAC TTA TCC CAG ATT      894
Pro Arg Gln Arg His His Lys Glu Phe Lys Phe Asn Leu Ser Gln Ile
-145            -140            -135            -130

CCT GAG GGT GAG GTG GTG ACG GCT GCA GAA TTC CGC ATC TAC AAG GAC      942
Pro Glu Gly Glu Val Val Thr Ala Ala Glu Phe Arg Ile Tyr Lys Asp
        -125            -120            -115

TGT GTT ATG GGG AGT TTT AAA AAC CAA ACT TTT CTT ATC AGC ATT TAT      990
Cys Val Met Gly Ser Phe Lys Asn Gln Thr Phe Leu Ile Ser Ile Tyr
        -110            -105            -100

CAA GTC TTA CAG GAG CAT CAG CAC AGA GAC TCT GAC CTG TTT TTG TTG     1038
Gln Val Leu Gln Glu His Gln His Arg Asp Ser Asp Leu Phe Leu Leu
        -95             -90             -85

GAC ACC CGT GTA GTA TGG GCC TCA GAA GAA GGC TGG CTG GAA TTT GAC     1086
Asp Thr Arg Val Val Trp Ala Ser Glu Glu Gly Trp Leu Glu Phe Asp
-80             -75             -70

ATC ACG GCC ACT AGC AAT CTG TGG GTT GTG ACT CCA CAG CAT AAC ATG     1134
Ile Thr Ala Thr Ser Asn Leu Trp Val Val Thr Pro Gln His Asn Met
-65             -60             -55             -50

GGG CTT CAG CTG AGC GTG GTG ACA AGG GAT GGA GTC CAC GTC CAC CCC     1182
Gly Leu Gln Leu Ser Val Val Thr Arg Asp Gly Val His Val His Pro
        -45             -40             -35

CGA GCC GCA GGC CTG GTG GGC AGA GAC GGC CCT TAC GAT AAG CAG CCC     1230
Arg Ala Ala Gly Leu Val Gly Arg Asp Gly Pro Tyr Asp Lys Gln Pro
        -30             -25             -20

TTC ATG GTG GCT TTC TTC AAA GTG AGT GAG GTC CAC GTG CGC ACC ACC     1278
Phe Met Val Ala Phe Phe Lys Val Ser Glu Val His Val Arg Thr Thr
        -15             -10             -5

AGG TCA GCC TCC AGC CGG CGC CGA CAA CAG AGT CGT AAT CGC TCT ACC     1326
Arg Ser Ala Ser Ser Arg Arg Arg Gln Gln Ser Arg Asn Arg Ser Thr
```

```
                1               5                    10                        15
CAG TCC CAG GAC GTG GCG CGG GTC TCC AGT GCT TCA GAT TAC AAC AGC           1374
Gln Ser Gln Asp Val Ala Arg Val Ser Ser Ala Ser Asp Tyr Asn Ser
                        20                  25                  30

AGT GAA TTG AAA ACA GCC TGC AGG AAG CAT GAG CTG TAT GTG AGT TTC           1422
Ser Glu Leu Lys Thr Ala Cys Arg Lys His Glu Leu Tyr Val Ser Phe
                35                  40                  45

CAA GAC CTG GGA TGG CAG GAC TGG ATC ATT GCA CCC AAG GGC TAT GCT           1470
Gln Asp Leu Gly Trp Gln Asp Trp Ile Ile Ala Pro Lys Gly Tyr Ala
            50                  55                  60

GCC AAT TAC TGT GAT GGA GAA TGC TCC TTC CCA CTC AAC GCA CAC ATG           1518
Ala Asn Tyr Cys Asp Gly Glu Cys Ser Phe Pro Leu Asn Ala His Met
        65                  70                  75

AAT GCA ACC AAC CAC GCG ATT GTG CAG ACC TTG GTT CAC CTT ATG AAC           1566
Asn Ala Thr Asn His Ala Ile Val Gln Thr Leu Val His Leu Met Asn
80                  85                  90                  95

CCC GAG TAT GTC CCC AAA CCG TGC TGT GCG CCA ACT AAG CTA AAT GCC           1614
Pro Glu Tyr Val Pro Lys Pro Cys Cys Ala Pro Thr Lys Leu Asn Ala
                100                 105                 110

ATC TCG GTT CTT TAC TTT GAT GAC AAC TCC AAT GTC ATT CTG AAA AAA           1662
Ile Ser Val Leu Tyr Phe Asp Asp Asn Ser Asn Val Ile Leu Lys Lys
            115                 120                 125

TAC AGG AAT ATG GTT GTA AGA GCT TGT GGA TGC CAC TAACTCGAAA                1708
Tyr Arg Asn Met Val Val Arg Ala Cys Gly Cys His
        130                 135                 140

CCAGATGCTG GGGACACACA TTCTGCCTTG GATTCCTAGA TTACATCTGC CTTAAAAAAA         1768

CACGGAAGCA CAGTTGGAGG TGGGACGATG AGACTTTGAA ACTATCTCAT GCCAGTGCCT         1828

TATTACCCAG GAAGATTTTA AAGGACCTCA TTAATAATTT GCTCACTTGG TAAATGACGT         1888

GAGTAGTTGT TGGTCTGTAG CAAGCTGAGT TTGGATGTCT GTAGCATAAG GTCTGGTAAC         1948

TGCAGAAACA TAACCGTGAA GCTCTTCCTA CCCTCCTCCC CCAAAAACCC ACCAAAATTA         2008

GTTTTAGCTG TAGATCAAGC TATTTGGGGT GTTTGTTAGT AAATAGGGAA ATAATCTCA          2068

AAGGAGTTAA ATGTATTCTT GGCTAAAGGA TCAGCTGGTT CAGTACTGTC TATCAAAGGT         2128

AGATTTTACA GAGAACAGAA ATCGGGGAAG TGGGGGGAAC GCCTCTGTTC AGTTCATTCC         2188

CAGAAGTCCA CAGGACGCAC AGCCCAGGCC ACAGCCAGGG CTCCACGGGG CGCCCTTGTC         2248

TCAGTCATTG CTGTTGTATG TTCGTGCTGG AGTTTTGTTG GTGTGAAAAT ACACTTATTT         2308

CAGCCAAAAC ATACCATTTC TACACCTCAA TCCTCCATTT GCTGTACTCT TTGCTAGTAC         2368

CAAAAGTAGA CTGATTACAC TGAGGTGAGG CTACAAGGGG TGTGTAACCG TGTAACACGT         2428

GAAGGCAGTG CTCACCTCTT CTTTACCAGA ACGGTTCTTT GACCAGCACA TTAACTTCTG         2488

GACTGCCGGC TCTAGTACCT TTTCAGTAAA GTGGTTCTCT GCCTTTTTAC TATACAGCAT         2548

ACCACGCCAC AGGGTTAGAA CCAACGAAGA AAATAAAATG AGGGTGCCCA GCTTATAAGA         2608

ATGGTGTTAG GGGGATGAGC ATGCTGTTTA TGAACGGAAA TCATGATTTC CCTGTAGAAA         2668

GTGAGGCTCA GATTAAATTT TAGAATATTT CTAAATGTC TTTTTCACAA TCATGTGACT          2728

GGGAAGGCAA TTTCATACTA AACTGATTAA ATAATACATT TATAATCTAC AACTGTTTGC         2788

ACTTACAGCT TTTTTTGTAA ATATAAACTA TAATTTATTG TCTATTTTAT ATCTGTTTTG         2848

CTGTGGCGTT GGGGGGGGGG CCGGGCTTTT GGGGGGGGGG GTTTGTTTGG GGGTGTCGT          2908

GGTGTGGGCG GGCGG                                                         2923

(2) INFORMATION FOR SEQ ID NO: 8:
```

(i) SEQUENCE CHARACTERISTICS:
  (A) LENGTH: 513 amino acids
  (B) TYPE: amino acid
  (D) TOPOLOGY: linear (ii) MOLECULE TYPE: protein (xi) SEQUENCE DESCRIPTION: SEQ ID NO: 8:

```
Met Pro Gly Leu Gly Arg Arg Ala Gln Trp Leu Cys Trp Trp Gly
-374             -370                 -365                 -360

Leu Leu Cys Ser Cys Cys Gly Pro Pro Leu Arg Pro Pro Leu Pro
            -355             -350                 -345

Ala Ala Ala Ala Ala Ala Ala Gly Gly Gln Leu Leu Gly Asp Gly Gly
        -340                 -335             -330

Ser Pro Gly Arg Thr Glu Gln Pro Pro Ser Pro Gln Ser Ser Ser
    -325             -320             -315

Gly Phe Leu Tyr Arg Arg Leu Lys Thr Gln Glu Lys Arg Glu Met Gln
-310             -305             -300             -295

Lys Glu Ile Leu Ser Val Leu Gly Leu Pro His Arg Pro Arg Pro Leu
            -290             -285             -280

His Gly Leu Gln Gln Pro Gln Pro Pro Ala Leu Arg Gln Gln Glu Glu
        -275             -270             -265

Gln Gln Gln Gln Gln Gln Leu Pro Arg Gly Glu Pro Pro Pro Gly Arg
    -260             -255             -250

Leu Lys Ser Ala Pro Leu Phe Met Leu Asp Leu Tyr Asn Ala Leu Ser
    -245             -240             -235

Ala Asp Asn Asp Glu Asp Gly Ala Ser Glu Gly Glu Arg Gln Gln Ser
-230             -225             -220             -215

Trp Pro His Glu Ala Ala Ser Ser Ser Gln Arg Arg Gln Pro Pro Pro
            -210             -205             -200

Gly Ala Ala His Pro Leu Asn Arg Lys Ser Leu Leu Ala Pro Gly Ser
        -195             -190             -185

Gly Ser Gly Gly Ala Ser Pro Leu Thr Ser Ala Gln Asp Ser Ala Phe
    -180             -175             -170

Leu Asn Asp Ala Asp Met Val Met Ser Phe Val Asn Leu Val Glu Tyr
    -165             -160             -155

Asp Lys Glu Phe Ser Pro Arg Gln Arg His His Lys Glu Phe Lys Phe
-150             -145             -140             -135

Asn Leu Ser Gln Ile Pro Glu Gly Glu Val Val Thr Ala Ala Glu Phe
            -130             -125             -120

Arg Ile Tyr Lys Asp Cys Val Met Gly Ser Phe Lys Asn Gln Thr Phe
        -115             -110             -105

Leu Ile Ser Ile Tyr Gln Val Leu Gln Glu His Gln His Arg Asp Ser
    -100             -95              -90

Asp Leu Phe Leu Leu Asp Thr Arg Val Val Trp Ala Ser Glu Glu Gly
    -85              -80              -75

Trp Leu Glu Phe Asp Ile Thr Ala Thr Ser Asn Leu Trp Val Val Thr
-70              -65              -60              -55

Pro Gln His Asn Met Gly Leu Gln Leu Ser Val Val Thr Arg Asp Gly
            -50              -45              -40

Val His Val His Pro Arg Ala Ala Gly Leu Val Gly Arg Asp Gly Pro
        -35              -30              -25

Tyr Asp Lys Gln Pro Phe Met Val Ala Phe Phe Lys Val Ser Glu Val
    -20              -15              -10

His Val Arg Thr Thr Arg Ser Ala Ser Ser Arg Arg Arg Gln Gln Ser
```

```
         -5                  1                 5                  10
      Arg Asn Arg Ser Thr Gln Ser Gln Asp Val Ala Arg Val Ser Ser Ala
                          15              20              25
      Ser Asp Tyr Asn Ser Ser Glu Leu Lys Thr Ala Cys Arg Lys His Glu
                      30              35              40
      Leu Tyr Val Ser Phe Gln Asp Leu Gly Trp Gln Asp Trp Ile Ile Ala
                  45              50              55
      Pro Lys Gly Tyr Ala Ala Asn Tyr Cys Asp Gly Glu Cys Ser Phe Pro
              60              65              70
      Leu Asn Ala His Met Asn Ala Thr Asn His Ala Ile Val Gln Thr Leu
       75              80              85                      90
      Val His Leu Met Asn Pro Glu Tyr Val Pro Lys Pro Cys Cys Ala Pro
                      95              100             105
      Thr Lys Leu Asn Ala Ile Ser Val Leu Tyr Phe Asp Asp Asn Ser Asn
                  110             115             120
      Val Ile Leu Lys Lys Tyr Arg Asn Met Val Val Arg Ala Cys Gly Cys
                  125             130             135
      His
```

(2) INFORMATION FOR SEQ ID NO: 9:

(i) SEQUENCE CHARACTERISTICS:
        (A) LENGTH: 2153 base pairs
        (B) TYPE: nucleic acid
        (C) STRANDEDNESS: double
        (D) TOPOLOGY: linear (iii) HYPOTHETICAL: NO (vi) ORIGINAL SOURCE:
        (A) ORGANISM: Homo sapiens
        (H) CELL LINE: U2-OS osteosarcoma (vii) IMMEDIATE SOURCE:
        (A) LIBRARY: U2-OS human osteosarcoma cDNA library
        (B) CLONE: U2-16

(viii) POSITION IN GENOME:
        (C) UNITS: bp (ix) FEATURE:
        (A) NAME/KEY: CDS
        (B) LOCATION: 699..2063

(ix) FEATURE:
        (A) NAME/KEY: mat_peptide
        (B) LOCATION: 1647..2060

(ix) FEATURE:
        (A) NAME/KEY: mRNA
        (B) LOCATION: 1..2153

(xi) SEQUENCE DESCRIPTION: SEQ ID NO: 9:

```
CTGGTATATT TGTGCCTGCT GGAGGTGGAA TTAACAGTAA GAAGGAGAAA GGGATTGAAT      60

GGACTTACAG GAAGGATTTC AAGTAAATTC AGGGAAACAC ATTTACTTGA ATAGTACAAC     120

CTAGAGTATT ATTTTACACT AAGACGACAC AAAAGATGTT AAAGTTATCA CCAAGCTGCC     180

GGACAGATAT ATATTCCAAC ACCAAGGTGC AGATCAGCAT AGATCTGTGA TTCAGAAATC     240

AGGATTTGTT TTGGAAAGAG CTCAAGGGTT GAGAAGAACT CAAAAGCAAG TGAAGATTAC     300

TTTGGGAACT ACAGTTTATC AGAAGATCAA CTTTTGCTAA TTCAAATACC AAAGGCCTGA     360

TTATCATAAA TTCATATAGG AATGCATAGG TCATCTGATC AAATAATATT AGCCGTCTTC     420

TGCTACATCA ATGCAGCAAA AACTCTTAAC AACTGTGGAT AATTGGAAAT CTGAGTTTCA     480
```

```
GCTTTCTTAG AAATAACTAC TCTTGACATA TTCCAAAATA TTTAAAATAG GACAGGAAAA      540

TCGGTGAGGA TGTTGTGCTC AGAAATGTCA CTGTCATGAA AAATAGGTAA ATTTGTTTTT      600

TCAGCTACTG GGAAACTGTA CCTCCTAGAA CCTTAGGTTT TTTTTTTTTT AAGAGGACAA      660

GAAGGACTAA AAATATCAAC TTTTGCTTTT GGACAAAA ATG CAT CTG ACT GTA          713
                                          Met His Leu Thr Val
                                              -316-315

TTT TTA CTT AAG GGT ATT GTG GGT TTC CTC TGG AGC TGC TGG GTT CTA        761
Phe Leu Leu Lys Gly Ile Val Gly Phe Leu Trp Ser Cys Trp Val Leu
       -310             -305             -300

GTG GGT TAT GCA AAA GGA GGT TTG GGA GAC AAT CAT GTT CAC TCC AGT        809
Val Gly Tyr Ala Lys Gly Gly Leu Gly Asp Asn His Val His Ser Ser
-295             -290             -285             -280

TTT ATT TAT AGA AGA CTA CGG AAC CAC GAA AGA CGG GAA ATA CAA AGG        857
Phe Ile Tyr Arg Arg Leu Arg Asn His Glu Arg Arg Glu Ile Gln Arg
               -275             -270             -265

GAA ATT CTC TCT ATC TTG GGT TTG CCT CAC AGA CCC AGA CCA TTT TCA        905
Glu Ile Leu Ser Ile Leu Gly Leu Pro His Arg Pro Arg Pro Phe Ser
           -260             -255             -250

CCT GGA AAA ATG ACC AAT CAA GCG TCC TCT GCA CCT CTC TTT ATG CTG        953
Pro Gly Lys Met Thr Asn Gln Ala Ser Ser Ala Pro Leu Phe Met Leu
       -245             -240             -235

GAT CTC TAC AAT GCC GAA GAA AAT CCT GAA GAG TCG GAG TAC TCA GTA       1001
Asp Leu Tyr Asn Ala Glu Glu Asn Pro Glu Glu Ser Glu Tyr Ser Val
       -230             -225             -220

AGG GCA TCC TTG GCA GAA GAG ACC AGA GGG GCA AGA AAG GGA TAC CCA       1049
Arg Ala Ser Leu Ala Glu Glu Thr Arg Gly Ala Arg Lys Gly Tyr Pro
-215             -210             -205             -200

GCC TCT CCC AAT GGG TAT CCT CGT CGC ATA CAG TTA TCT CGG ACG ACT       1097
Ala Ser Pro Asn Gly Tyr Pro Arg Arg Ile Gln Leu Ser Arg Thr Thr
               -195             -190             -185

CCT CTG ACC ACC CAG AGT CCT CCT CTA GCC AGC CTC CAT GAT ACC AAC       1145
Pro Leu Thr Thr Gln Ser Pro Pro Leu Ala Ser Leu His Asp Thr Asn
           -180             -175             -170

TTT CTG AAT GAT GCT GAC ATG GTC ATG AGC TTT GTC AAC TTA GTT GAA       1193
Phe Leu Asn Asp Ala Asp Met Val Met Ser Phe Val Asn Leu Val Glu
       -165             -160             -155

AGA GAC AAG GAT TTT TCT CAC CAG CGA AGG CAT TAC AAA GAA TTT CGA       1241
Arg Asp Lys Asp Phe Ser His Gln Arg Arg His Tyr Lys Glu Phe Arg
   -150             -145             -140

TTT GAT CTT ACC CAA ATT CCT CAT GGA GAG GCA GTG ACA GCA GCT GAA       1289
Phe Asp Leu Thr Gln Ile Pro His Gly Glu Ala Val Thr Ala Ala Glu
-135             -130             -125             -120

TTC CGG ATA TAC AAG GAC CGG AGC AAC AAC CGA TTT GAA AAT GAA ACA       1337
Phe Arg Ile Tyr Lys Asp Arg Ser Asn Asn Arg Phe Glu Asn Glu Thr
           -115             -110             -105

ATT AAG ATT AGC ATA TAT CAA ATC ATC AAG GAA TAC ACA AAT AGG GAT       1385
Ile Lys Ile Ser Ile Tyr Gln Ile Ile Lys Glu Tyr Thr Asn Arg Asp
       -100              -95              -90

GCA GAT CTG TTC TTG TTA GAC ACA AGA AAG GCC CAA GCT TTA GAT GTG       1433
Ala Asp Leu Phe Leu Leu Asp Thr Arg Lys Ala Gln Ala Leu Asp Val
    -85              -80              -75

GGT TGG CTT GTC TTT GAT ATC ACT GTG ACC AGC AAT CAT TGG GTG ATT       1481
Gly Trp Leu Val Phe Asp Ile Thr Val Thr Ser Asn His Trp Val Ile
   -70              -65              -60

AAT CCC CAG AAT AAT TTG GGC TTA CAG CTC TGT GCA GAA ACA GGG GAT       1529
Asn Pro Gln Asn Asn Leu Gly Leu Gln Leu Cys Ala Glu Thr Gly Asp
   -55              -50              -45              -40
```

```
GGA CGC AGT ATC AAC GTA AAA TCT GCT GGT CTT GTG GGA AGA CAG GGA      1577
Gly Arg Ser Ile Asn Val Lys Ser Ala Gly Leu Val Gly Arg Gln Gly
            -35                 -30                 -25

CCT CAG TCA AAA CAA CCA TTC ATG GTG GCC TTC TTC AAG GCG AGT GAG      1625
Pro Gln Ser Lys Gln Pro Phe Met Val Ala Phe Phe Lys Ala Ser Glu
        -20                 -15                 -10

GTA CTT CTT CGA TCC GTG AGA GCA GCC AAC AAA CGA AAA AAT CAA AAC      1673
Val Leu Leu Arg Ser Val Arg Ala Ala Asn Lys Arg Lys Asn Gln Asn
    -5                   1                   5

CGC AAT AAA TCC AGC TCT CAT CAG GAC TCC TCC AGA ATG TCC AGT GTT      1721
Arg Asn Lys Ser Ser Ser His Gln Asp Ser Ser Arg Met Ser Ser Val
 10                  15                  20                  25

GGA GAT TAT AAC ACA AGT GAG CAA AAA CAA GCC TGT AAG AAG CAC GAA      1769
Gly Asp Tyr Asn Thr Ser Glu Gln Lys Gln Ala Cys Lys Lys His Glu
             30                  35                  40

CTC TAT GTG AGC TTC CGG GAT CTG GGA TGG CAG GAC TGG ATT ATA GCA      1817
Leu Tyr Val Ser Phe Arg Asp Leu Gly Trp Gln Asp Trp Ile Ile Ala
             45                  50                  55

CCA GAA GGA TAC GCT GCA TTT TAT TGT GAT GGA GAA TGT TCT TTT CCA      1865
Pro Glu Gly Tyr Ala Ala Phe Tyr Cys Asp Gly Glu Cys Ser Phe Pro
         60                  65                  70

CTT AAC GCC CAT ATG AAT GCC ACC AAC CAC GCT ATA GTT CAG ACT CTG      1913
Leu Asn Ala His Met Asn Ala Thr Asn His Ala Ile Val Gln Thr Leu
 75                  80                  85

GTT CAT CTG ATG TTT CCT GAC CAC GTA CCA AAG CCT TGT TGT GCT CCA      1961
Val His Leu Met Phe Pro Asp His Val Pro Lys Pro Cys Cys Ala Pro
 90                  95                 100                 105

ACC AAA TTA AAT GCC ATC TCT GTT CTG TAC TTT GAT GAC AGC TCC AAT      2009
Thr Lys Leu Asn Ala Ile Ser Val Leu Tyr Phe Asp Asp Ser Ser Asn
             110                 115                 120

GTC ATT TTG AAA AAA TAT AGA AAT ATG GTA GTA CGC TCA TGT GGC TGC      2057
Val Ile Leu Lys Lys Tyr Arg Asn Met Val Val Arg Ser Cys Gly Cys
             125                 130                 135

CAC TAATATTAAA TAATATTGAT AATAACAAAA AGATCTGTAT TAAGGTTTAT           2110
His

GGCTGCAATA AAAAGCATAC TTTCAGACAA ACAGAAAAAA AAA                      2153
```

(2) INFORMATION FOR SEQ ID NO: 10:

(i) SEQUENCE CHARACTERISTICS:
        (A) LENGTH: 454 amino acids
        (B) TYPE: amino acid
        (D) TOPOLOGY: linear (ii) MOLECULE TYPE: protein (xi) SEQUENCE DESCRIPTION: SEQ ID NO: 10:

```
Met His Leu Thr Val Phe Leu Leu Lys Gly Ile Val Gly Phe Leu Trp
-316 -315                -310                -305

Ser Cys Trp Val Leu Val Gly Tyr Ala Lys Gly Gly Leu Gly Asp Asn
-300                 -295                 -290                 -285

His Val His Ser Ser Phe Ile Tyr Arg Arg Leu Arg Asn His Glu Arg
                 -280                 -275                 -270

Arg Glu Ile Gln Arg Glu Ile Leu Ser Ile Leu Gly Leu Pro His Arg
             -265                 -260                 -255

Pro Arg Pro Phe Ser Pro Gly Lys Met Thr Asn Gln Ala Ser Ser Ala
         -250                 -245                 -240

Pro Leu Phe Met Leu Asp Leu Tyr Asn Ala Glu Glu Asn Pro Glu Glu
     -235                 -230                 -225
```

```
Ser Glu Tyr Ser Val Arg Ala Ser Leu Ala Glu Glu Thr Arg Gly Ala
-220                -215                -210                -205

Arg Lys Gly Tyr Pro Ala Ser Pro Asn Gly Tyr Pro Arg Arg Ile Gln
            -200                -195                -190

Leu Ser Arg Thr Thr Pro Leu Thr Thr Gln Ser Pro Pro Leu Ala Ser
            -185                -180                -175

Leu His Asp Thr Asn Phe Leu Asn Asp Ala Asp Met Val Met Ser Phe
            -170                -165                -160

Val Asn Leu Val Glu Arg Asp Lys Asp Phe Ser His Gln Arg Arg His
        -155                -150                -145

Tyr Lys Glu Phe Arg Phe Asp Leu Thr Gln Ile Pro His Gly Glu Ala
-140                -135                -130                -125

Val Thr Ala Ala Glu Phe Arg Ile Tyr Lys Asp Arg Ser Asn Asn Arg
            -120                -115                -110

Phe Glu Asn Glu Thr Ile Lys Ile Ser Ile Tyr Gln Ile Ile Lys Glu
            -105                -100                -95

Tyr Thr Asn Arg Asp Ala Asp Leu Phe Leu Asp Thr Arg Lys Ala
            -90                 -85                 -80

Gln Ala Leu Asp Val Gly Trp Leu Val Phe Asp Ile Thr Val Thr Ser
-75                 -70                  -65

Asn His Trp Val Ile Asn Pro Gln Asn Asn Leu Gly Leu Gln Leu Cys
-60                 -55                  -50                 -45

Ala Glu Thr Gly Asp Gly Arg Ser Ile Asn Val Lys Ser Ala Gly Leu
            -40                 -35                  -30

Val Gly Arg Gln Gly Pro Gln Ser Lys Gln Pro Phe Met Val Ala Phe
            -25                 -20                  -15

Phe Lys Ala Ser Glu Val Leu Leu Arg Ser Val Arg Ala Ala Asn Lys
            -10                  -5                   1

Arg Lys Asn Gln Asn Arg Asn Lys Ser Ser His Gln Asp Ser Ser
 5                  10                   15                  20

Arg Met Ser Ser Val Gly Asp Tyr Asn Thr Ser Glu Gln Lys Gln Ala
                25                   30                  35

Cys Lys Lys His Glu Leu Tyr Val Ser Phe Arg Asp Leu Gly Trp Gln
                40                   45                  50

Asp Trp Ile Ile Ala Pro Glu Gly Tyr Ala Ala Phe Tyr Cys Asp Gly
                55                   60                  65

Glu Cys Ser Phe Pro Leu Asn Ala His Met Asn Ala Thr Asn His Ala
 70                  75                   80

Ile Val Gln Thr Leu Val His Leu Met Phe Pro Asp His Val Pro Lys
 85                  90                   95                 100

Pro Cys Cys Ala Pro Thr Lys Leu Asn Ala Ile Ser Val Leu Tyr Phe
                105                  110                 115

Asp Asp Ser Ser Asn Val Ile Leu Lys Lys Tyr Arg Asn Met Val Val
                120                  125                 130

Arg Ser Cys Gly Cys His
                135

(2) INFORMATION FOR SEQ ID NO: 11:

(i) SEQUENCE CHARACTERISTICS:
        (A) LENGTH: 1003 base pairs
        (B) TYPE: nucleic acid
        (C) STRANDEDNESS: double
        (D) TOPOLOGY: circular (ii) MOLECULE TYPE: cDNA to mRNA
```

(iii) HYPOTHETICAL: NO (vi) ORIGINAL SOURCE:
    (A) ORGANISM: Homo sapiens
    (F) TISSUE TYPE: Human Heart (vii) IMMEDIATE SOURCE:
    (A) LIBRARY: Human heart cDNA library stratagene catalog
        #936208
    (B) CLONE: hH38

(viii) POSITION IN GENOME:
    (C) UNITS: bp (ix) FEATURE:
    (A) NAME/KEY: CDS
    (B) LOCATION: 8..850

(ix) FEATURE:
    (A) NAME/KEY: mat_peptide
    (B) LOCATION: 427..843

(ix) FEATURE:
    (A) NAME/KEY: mRNA
    (B) LOCATION: 1..997

(xi) SEQUENCE DESCRIPTION: SEQ ID NO: 11:

```
GAATTCC GAG CCC CAT TGG AAG GAG TTC CGC TTT GAC CTG ACC CAG ATC           49
        Glu Pro His Trp Lys Glu Phe Arg Phe Asp Leu Thr Gln Ile
        -139            -135                -130

CCG GCT GGG GAG GCG GTC ACA GCT GCG GAG TTC CGG ATT TAC AAG GTG           97
Pro Ala Gly Glu Ala Val Thr Ala Ala Glu Phe Arg Ile Tyr Lys Val
-125            -120                -115                -110

CCC AGC ATC CAC CTG CTC AAC AGG ACC CTC CAC GTC AGC ATG TTC CAG          145
Pro Ser Ile His Leu Leu Asn Arg Thr Leu His Val Ser Met Phe Gln
                -105                -100                -95

GTG GTC CAG GAG CAG TCC AAC AGG GAG TCT GAC TTG TTC TTT TTG GAT          193
Val Val Gln Glu Gln Ser Asn Arg Glu Ser Asp Leu Phe Phe Leu Asp
            -90                 -85                 -80

CTT CAG ACG CTC CGA GCT GGA GAC GAG GGC TGG CTG GTG CTG GAT GTC          241
Leu Gln Thr Leu Arg Ala Gly Asp Glu Gly Trp Leu Val Leu Asp Val
        -75                 -70                 -65

ACA GCA GCC AGT GAC TGC TGG TTG CTG AAG CGT CAC AAG GAC CTG GGA          289
Thr Ala Ala Ser Asp Cys Trp Leu Leu Lys Arg His Lys Asp Leu Gly
    -60                 -55                 -50

CTC CGC CTC TAT GTG GAG ACT GAG GAT GGG CAC AGC GTG GAT CCT GGC          337
Leu Arg Leu Tyr Val Glu Thr Glu Asp Gly His Ser Val Asp Pro Gly
-45                 -40                 -35                 -30

CTG GCC GGC CTG CTG GGT CAA CGG GCC CCA CGC TCC CAA CAG CCT TTC          385
Leu Ala Gly Leu Leu Gly Gln Arg Ala Pro Arg Ser Gln Gln Pro Phe
                -25                 -20                 -15

GTG GTC ACT TTC TTC AGG GCC AGT CCG AGT CCC ATC CGC ACC CCT CGG          433
Val Val Thr Phe Phe Arg Ala Ser Pro Ser Pro Ile Arg Thr Pro Arg
            -10                 -5                   1

GCA GTG AGG CCA CTG AGG AGG AGG CAG CCG AAG AAA AGC AAC GAG CTG          481
Ala Val Arg Pro Leu Arg Arg Arg Gln Pro Lys Lys Ser Asn Glu Leu
    5                   10                  15

CCG CAG GCC AAC CGA CTC CCA GGG ATC TTT GAT GAC GTC CAC GGC TCC          529
Pro Gln Ala Asn Arg Leu Pro Gly Ile Phe Asp Asp Val His Gly Ser
20                  25                  30                  35

CAC GGC CGG CAG GTC TGC CGT CGG CAC GAG CTC TAC GTC AGC TTC CAG          577
His Gly Arg Gln Val Cys Arg Arg His Glu Leu Tyr Val Ser Phe Gln
                40                  45                  50

GAC CTT GGC TGG CTG GAC TGG GTC ATC GCC CCC CAA GGC TAC TCA GCC          625
Asp Leu Gly Trp Leu Asp Trp Val Ile Ala Pro Gln Gly Tyr Ser Ala
```

```
                       55                   60                   65
TAT TAC TGT GAG GGG GAG TGC TCC TTC CCG CTG GAC TCC TGC ATG AAC      673
Tyr Tyr Cys Glu Gly Glu Cys Ser Phe Pro Leu Asp Ser Cys Met Asn
            70                  75                  80

GCC ACC AAC CAC GCC ATC CTG CAG TCC CTG GTG CAC CTG ATG AAG CCA      721
Ala Thr Asn His Ala Ile Leu Gln Ser Leu Val His Leu Met Lys Pro
        85                  90                  95

AAC GCA GTC CCC AAG GCG TGC TGT GCA CCC ACC AAG CTG AGC GCC ACC      769
Asn Ala Val Pro Lys Ala Cys Cys Ala Pro Thr Lys Leu Ser Ala Thr
100             105                 110                 115

TCT GTG CTC TAC TAT GAC AGC AGC AAC AAC GTC ATC CTG CGC AAG CAC      817
Ser Val Leu Tyr Tyr Asp Ser Ser Asn Asn Val Ile Leu Arg Lys His
                120                 125                 130

CGC AAC ATG GTG GTC AAG GCC TGC GGC TGC CAC TGAGTCAGCC CGCCCAGCCC    870
Arg Asn Met Val Val Lys Ala Cys Gly Cys His
                135                 140

TACTGCAGCC ACCCTTCTCA TCTGGATCGG GCCCTGCAGA GGCAGAAAAC CCTTAAATGC    930

TGTCACAGCT CAAGCAGGAG TGTCAGGGGC CCTCACTCTC GGTGCCTACT TCCTGTCAGG    990

CTTCTGGGAA TTC                                                      1003
```

(2) INFORMATION FOR SEQ ID NO: 12:

(i) SEQUENCE CHARACTERISTICS:
        (A) LENGTH: 281 amino acids
        (B) TYPE: amino acid
        (D) TOPOLOGY: linear (ii) MOLECULE TYPE: protein (xi) SEQUENCE DESCRIPTION: SEQ ID NO: 12:

```
Glu Pro His Trp Lys Glu Phe Arg Phe Asp Leu Thr Gln Ile Pro Ala
-139            -135                -130                -125

Gly Glu Ala Val Thr Ala Ala Glu Phe Arg Ile Tyr Lys Val Pro Ser
            -120                -115                -110

Ile His Leu Leu Asn Arg Thr Leu His Val Ser Met Phe Gln Val Val
        -105                 -100                -95

Gln Glu Gln Ser Asn Arg Glu Ser Asp Leu Phe Phe Leu Asp Leu Gln
    -90                 -85                 -80

Thr Leu Arg Ala Gly Asp Glu Gly Trp Leu Val Leu Asp Val Thr Ala
-75             -70                 -65                 -60

Ala Ser Asp Cys Trp Leu Leu Lys Arg His Lys Asp Leu Gly Leu Arg
                -55                 -50                 -45

Leu Tyr Val Glu Thr Glu Asp Gly His Ser Val Asp Pro Gly Leu Ala
                -40                 -35                 -30

Gly Leu Leu Gly Gln Arg Ala Pro Arg Ser Gln Gln Pro Phe Val Val
            -25                 -20                 -15

Thr Phe Phe Arg Ala Ser Pro Ser Pro Ile Arg Thr Pro Arg Ala Val
-10              -5                   1                   5

Arg Pro Leu Arg Arg Arg Gln Pro Lys Lys Ser Asn Glu Leu Pro Gln
             10                  15                  20

Ala Asn Arg Leu Pro Gly Ile Phe Asp Asp Val His Gly Ser His Gly
                25                  30                  35

Arg Gln Val Cys Arg Arg His Glu Leu Tyr Val Ser Phe Gln Asp Leu
             40                  45                  50

Gly Trp Leu Asp Trp Val Ile Ala Pro Gln Gly Tyr Ser Ala Tyr Tyr
         55                  60                  65
```

```
Cys Glu Gly Glu Cys Ser Phe Pro Leu Asp Ser Cys Met Asn Ala Thr
 70                  75                  80                  85

Asn His Ala Ile Leu Gln Ser Leu Val His Leu Met Lys Pro Asn Ala
                 90                  95                 100

Val Pro Lys Ala Cys Cys Ala Pro Thr Lys Leu Ser Ala Thr Ser Val
                105                 110                 115

Leu Tyr Tyr Asp Ser Ser Asn Asn Val Ile Leu Arg Lys His Arg Asn
                120                 125                 130

Met Val Val Lys Ala Cys Gly Cys His
    135                 140
```

(2) INFORMATION FOR SEQ ID NO: 13:

(i) SEQUENCE CHARACTERISTICS:
        (A) LENGTH: 3623 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
        (B) CLONE: pALBP2-781

(ix) FEATURE:
        (A) NAME/KEY: CDS
        (B) LOCATION: 2724..3071

(ix) FEATURE:
        (A) NAME/KEY: terminator
        (B) LOCATION: 3150..3218

(ix) FEATURE:
        (A) NAME/KEY: RBS
        (B) LOCATION: 2222..2723

(xi) SEQUENCE DESCRIPTION: SEQ ID NO: 13:

```
GACGAAAGGG CCTCGTGATA CGCCTATTTT TATAGGTTAA TGTCATGATA ATAATGGTTT     60

CTTAGACGTC AGGTGGCACT TTTCGGGGAA ATGTGCGCGG AACCCCTATT TGTTTATTTT    120

TCTAAATACA TTCAAATATG TATCCGCTCA TGAGACAATA ACCCTGATAA ATGCTTCAAT    180

AATATTGAAA AAGGAAGAGT ATGAGTATTC AACATTTCCG TGTCGCCCTT ATTCCCTTTT    240

TTGCGGCATT TTGCCTTCCT GTTTTTGCTC ACCCAGAAAC GCTGGTGAAA GTAAAAGATG    300

CTGAAGATCA GTTGGGTGCA CGAGTGGGTT ACATCGAACT GGATCTCAAC AGCGGTAAGA    360

TCCTTGAGAG TTTTCGCCCC GAAGAACGTT TTCCAATGAT GAGCACTTTT AAAGTTCTGC    420

TATGTGGCGC GGTATTATCC CGTATTGACG CCGGGCAAGA GCAACTCGGT CGCCGCATAC    480

ACTATTCTCA GAATGACTTG GTTGAGTACT CACCAGTCAC AGAAAAGCAT CTTACGGATG    540

GCATGACAGT AAGAGAATTA TGCAGTGCTG CCATAACCAT GAGTGATAAC ACTGCGGCCA    600

ACTTACTTCT GACAACGATC GGAGGACCGA AGGAGCTAAC CGCTTTTTTG CACAACATGG    660

GGGATCATGT AACTCGCCTT GATCGTTGGG AACCGGAGCT GAATGAAGCC ATACCAAACG    720

ACGAGCGTGA CACCACGATG CCTGTAGCAA TGGCAACAAC GTTGCGCAAA CTATTAACTG    780

GCGAACTACT TACTCTAGCT TCCCGGCAAC AATTAATAGA CTGGATGGAG GCGGATAAAG    840

TTGCAGGACC ACTTCTGCGC TCGGCCCTTC CGGCTGGCTG GTTTATTGCT GATAAATCTG    900

GAGCCGGTGA GCGTGGGTCT CGCGGTATCA TTGCAGCACT GGGGCCAGAT GGTAAGCCCT    960

CCCGTATCGT AGTTATCTAC ACGACGGGGA GTCAGGCAAC TATGGATGAA CGAAATAGAC   1020

AGATCGCTGA GATAGGTGCC TCACTGATTA AGCATTGGTA ACTGTCAGAC CAAGTTTACT   1080
```

```
CATATATACT TTAGATTGAT TTAAAACTTC ATTTTTAATT TAAAAGGATC TAGGTGAAGA   1140

TCCTTTTTGA TAATCTCATG ACCAAAATCC CTTAACGTGA GTTTTCGTTC CACTGAGCGT   1200

CAGACCCCGT AGAAAAGATC AAAGGATCTT CTTGAGATCC TTTTTTTCTG CGCGTAATCT   1260

GCTGCTTGCA AACAAAAAAA CCACCGCTAC CAGCGGTGGT TTGTTTGCCG GATCAAGAGC   1320

TACCAACTCT TTTTCCGAAG GTAACTGGCT TCAGCAGAGC GCAGATACCA AATACTGTCC   1380

TTCTAGTGTA GCCGTAGTTA GGCCACCACT TCAAGAACTC TGTAGCACCG CCTACATACC   1440

TCGCTCTGCT AATCCTGTTA CCAGTGGCTG CTGCCAGTGG CGATAAGTCG TGTCTTACCG   1500

GGTTGGACTC AAGACGATAG TTACCGGATA AGGCGCAGCG GTCGGGCTGA ACGGGGGGTT   1560

CGTGCACACA GCCCAGCTTG GAGCGAACGA CCTACACCGA ACTGAGATAC CTACAGCGTG   1620

AGCATTGAGA AAGCGCCACG CTTCCCGAAG GGAGAAAGGC GGACAGGTAT CCGGTAAGCG   1680

GCAGGGTCGG AACAGGAGAG CGCACGAGGG AGCTTCCAGG GGGAAACGCC TGGTATCTTT   1740

ATAGTCCTGT CGGGTTTCGC CACCTCTGAC TTGAGCGTCG ATTTTTGTGA TGCTCGTCAG   1800

GGGGGCGGAG CCTATGGAAA AACGCCAGCA ACGCGGCCTT TTTACGGTTC CTGGCCTTTT   1860

GCTGGCCTTT TGCTCACATG TTCTTTCCTG CGTTATCCCC TGATTCTGTG GATAACCGTA   1920

TTACCGCCTT TGAGTGAGCT GATACCGCTC GCCGCAGCCG AACGACCGAG CGCAGCGAGT   1980

CAGTGAGCGA GGAAGCGGAA GAGCGCCCAA TACGCAAACC GCCTCTCCCC GCGCGTTGGC   2040

CGATTCATTA ATGCAGAATT GATCTCTCAC CTACCAAACA ATGCCCCCCT GCAAAAAATA   2100

AATTCATATA AAAAACATAC AGATAACCAT CTGCGGTGAT AAATTATCTC TGGCGGTGTT   2160

GACATAAATA CCACTGGCGG TGATACTGAG CACATCAGCA GGACGCACTG ACCACCATGA   2220

AGGTGACGCT CTTAAAAATT AAGCCCTGAA GAAGGGCAGC ATTCAAAGCA GAAGGCTTTG   2280

GGGTGTGTGA TACGAAACGA AGCATTGGCC GTAAGTGCGA TTCCGGATTA GCTGCCAATG   2340

TGCCAATCGC GGGGGGTTTT CGTTCAGGAC TACAACTGCC ACACACCACC AAAGCTAACT   2400

GACAGGAGAA TCCAGATGGA TGCACAAACA CGCCGCCGCG AACGTCGCGC AGAGAAACAG   2460

GCTCAATGGA AAGCAGCAAA TCCCCTGTTG GTTGGGTAA GCGCAAAACC AGTTCCGAAA    2520

GATTTTTTTA ACTATAAACG CTGATGGAAG CGTTTATGCG GAAGAGGTAA AGCCCTTCCC   2580

GAGTAACAAA AAAACAACAG CATAAATAAC CCCGCTCTTA CACATTCCAG CCCTGAAAAA   2640

GGGCATCAAA TTAAACCACA CCTATGGTGT ATGCATTTAT TTGCATACAT TCAATCAATT   2700

GTTATCTAAG GAAATACTTA CAT ATG CAA GCT AAA CAT AAA CAA CGT AAA       2750
                          Met Gln Ala Lys His Lys Gln Arg Lys
                            1               5

CGT CTG AAA TCT AGC TGT AAG AGA CAC CCT TTG TAC GTG GAC TTC AGT    2798
Arg Leu Lys Ser Ser Cys Lys Arg His Pro Leu Tyr Val Asp Phe Ser
 10              15                  20                  25

GAC GTG GGG TGG AAT GAC TGG ATT GTG GCT CCC CCG GGG TAT CAC GCC    2846
Asp Val Gly Trp Asn Asp Trp Ile Val Ala Pro Pro Gly Tyr His Ala
             30                  35                  40

TTT TAC TGC CAC GGA GAA TGC CCT TTT CCT CTG GCT GAT CAT CTG AAC    2894
Phe Tyr Cys His Gly Glu Cys Pro Phe Pro Leu Ala Asp His Leu Asn
                 45                  50                  55

TCC ACT AAT CAT GCC ATT GTT CAG ACG TTG GTC AAC TCT GTT AAC TCT    2942
Ser Thr Asn His Ala Ile Val Gln Thr Leu Val Asn Ser Val Asn Ser
             60                  65                  70

AAG ATT CCT AAG GCA TGC TGT GTC CCG ACA GAA CTC AGT GCT ATC TCG    2990
Lys Ile Pro Lys Ala Cys Cys Val Pro Thr Glu Leu Ser Ala Ile Ser
 75                  80                  85

ATG CTG TAC CTT GAC GAG AAT GAA AAG GTT GTA TTA AAG AAC TAT CAG    3038
```

```
Met Leu Tyr Leu Asp Glu Asn Glu Lys Val Val Leu Lys Asn Tyr Gln
 90              95                 100                 105

GAC ATG GTT GTG GAG GGT TGT GGG TGT CGC TAGTACAGCA AAATTAAATA           3088
Asp Met Val Val Glu Gly Cys Gly Cys Arg
            110                 115

CATAAATATA TATATATATA TATATTTTAG AAAAAAGAAA AAAATCTAGA GTCGACCTGC       3148

AGTAATCGTA CAGGGTAGTA CAAATAAAAA AGGCACGTCA GATGACGTGC CTTTTTTCTT       3208

GTGAGCAGTA AGCTTGGCAC TGGCCGTCGT TTTACAACGT CGTGACTGGG AAAACCCTGG       3268

CGTTACCCAA CTTAATCGCC TTGCAGCACA TCCCCCTTTC GCCAGCTGGC GTAATAGCGA       3328

AGAGGCCCGC ACCGATCGCC CTTCCCAACA GTTGCGCAGC CTGAATGGCG AATGGCGCCT       3388

GATGCGGTAT TTTCTCCTTA CGCATCTGTG CGGTATTTCA CACCGCATAT ATGGTGCACT       3448

CTCAGTACAA TCTGCTCTGA TGCCGCATAG TTAAGCCAGC CCCGACACCC GCCAACACCC       3508

GCTGACGCGC CCTGACGGGC TTGTCTGCTC CCGGCATCCG CTTACAGACA AGCTGTGACC       3568

GTCTCCGGGA GCTGCATGTG TCAGAGGTTT TCACCGTCAT CACCGAAACG CGCGA           3623

(2) INFORMATION FOR SEQ ID NO: 14:

(i) SEQUENCE CHARACTERISTICS:
        (A) LENGTH: 115 amino acids
        (B) TYPE: amino acid
        (D) TOPOLOGY: linear (ii) MOLECULE TYPE: protein (xi) SEQUENCE DESCRIPTION: SEQ ID NO: 14:

Met Gln Ala Lys His Lys Gln Arg Lys Arg Leu Lys Ser Ser Cys Lys
 1               5                  10                  15

Arg His Pro Leu Tyr Val Asp Phe Ser Asp Val Gly Trp Asn Asp Trp
                20                  25                  30

Ile Val Ala Pro Pro Gly Tyr His Ala Phe Tyr Cys His Gly Glu Cys
            35                  40                  45

Pro Phe Pro Leu Ala Asp His Leu Asn Ser Thr Asn His Ala Ile Val
        50                  55                  60

Gln Thr Leu Val Asn Ser Val Asn Ser Lys Ile Pro Lys Ala Cys Cys
65                  70                  75                  80

Val Pro Thr Glu Leu Ser Ala Ile Ser Met Leu Tyr Leu Asp Glu Asn
                85                  90                  95

Glu Lys Val Val Leu Lys Asn Tyr Gln Asp Met Val Val Glu Gly Cys
                100                 105                 110

Gly Cys Arg
        115

(2) INFORMATION FOR SEQ ID NO: 15:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

CATGGGCAGC TCGAG                                                         15

(2) INFORMATION FOR SEQ ID NO: 16:
```

(i) SEQUENCE CHARACTERISTICS:
    (A) LENGTH: 42 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 16:

GAGGGTTGTG GGTGTCGCTA GTGAGTCGAC TACAGCAAAAT T        42

(2) INFORMATION FOR SEQ ID NO: 17:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

GGATGTGGGT GCCGCTGACT CTAGAGTCGA CGGAATTC        38

(2) INFORMATION FOR SEQ ID NO: 18:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

AATTCACCAT GATTCCTGGT AACCGAATGC T        31

(2) INFORMATION FOR SEQ ID NO: 19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

CATTC GGTTACCAGG AATCATGGTG        25

(2) INFORMATION FOR SEQ ID NO: 20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

CGACCTGCAG CCACCATGCATCT GACTGTA        30

(2) INFORMATION FOR SEQ ID NO: 21:

(i) SEQUENCE CHARACTERISTICS:
        (A) LENGTH: 27 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO: 21:

TGCCTGCAGT TTAATATTAG TGGCAGC                                                27

(2) INFORMATION FOR SEQ ID NO: 22:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

CGACCTGCAG CCACC                                                             15

(2) INFORMATION FOR SEQ ID NO: 23:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 23:

TCGACCCACC ATGCCGGGGC TGGGGCGGAG GGCGCAGTGG CTGTGCTGGT GGTGGGGGCT            60

GTGCTGCAGC TGCTGCGGGC C                                                      81

(2) INFORMATION FOR SEQ ID NO: 24:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 24:

CGCAGCAGCT GCACAGCAGC CCCCACCACC AGCACAGCCA CTGCGCCCTC CGCCCCAGCC            60

CCGGCATGGT GGG                                                               73

(2) INFORMATION FOR SEQ ID NO: 25:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 25:

TCGACTGGTT T                                                                 11

(2) INFORMATION FOR SEQ ID NO: 26:

(i) SEQUENCE CHARACTERISTICS:
        (A) LENGTH: 9 base pairs
        (B) TYPE: nucleic acid
        (C) STRANDEDNESS: single

```
        (D) TOPOLOGY: linear (ii) MOLECULE TYPE: DNA (genomic)

(xi) SEQUENCE DESCRIPTION: SEQ ID NO: 26:

CGAAACCAG                                                                    9

(2) INFORMATION FOR SEQ ID NO: 27:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 27:

TCGACAGGCT CGCCTGCA                                                         18

(2) INFORMATION FOR SEQ ID NO: 28:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 28:

GGCGAGCCTG                                                                  10

(2) INFORMATION FOR SEQ ID NO: 29:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 29:

CAGGTCGACC CACCATGCAC GTGCGCTCA                                             29

(2) INFORMATION FOR SEQ ID NO: 30:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 30:

TCTGTCGACC TCGGAGGAGC TAGTGGC                                               27
```

RECOMBINANT BONE MORPHOGENETIC PROTEIN HETERODIMERS, COMPOSITIONS AND METHODS OF USE

CROSS REFERENCE TO RELATED APPLICATIONS

The application is a divisional of Ser. No. 08/469,411 filed Jun. 6, 1995, now U.S. Pat. No. 6,190,880, which is a continuation of Ser. No. 07/989,847, filed Nov. 27, 1992, now U.S. Pat. No. 5,866,364, which is a continuation-in-part of Ser. No. 07/864,692, filed Apr. 7, 1992, now abandoned, which is a continuation in part of Ser. No. 07/787,496, filed Nov. 4, 1991, now abandoned.

FIELD OF THE INVENTION

The present invention relates to a series of novel recombinant heterodimeric proteins useful in the field of treating bone defects, healing bone injury and in wound healing in general. The invention also relates to methods for obtaining these heterodimers, methods for producing them by recombinant genetic engineering techniques, and compositions containing them.

BACKGROUND OF THE INVENTION

In recent years, protein factors which are characterized by bone or cartilage growth inducing properties have been isolated and identified. See, e.g., U.S. Pat. No. 5,013,649, PCT published application WO90/11366; PCT published application WO91/05802 and the variety of references cited therein. See, also, PCT/US90/05903 which discloses a protein sequence termed OP-1, which is substantially similar to human BMP-7, and has been reported to have osteogenic activity.

A family of individual bone morphogenetic proteins (BMPs), termed BMP-2 through BMP-9 have been isolated and identified. Incorporated by reference for the purposes of providing disclosure of these proteins and methods of producing them are co-owned U.S. Pat. No. 6,150,328 and the related applications recited in its preamble. Of particular interest, are the proteins termed BMP-2 and BMP-4, disclosed in the above-referenced application; BMP-7, disclosed in U.S. Pat. No. 5,141,905; BMP-5, disclosed in U.S. Pat. No. 5,106,748 and Ser. No. 356,033, now abandoned; and BMP-6, disclosed in Ser. No. 370,544, now abandoned, and Ser. No. 347,559, now abandoned; and BMP-8, disclosed in Ser. No. 525,357, now abandoned. Additional members of the BMP family include BMP-1, disclosed in U.S. Pat. No. 6,432,919; BMP-9, disclosed in Ser. No. 720,590, now abandoned; and BMP-3, disclosed in Ser. No. 179,197, now abandoned, and PCT publication 89/01464. These applications are incorporated herein by reference for disclosure of these BMPs.

There remains a need in the art for other proteins and compositions useful in the fields of bone and wound healing.

SUMMARY OF THE INVENTION

In one aspect, the invention provides a method for producing a recombinant heterodimeric protein having bone stimulating activity comprising culturing a selected host cell containing a polynucleotide sequence encoding a first selected BMP or fragment thereof and a polynucleotide sequence encoding a second selected BMP or fragment thereof. The resulting co-expressed, biologically active heterodimer is isolated from the culture medium.

According to one embodiment of this invention, the host cell may be co-transfected with one or more vectors containing coding sequences for one or more BMPs. Each BMP polynucleotide sequence may be present on the same vector or on individual vectors transfected into the cell. Alternatively, the BMPs or their fragments may be incorporated into a chromosome of the host cell. Additionally, a single transcription unit may encode single copy of two genes encoding a different BMP.

According to another embodiment of this invention, the selected host cell containing the two polypeptide encoding sequences is a hybrid cell line obtained by fusing two selected, stable host cells, each host cell transfected with, and capable of stably expressing, a polynucleotide sequence encoding a selected first or second BMP or fragment thereof.

In another aspect of the present invention, therefore, there are provided recombinant heterodimeric proteins comprising a protein or fragment of a first BMP in association with a protein or fragment of a second BMP. The heterodimer may be characterized by bone stimulating activity. The heterodimers may comprise a protein or fragment of BMP-2 associated with a protein or fragment of either BMP-5, BMP-6, BMP-7 or BMP-8; or a protein or fragment of BMP-4 associated with a protein or fragment of either BMP-5, BMP-6, BMP-7 or BMP-8. In further embodiments the heterodimers may comprise a protein or fragment of BMP-2 associated with a protein or fragment of either BMP-1, BMP-3 or BMP-4. BMP-4 may also form a heterodimer in association with BMP-1, BMP-2 or a fragment thereof. Still further embodiments may comprise heterodimers involving combinations of BMP-5, BMP-6, BMP-7 and BMP-8. For example, the heterodimers may comprise BMP-5 associated with BMP-6, BMP-7 or BMP-8; BMP-6 associated with BMP-7 or BMP-8; or BMP-7 associated with BMP-8. These heterodimers may be produced by co-expressing each protein in a selected host cell and isolating the heterodimer from the culture medium.

As a further aspect of this invention a cell line is provided which comprises a first polynucleotide sequence encoding a first BMP or fragment thereof and a second polynucleotide sequence encoding a second BMP or fragment thereof, the sequences being under control of one or more suitable expression regulatory systems capable of co-expressing the BMPs as a heterodimer. The cell line may be transfected with one or more than one polynucleotide molecule. Alternatively, the cell line may be a hybrid cell line created by cell fusion as described above.

Another aspect of the invention is a polynucleotide molecule or plasmid vector comprising a polynucleotide sequence encoding a first selected BMP or fragment thereof and a polynucleotide sequence encoding a second selected BMP or fragment thereof. The sequences are under the control of at least one suitable regulatory sequence capable of directing co-expression of each protein or fragment. The molecule may contain a single transcription unit containing a copy of both genes, or more than one transcription unit, each containing a copy of a single gene.

As still another aspect of this invention there is provided a method for producing a recombinant dimeric or heterodimeric protein having bone stimulating activity in a prokaryotic cell comprising culturing a selected host cell containing a polynucleotide sequence encoding a first selected BMP or fragment thereof; culturing a second selected host cell containing a polynucleotide sequence encoding a second selected BMP or fragment thereof; isolating monomeric forms of each BMP protein from the culture medium and co-assembling a monomer of the first protein with a monomer of the second protein. The first protein and the second protein may be the same or different BMPs. The resulting biologically active dimer or heterodimer is thereafter isolated from the mixture. Preferred cells are E. coli.

Thus, as further aspects of this invention recombinant BMP dimers or heterodimers produced in eukaryotic cells are provided, as well as suitable vectors or plasmids, and selected transformed cells useful in such a production method.

Other aspects and advantages of the present invention are described further in the following detailed description of preferred embodiments of the present invention.

BRIEF DESCRIPTION OF THE FIGURES

FIGS. 1A–1C provides the DNA and amino acid sequences of human BMP-2 (SEQ ID NOs: 1 and 2).

FIGS. 2A–2C provides the DNA and amino acid sequences of human BMP-4 (SEQ ID NOs: 3 and 4).

FIGS. 3A–3C provides the DNA and amino acid sequences of human BMP-7 (SEQ ID NOs: 5 and 6).

FIGS. 4A–4E provides the DNA and amino acid sequences of human BMP-6 (SEQ ID NOs: 7 and 8).

FIGS. 5A–5D provides the DNA and amino acid sequences of human BMP-5 (SEQ ID NOs: 9 and 10).

FIGS. 6A–6B provides the DNA and amino acid sequences of human BMP-8 (SEQ ID NOs: 11 and 12).

FIGS. 7A–7C provides the DNA sequence of vector pALB2-781 containing the mature portion of the BMP-2 gene (SEQ ID NOs: 13 and 14).

FIGS. 11A–11C depicts BMP-3 DNA and amino acid sequence.

FIGS. 13A–13B provides a comparison of the in vivo activity of BMP-2/6 and BMP-2.

FIGS. 14A–14B provides a comparison of BMP-2, BMP-6 and BMP-2/6 in vivo activity.

DETAILED DESCRIPTION OF THE INVENTION

Figure 8:
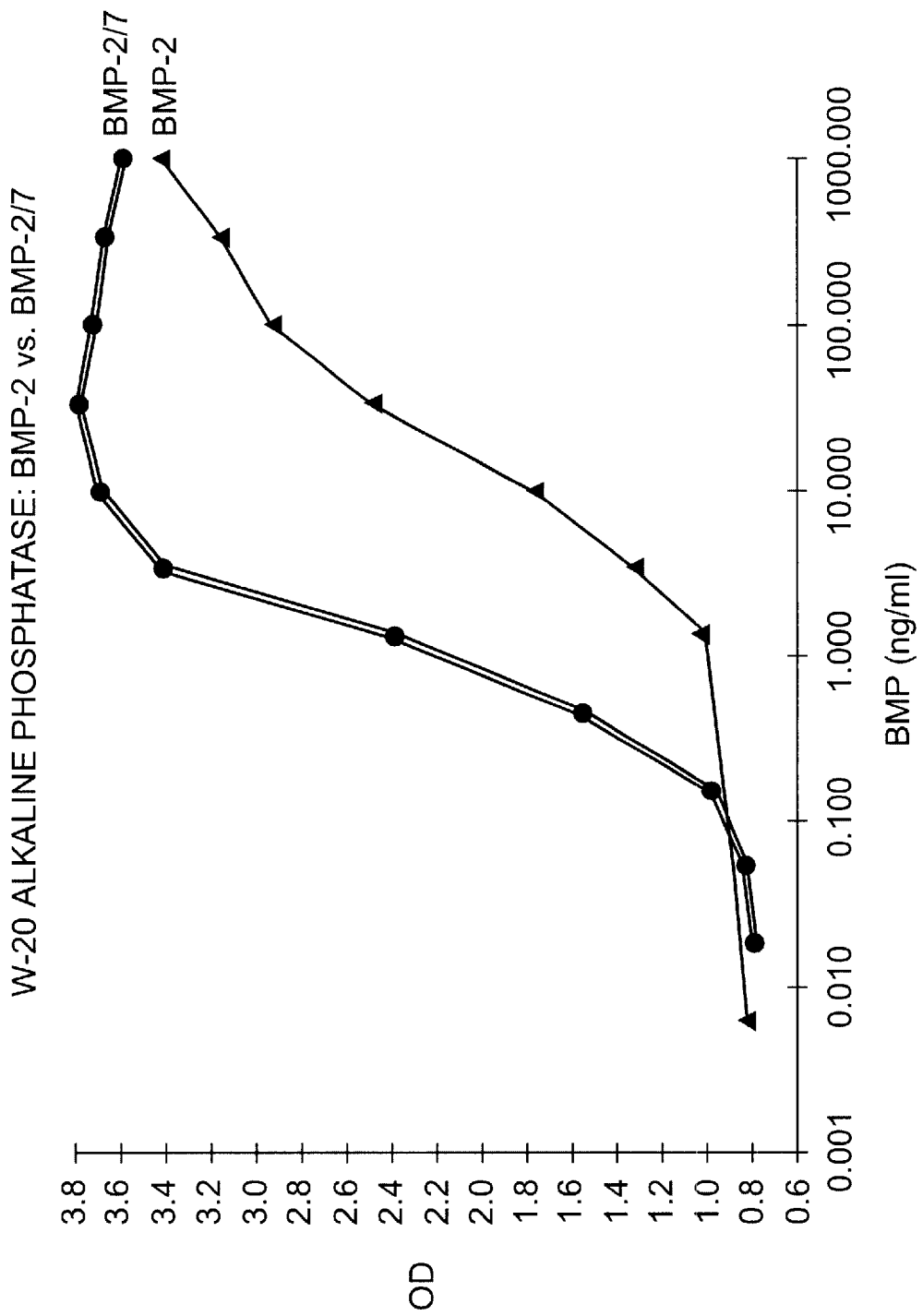
FIG. 8 compares the activity of CHO BMP-2 and CHO BMP-2/7 in the W20 alkaline phosphatase assay.

The present invention provides a method for producing recombinant heterodimeric proteins having bone stimulating activity, as well as the recombinant heterodimers themselves, and compositions containing them for bone-stimulating or repairing therapeutic use.

As used throughout this document, the term 'heterodimer' is defined as a biologically-active protein construct comprising the association of two different BMP protein monomers or active fragments thereof joined through at least one covalent, disulfide linkage. A heterodimer of this invention may be characterized by the presence of between one to seven disulfide linkages between the two BMP component strands.

According to the present invention, therefore, a method for producing a recombinant BMP heterodimer according to this invention comprises culturing a selected host cell containing a polynucleotide sequence encoding a first selected BMP or a biologically active fragment thereof and a polynucleotide sequence encoding a second selected BMP or a fragment thereof. The resulting co-expressed, biologically active heterodimer is formed within the host cell, secreted therefrom and isolated from the culture medium. Preferred embodiments of methods for producing the heterodimeric proteins of this invention, are described in detail below and in the following examples. Preferred methods of the invention involve known recombinant genetic engineering techniques [See, e.g., Sambrook et al, "Molecular Cloning. A Laboratory Manual.", 2d edition, Cold Spring Harbor Laboratory, Cold Spring Harbor, N.Y. (1989)]. However, other methods, such as conventional chemical synthesis may also be useful in preparing a heterodimer of this invention.

BMP heterodimers generated by this method are produced in a mixture of homodimers and heterodimers. This mixture of heterodimers and homodimers may be separated from contaminants in the culture medium by resort to essentially conventional methods, such as classical protein biochemistry or affinity antibody columns specific for one of the BMPs making up the heterodimer. Additionally, if desired, the heterodimers may be separated from homodimers in the mixture. Such separation techniques allow unambiguous determination of the activity of the heterodimeric species. Example 4 provides one presently employed purification scheme for this purpose.

Preferably the recombinant heterodimers of this invention produced by these methods involve the BMPs designated human BMP-2, human BMP-4, human BMP-5, human BMP-6, human BMP-7 and BMP-8. However, BMP-3 has also been determined to form an active heterodimer with BMP-2. Other species of these BMPs as well as BMPs than those specifically identified above may also be employed in heterodimers useful for veterinary, diagnostic or research use. However, the human proteins, specifically those proteins identified below, are preferred for human pharmaceutical uses.

Human BMP-2 is characterized by containing substantially the entire sequence, or fragments, of the amino acid sequence and DNA sequence disclosed in FIG. 1. Human BMP-2 proteins are further characterized as disulfide-linked dimers and homodimers of mature BMP-2 subunits. Recombinantly-expressed BMP-2 subunits include protein species having heterogeneous amino termini. One BMP-2 subunit is characterized by comprising amino acid #249 (Ser)–#396 (Arg) of FIG. 1 (SEQ ID NOs: 1 and 2). Another BMP-2 subunit is characterized by comprising amino acid #266 (Thr)–#396 (Arg) of FIG. 1. Another BMP-2 subunit is characterized by comprising amino acid #296 (Cys)–#396 (Arg) of FIG. 1. A mature BMP-2 subunit is characterized by comprising amino acid #283 (Gln)–#396 (Arg) of FIG. 1. This latter subunit is the presently most abundant protein species which results from recombinant expression of BMP-2 (FIG. 1). However, the proportions of certain species of BMP-2 produced may be altered by manipulating the culture conditions. BMP-2 may also include modifications of the sequences of FIG. 1, e.g., deletion of amino acids #241–280 and changing amino acid #245 Arg to Ile, among other changes.

As described in detail in U.S. Pat. No. 6,150,328, incorporated by reference herein, human BMP-2 may be produced by culturing a cell transformed with a DNA sequence comprising the nucleotide coding sequence from nucleotide #356 to #1543 in FIG. 1 and recovering and purifying from the culture medium one or more of the above-identified protein species, substantially free from other proteinaceous materials with which it is co-produced. Human BMP-2 proteins are characterized by the ability to induce bone formation. Human BMP-2 also has in vitro activity in the W20 bioassay. Human BMP-2 is further characterized by the ability to induce cartilage formation. Human BMP-2 may be further characterized by the ability to demonstrate cartilage and/or bone formation activity in the rat bone formation assay described in the above-referenced application.

Human BMP-4 is characterized by containing substantially the entire sequence, or fragments, of the amino acid sequence and DNA sequence disclosed in FIG. 2 (SEQ ID NOs: 3 and 4). Human BMP-4 proteins are further characterized as disulfide-linked dimers and homodimers of mature BMP-4 subunits. Recombinantly-expressed BMP-4 subunits may include protein species having heterogeneous amino termini. A mature subunit of human BMP-4 is characterized by an amino acid sequence comprising amino acids #293 (Ser)–#408 (Arg) of FIG. 2. Other amino termini of BMP-4 may be selected from the sequence of FIG. 2. Modified versions of BMP-4, including proteins further truncated at the amino or carboxy termini, may also be constructed by resort to conventional mutagenic techniques.

As disclosed in above-incorporated U.S. Pat. No. 6,150, 328, BMP-4 may be produced by culturing a cell transformed with a DNA sequence comprising the nucleotide coding sequence from nucleotide #403 to nucleotide #1626 in FIG. 2 and recovering and purifying from the culture medium a protein containing the amino acid sequence from amino acid #293 to #408 as shown in FIG. 2, substantially free from other proteinaceous materials with which it is co-produced. BMP-4 proteins are capable of inducing the formation of bone. BMP-4 proteins are capable of inducing formation of cartilage. BMP-4 proteins are further characterized by the ability to demonstrate cartilage and/or bone formation activity in the rat bone formation assay.

Human BMP-7 is characterized by containing substantially the entire sequence, or fragments, of the amino acid sequence and DNA sequence disclosed in FIG. 3. Human BMP-7 proteins are further characterized as disulfide-linked dimers and homodimers of mature BMP-7 subunits. Recombinantly-expressed BMP-7 subunits include protein species having heterogeneous amino termini. One BMP-7 subunit is characterized by comprising amino acid #293 (Ser)–#431 (His) of FIG. 3. (SEQ ID NOs: 5 and 6). This subunit is the most abundantly formed protein produced by recombinant expression of the BMP-7 sequence. Another-BMP-7 subunit is characterized by comprising amino acids #300 (Ser)–#431 (His) of FIG. 3. Still, another BMP-7 subunit is characterized by comprising amino acids #316 (Ala)–#431 (His) of FIG. 3. Other amino termini of BMP-7 may be selected from the sequence of FIG. 3. Similarly, modified versions, including proteins further truncated at the amino or carboxy termini, of BMP-7 may also be constructed by resort to conventional mutagenic techniques.

As disclosed in above-incorporated U.S. Pat. No. 5,141, 905, BMP-7 may be produced by culturing a cell transformed with a DNA sequence comprising the nucleotide coding sequence from nucleotide #97 to nucleotide #1389 in FIG. 3 and recovering and purifying from the culture medium a protein containing the amino acid sequence from amino acid #293 to #431 as shown in FIG. 3, substantially free from other proteinaceous or contaminating materials with which it is co-produced. These proteins are capable of stimulating, promoting, or otherwise inducing cartilage and/or bone formation.

Human BMP-6 is characterized by containing substantially the entire sequence, or fragments, of the amino acid sequence and DNA sequence disclosed in FIG. 4. Human BMP-6 proteins are further characterized as disulfide-linked dimers of mature BMP-6 subunits. Recombinantly-expressed BMP-6 subunits may include protein species having heterogeneous amino termini. One BMP-6 subunit is characterized by comprising amino acid #375 (Ser)–#513 (His) of FIG. 4 (SEQ ID NOs: 7 and 8). Other amino termini of BMP-6 may be selected from the sequence of FIG. 4. Modified versions, including proteins further truncated at the amino or carboxy termini of BMP-6 may also be constructed by resort to conventional mutagenic techniques.

As described in detail in U.S. Pat. No. 5,187,076, incorporated by reference herein, human BMP-6 may be produced by culturing a cell transformed with a DNA sequence comprising the nucleotide coding sequence from nucleotide #160 to #1698 in FIG. 4 and recovering and purifying from the culture medium a protein comprising amino acid #375 to #513 of FIG. 4, substantially free from other proteinaceous materials or other contaminating materials with which it is co-produced. Human BMP-6 may be further characterized by the ability to demonstrate cartilage and/or bone formation activity in the rat bone formation assay.

Human BMP-5 is characterized by containing substantially the entire sequence, or fragments, of the amino acid sequence and DNA sequence disclosed in FIG. 5 (SEQ ID NOs: 9 and 10). Human BMP-5 proteins are further characterized as disulfide-linked dimers of mature BMP-5 subunits. Recombinantly-expressed BMP-5 subunits may include protein species having heterogeneous amino termini. One BMP-5 subunit is characterized by comprising amino acid #329 (Ser)–#454 (His) of FIG. 5. Other amino termini of BMP-5 may be selected from the sequence of FIG. 5. Modified versions, including proteins further truncated at the amino or carboxy termini, of BMP-5 may also be constructed by resort to conventional mutagenic techniques.

As described in detail in U.S. patent application Ser. No. 588,227, now abandoned, incorporated by reference herein, human BMP-5 may be produced by culturing a cell transformed with a DNA sequence comprising the nucleotide coding sequence from nucleotide #701 to #2060 in FIG. 5 and recovering and purifying from the culture medium a protein comprising amino acid #329 to #454 of FIG. 5, substantially free from other proteinaceous materials or other contaminating materials with which it is co-produced. Human BMP-5 may be further characterized by the ability to demonstrate cartilage and/or bone formation activity in the rat bone formation assay described in the above-referenced application.

Human BMP-8 is characterized by containing substantially the entire sequence, or fragments, of the amino acid sequence and DNA sequence disclosed in FIG. 6. Human BMP-8 proteins may be further characterized as disulfide-linked dimers of mature BMP-8 subunits. Recombinantly-expressed BMP-8 subunits may include protein species having heterogeneous amino termini. A BMP-8 sequence or subunit sequence comprises amino acid #143 (Ala)–#281 (His) of FIG. 6 (SEQ ID NOs: 11 and. 12). Other amino termini of BMP-8 may be selected from the sequence of FIG. 6. Modified versions, including proteins further truncated at the amino or carboxy termini, of BMP-8 may also be constructed by resort to conventional mutagenic techniques.

As described generally in U.S. patent application Ser. No. 525,357, now abandoned, incorporated by reference herein, and as further described herein, human BMP-8 may be produced by culturing a cell transformed with a DNA sequence comprising the nucleotide coding sequence from nucleotide #1 to #850 in FIG. 6 and recovering and purifying from the culture medium a protein comprising amino acid #143 to #281 of FIG. 6, or similar amino acid sequences with heterogenous N-termini, substantially free from other proteinaceous materials or other contaminating materials with which it is co-produced. This BMP-8 may also be produced in *E. coli* by inserting into a vector the sequence encoding amino acid #143 to 281 of FIG. 6 with a Met inserted before amino acid #143. Human BMP-8 may be further characterized by the ability to demonstrate cartilage and/or bone formation activity in the rat bone formation assay.

Each above described BMP protein in its native, non-reduced dimeric form may be further characterized by an apparent molecular weight on a 12% Laemmli gel ranging between approximately 28 kD to approximately 40 kD. Analogs or modified versions of the DNA and amino acid sequences described herein which provide proteins or active fragments displaying bone stimulating or repairing activity in the rat bone formation assay described below in Example 9, are also classifed as suitable BMPs for use in this invention, further provided that the proteins or fragments contain one or more Cys residues for participation in disulfide linkages. Useful modifications of these sequences may be made by one of skill in the art with resort to known recombinant genetic engineering techniques. Production of these BMP sequences in mammalian cells produces homodimers, generally mixtures of homodimers having heterologous N termini. Production of these BMP sequences in *E.coli* produces monomeric protein species.

Thus, according to this invention one recombinant heterodimer of the present invention comprises the association of a human BMP-2, including, e.g., a monomeric strand from a mature BMP-2 subunit as described above or an active fragment thereof, bound through one or up to seven covalent, disulfide linkages to a human BMP-5 including, e.g., a monomeric strand from a mature BMP-5 subunit as described above or an active fragment thereof. Another recombinant heterodimer of the present invention comprises the association of a human BMP-2, as described above, bound through one or up to seven covalent, disulfide linkages to a human BMP-6, including, e.g., a monomeric strand from a BMP-6 subunit as described above or an active fragment thereof. Another recombinant heterodimer of the present invention comprises the association of a human BMP-2, as described above, bound through one or up to seven covalent, disulfide linkages to a human BMP-7, including, e.g., a monomeric strand of a BMP-7 subunit as described above or an active fragment thereof. Another recombinant heterodimer of the present invention comprises the association of a human BMP-2, as described above, bound through one or up to seven covalent, disulfide linkages to a human BMP-8, including, e.g., a monomeric strand of a BMP-8 subunit as described above or an active fragment thereof.

Still another recombinant heterodimer of the present invention comprises the association of a human BMP-4, including, e.g., a monomeric strand of a BMP-4 subunit as described above or an active fragment thereof, bound through one or up to seven covalent, disulfide linkages to a human BMP-5, as described above. Another recombinant heterodimer of the present invention comprises the association of a human BMP-4, as described above, bound through one or more covalent, disulfide linkages to a human BMP-6, as described above. Another recombinant heterodimer of the present invention comprises the association of a human BMP-4, as described above bound through one or more covalent, disulfide linkages to a human BMP-7, as described above. Another recombinant heterodimer of the present invention comprises the association of a human BMP-4, as described above, bound through one or more covalent, disulfide linkages to a human BMP-8, as described above.

A further recombinant heterodimer of the present invention comprises the association of a human BMP-2, including, e.g., a monomeric strand from a mature BMP-2 subunit as described above or an active fragment thereof, bound through at least one disulfide linkage to a human BMP-3 including, e.g., a monomeric strand from a mature BMP-3 subunit as described above or an active fragment thereof. Another recombinant heterodimer of the present invention comprises the association of a human BMP-2, as described above, bound through at least one disulfide linkage to a human BMP-4, including, e.g., a monomeric strand from a BMP-4 subunit as described above or an active fragment thereof. Another recombinant heterodimer of the present invention comprises the association of a human BMP-5, as described above, bound through at least one disulfide linkage to a human BMP-6, including, e.g., a monomeric strand of a BMP-6 subunit as described above or an active fragment thereof. Another recombinant heterodimer of the present invention comprises the association of a human BMP-5, as described above, bound through at least one disulfide linkage to a human BMP-7, including, e.g., a monomeric strand of a BMP-7 subunit as described above or an active fragment thereof. In addition, human BMP-5 may be associated with human BMP-8 bound through at least one disulfide linkage to a human BMP-8 subunit or active fragment thereof.

Still another recombinant heterodimer of the present invention comprises the association of a human BMP-6, including, e.g., a monomeric strand of a BMP-6 subunit as described above or an active fragment thereof, bound through at least one disulfide linkage to a human BMP-7, as described above. Another recombinant heterodimer of the present invention comprises the association of a human BMP-6, as described above, bound through one or more covalent, disulfide linkages to a human BMP-8, as described above. Another recombinant heterodimer of the present invention comprises the association of a human BMP-7, as described above bound through one or more covalent, disulfide linkages to a human BMP-8, as described above.

The disulfide linkages formed between the monomeric strands of the BMPs may occur between one Cys on each strand. Disulfide linkages may form between two Cys on each BMP. Disulfide linkages may form between three Cys on each BMP. Disulfide linkages may form between four Cys on each BMP. Disulfide linkages may form between five Cys on each BMP. Disulfide linkages may form between six Cys on each BMP. Disulfide linkages may form between seven Cys on each BMP. These disulfide linkages may form between adjacent Cys on each BMP or between only selected Cys interspersed within the respective protein sequence. Various heterodimers having the same BMP component strands may form with different numbers of disulfide linkages. Various heterodimers having the same BMP component strands may form with disulfide bonds at different Cys locations. Different heterodimers encompassed by this invention having the same BMP components may differ based upon their recombinant production in mammalian cells, bacterial cells, insect or yeast cells.

These recombinant heterodimers may be characterized by increased alkaline phosphatase activity in the W20 mouse stromal cell line bioassay (Example 8) compared to the individual BMP homodimers, one strand of which forms each heterodimer. Further, these heterodimers are characterized by greater activity in the W20 bioassay than is provided by simple mixtures of the individual BMP dimers. Preliminary characterization of heterodimers measured on the W20 bioassay have demonstrated that heterodimers of BMP-2 with BMP-5, BMP-6 or BMP-7 are very active. Similarly, heterodimers of BMP-4 with BMP-5, BMP-6 or BMP-7 are strongly active in the W20 bioassay..

Heterodimers of this invention may also be characterized by activity in bone growth and stimulation assays. For example, a heterodimer of this invention is also active in the rat bone formation assay described below in Example 9. The heterodimers are also active in the osteocalcin bioassay described in Example 8. Other characteristics of a heterodimer of this invention include co-precipitation with anti-BMP antibodies to the two different constituent BMPs, as well as characteristic results on Western blots, high pressure liquid chromatography (HPLC) and on two-dimensional gels, with and without reducing conditions.

One embodiment of the method of the present invention for producing recombinant BMP heterodimers involves culturing a suitable cell line, which has been co-transfected with a DNA sequence coding for expression of a first BMP or fragment thereof and a DNA sequence coding for expression of a second BMP or fragment thereof, under the control of known regulatory sequences. The transformed host cells are cultured and the heterodimeric protein recovered and purified from the culture medium.

In another embodiment of this method which is the presently preferred method of expression of the heterodimers of this invention, a single host cell, e.g., a CHO DUKX cell, is co-transfected with a first DNA molecule containing a DNA sequence encoding one BMP and a second DNA molecule containing a DNA sequence encoding a second selected BMP. One or both plasmids contain a selectable marker that can be used to establish stable cell lines expressing the BMPs. These separate plasmids containing distinct BMP genes on seperate transcription units are mixed and transfected into the CHO cells using conventional protocols. A ratio of plasmids that gives maximal expression of activity in the W20 assay, generally, 1:1, is determined.

For example, as described in detail in Example 3, equal ratios of a plasmid containing the first BMP and a dihydrofolate reductase (DHFR) marker gene and another plasmid containing a second BMP and a DHFR marker gene can be co-introduced into DHFR-deficient CHO cells, DUKX-BII, by calcium phosphate coprecipitation and transfection, electroporation, microinjection, protoplast fusion or lipofection. Individual DHFR expressing transformants are selected for growth in alpha media with dialyzed fetal calf serum by conventional means. DHFR+ cells containing increased gene copies can be selected for propagation in increasing concentrations of methotrexate (MTX) (e.g. sequential steps in 0.02, 0.1, 0.5 and 2.0 uM MTX) according to the procedures of Kaufman and Sharp, *J. Mol. Biol.*, 159:601–629 (1982); and Kaufman et al, *Mol. Cell Biol.*, 5:1750 (1983). Expression of the heterodimer or at least one BMP linked to DHFR should increase with increasing levels of MTX resistance. Cells that stably express either or both BMP/DHFR genes will survive. However at a high frequency, cell lines stably incorporate and express both plasmids that were present during the initial transfection. The conditioned medium is thereafter harvested and the heterodimer isolated by conventional methods and assayed for activity. This approach can be employed with DHFR-deficient cells.

As an alternative embodiment of this method, a DNA molecule containing one selected BMP gene may be transfected into a stable cell line which already expresses another selected BMP gene. For example as described in detail in Example 3 below, a stable CHO cell line expressing BMP-7 with the DHFR marker (designated 7MB9) [Genetics Institute, Inc] is transfected with a plasmid containing BMP-2 and a second selectable marker gene, e.g., neomycin resistance (Neo). After transfection, the cell is cultured and suitable cells selected by treatment with MTX and the antibiotic, G-418. surviving cells are then screened for the expression of the heterodimer. This expression system has the advantage of permitting a single step selection.

Alternative dual selection strategies using different cell lines or different markers can also be used. For example, the use of an adenosine deaminase (ADA) marker to amplify the second BMP gene in a stable CHO cell line expressing a different BMP with the DHFR marker may be preferable, since the level of expression can be increased using deoxycoformycin (DCF)-mediated gene amplification. (See the ADA containing plasmid described in Example 1). Alternatively, any BMP cell line made by first using this marker can then be the recipient of a second BMP expression vector containing a distinct marker and selected for dual resistance and BMP coexpression.

Still another embodiment of a method of expressing the heterodimers of this invention includes transfecting the host cell with a single DNA molecule encoding multiple genes for expression either on a single transcription unit or on separate transcription units. Multicistronic expression involves multiple polypeptides encoded within a single transcript, which can be efficiently translated from vectors utilizing a leader sequence, e.g., from the EMC virus, from poliovirus, or from other conventional sources of leader sequences. Two BMP genes and a selectable marker can be expressed within a single transcription unit. For example, vectors containing the configuration BMPx-EMC-BMPy-DHFR or BMPx-EMC-BMPy-EMC-DHFR can be transfected into CHO cells and selected and amplified using the DHFR marker. A plasmid may be constructed which contains DNA sequences encoding two different BMPs, one or more marker genes and a suitable leader or regulatory sequence on a single transcription unit.

Similarly, host cells may be transfected with a single plasmid which contains separate transcription units for each BMP. A selectable marker, e.g., DHFR, can be contained on a another transcription unit, or alternatively as the second cistron on one or both of the BMP genes. These plasmids may be transfected into a selected host cell for expression of the heterodimer, and the heterodimer isolated from the cells or culture medium as described above.

Another embodiment of this expression method involves cell fusion. Two stable cell lines which express selected BMPs, such as a cell line expressing BMP-2 (e.g., 2EG5) and a cell line expressing BMP-7 (e.g., 7MB9), developed using the DHFR/MTX gene amplification system and expressing BMP at high levels, as described in Example 1 and in the above incorporated U.S. applications, can be transfected with one of several dominant marker genes (e.g., neo$^r$, hygromycin$^r$, GPT) After sufficient time in coculture (approximately one day) one resultant cell line expressing one BMP and a dominant marker can be fused with a cell line expressing a different BMP and preferably a different marker using a fusigenic reagent, such as polyethylene glycol, Sendai virus or other known agent.

The resulting cell hybrids expressing both dominant markers and DHFR can be selected using the appropriate culture conditions, and screened for coexpression of the BMPs or their fragments. The selected hybrid cell contains sequences encoding both selected BMPs, and the heterodimer is formed in the cell and then secreted. The heterodimer is obtained from the conditioned medium and isolated and purified therefrom by conventional methods (see e.g., Example 4). The resulting heterodimer may be characterized by methods described herein.

Cell lines generated from the approaches described above can be used to produce co-expressed, heterodimeric BMP polypeptides. The heterodimeric proteins are isolated from the cell medium in a form substantially free from other proteins with which they are co-produced as well as from other contaminants found in the host cells by conventional purification techniques. The presently preferred method of production is co-transfection of different vectors into CHO cells and methotrexate-mediated gene amplification. Stable cell lines may be used to generate conditioned media containing recombinant BMP that can be purified and assayed for in vitro and in vivo activities. For example, the resulting heterodimer-producing cell lines obtained by any of the methods described herein may be screened for activity by the assays described in Examples 8 and 9, RNA expression, and protein expression by sodium dodecyl sulfate polyacrylamide gel electrophoresis (SDS-PAGE).

The above-described methods of co-expression of the heterodimers of this invention utilize suitable host cells or cell lines. Suitable cell preferably include mammalian cells, such as Chinese hamster ovary cells (CHO). The selection of suitable mammalian host cells and methods for transformation, culture, amplification, screening and product production and purification are known in the art. See, e.g., Gething and Sambrook, *Nature,* 293:620–625 (1981), or alternatively, Kaufman et al, *Mol. Cell. Biol.,* 5(7): 1750–1759 (1985) or Howley et al, U.S. Pat. No. 4,419,446. Other suitable mammalian cell lines are the CV-1 cell line, BHK cell lines and the 293 cell line. The monkey COS-1 cell line is presently believed to be inefficient in BMP heterodimer production.

Many strains of yeast cells known to those skilled in the art may also be available as host cells for expression of the polypeptides of the present invention, e.g., *Saccharomyces cerevisiae.* Additionally, where desired, insect cells may be utilized as host cells in the method of the present invention. See, e.g., Miller et al, *Genetic Engineering,* 8:277–298 (Plenum Press 1986) and references cited therein.

Another method for producing a biologically active heterodimeric protein of this invention may be employed where the host cells are microbial, preferably bacterial cells, in particular *E. coli.* For example, the various strains of *E. coli* (e.g., HB101, MC1061) are well-known as host cells in the field of biotechnology. Various strains of *B. subtilis, Pseudomonas,* other bacilli and the like may also be employed in this method.

This method, which may be employed to produce monomers and. dimers (both homodimers and heterodimers) is described in European Patent Application No. 433,225, incorporated herein by reference. Briefly, this process involves culturing a microbial host comprising a nucleotide sequence encoding the desired BMP protein linked in the proper reading frame to an expression control sequence which permits expression of the protein and recovering the monomeric, soluble protein. Where the protein is insoluble in the host cells, the water-insoluble protein fraction is isolated from the host cells and the protein is solubilized. After chromatographic purification, the solubilized protein is subjected to selected conditions to obtain the biologically active dimeric configuration of the protein. This process, which may be employed to produce the heterodimers of this invention, is described specifically in Example 7, for the production of a BMP-2 homodimer.

Another aspect of the present invention provides DNA molecules or plasmid vectors for use in expression of these recombinant heterodimers. These plasmid vectors may be constructed by resort to known methods and available components known to those of skill in the art. In general, to generate a vector useful in the methods of this invention, the DNA encoding the desired BMP protein is transferred into one or more appropriate expression vectors suitable for the selected host cell.

It is presently contemplated that any expression vector suitable for efficient expression in mammalian cells may be employed to produce the recombinant heterodimers of this invention in mammalian host cells. Preferably the vectors contain the selected BMP DNA sequences described above and in the Figures, which encode selected BMP components of the heterodimer. Alternatively, vectors incorporating modified sequences as described in the above-referenced patent applications are also embodiments of the present invention and useful in the production of the vectors.

In addition to the specific vectors described in Example 1, one skilled in the art can construct mammalian expression vectors by employing the sequence of FIGS. 1–6 or other DNA sequences containing the coding sequences of FIGS. 1–6 (SEQ ID NOs: 1, 3, 5, 7, 9 and 11), or other modified sequences and known vectors, such as pCD [Okayama et al, *Mol. Cell Biol.,* 2:161–170 (1982)] and pJL3, pJL4 [Gough et al, *EMBO J.,* 4:645–653 (1985)]. The BMP DNA sequences can be modified by removing the non-coding nucleotides on the 5' and 3' ends of the coding region. The deleted non-coding nucleotides may or may not be replaced by other sequences known to be beneficial for expression. The transformation of these vectors into appropriate host cells as described above can produce desired heterodimers.

One skilled in the art could manipulate the sequences of FIGS. 1–6 by eliminating or replacing the mammalian regulatory sequences flanking the coding sequence with e.g., yeast or insect regulatory sequences, to create vectors for intracellular or extracellular expression by yeast or insect cells. [See, e.g., procedures described in published European Patent Application 155,476] for expression in insect cells; and procedures described in published PCT application WO86/00639 and European Patent Application EPA 123, 289 for expression in yeast cells).

Similarly, bacterial sequences and preference codons may replace sequences in the described and exemplified mammalian vectors to create suitable expression systems for use in the production of BMP monomers in the method described above. For example, the coding sequences could be further manipulated (e.g. ligated to other known linkers or modified by deleting non-coding sequences therefrom or altering nucleotides therein by other known techniques). The modified BMP coding sequences could then be inserted into a known bacterial vector using procedures such as described in T. Taniguchi et al, *Proc. Natl. Acad. Sci. USA,* 77:5230–5233 (1980). The exemplary bacterial vector could then be transformed into bacterial host cells and BMP heterodimers expressed thereby. An exemplary vector for microbial, e.g., bacterial, expression is described below in Example 7.

Other vectors useful in the methods of this invention may contain multiple genes in a single transcription unit. For example, a proposed plasmid p7E2D contains the BMP-7 gene followed by the EMC leader sequence, followed by the BMP-2 gene, followed by the DHFR marker gene. Another example is plasmid p7E2ED which contains the BMP-7 gene, the EMC leader, the BMP-2 gene, another EMC leader sequence and the DHFR marker gene. Alternatively, the vector may contain more than one transcription unit. As one example, the plasmid p2ED7ED contains a transcription unit for BMP-2 and a separate transcription unit for BMP-7, i.e., BMP-2-EMC-DHFR and BMP-7-EMC-DHFR. Alternatively, each transcription unit on the plasmid may contain a different marker gene. For example, plasmid p2EN7ED contains BMP-2-EMC-Neo and BMP-7-EMC-DHFR.

Additionally the vectors also contain appropriate expression control sequences which are capable of directing the replication and expression of the BMP in the selected host cells. Useful regulatory sequences for such vectors are known to one of skill in the art and may be selected depending upon the selected host cells. Such selection is routine and does not form part of the present invention. Similarly, the vectors may contain one or more selection markers, such as the antibiotic resistance gene, Neo or selectable markers such as DHFR and ADA. The presently preferred marker gene is DHFR. These marker genes may also be selected by one of skill in the art.

Once they are expressed by one of the methods described above, the heterodimers of this invention may be identified and characterized by application of a variety of assays and procedures. A co-precipitation (immunoprecipitation) assay may be performed with antibodies to each of the BMPs forming the heterodimer. Generally antibodies for this use may be developed by conventional means, e.g., using the selected BMP, fragments thereof, or synthetic BMP peptides as antigen. Antibodies employed in assays are generally polyclonal antibodies made from individual BMP peptides or proteins injected into rabbits according to classical techniques. This assay is performed conventionally, and permits the identification of the heterodimer, which is precipitated by antibodies to both BMP components of the heterodimer. In contrast, only one of the two antibodies causes precipitation of any homodimeric form which may be produced in the process of producing the heterodimer.

Another characterizing assay is a Western assay, employing a precipitating antibody, a probing antibody and a detecting antibody. This assay may also be performed conventionally, by using an antibody to one of the BMPs to precipitate the dimers, which are run on reducing SDS-PAGE for Western analysis. An antibody to the second BMP is used to probe the precipitates on the Western gel for the heterodimer. A detecting antibody, such as a goat-antirabbit antibody labelled with horseradish peroxidase (HRP), is then applied, which will reveal the presence of one of the component subunits of the heterodimer.

Finally, the specific activity of the heterodimer may be quantitated as described in detail in Example 6. Briefly, the amount of each BMP is quantitated using Western blot analysis or pulse labelling and SDS-PAGE analysis in samples of each BMP homodimer and the heterodimer. The W20 activity is also determined as described specifically in Example 8. The relative specific activities may be calculated by the formula: W20 alkaline phosphatase activity/amount of BMP on Western blot or by fluorography. As one example, this formula has been determined for the BMP-2/7 heterodimer, demonstrating that the heterodimer has an estimated 5 to 50 fold higher specific activity than the BMP-2 homodimer.

The heterodimers of the present invention may have a variety of therapeutic and pharmaceutical uses, e.g., in compositions for wound healing, tissue repair, and in similar compositions which have been indicated for use of the individual BMPs. Increased potency of the heterodimers over the individual BMPs may permit lower dosages of the compositions in which they are contained to be administered to a patient in comparison to dosages of compositions containing only a single BMP. A heterodimeric protein of the present invention, which induces cartilage and/or bone growth in circumstances where bone is not normally formed, has application in the healing of bone fractures and cartilage defects in humans and other animals. Such a preparation employing a heterodimeric protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A heterodimeric protein of this invention may be used in the treatment of periodontal disease, and in other tooth repair processes. Such agents may provide an environment to attract bone-forming cells, stimulate growth of bone-forming cells or induce differentiation of progenitors of bone-forming cells. Heterodimeric polypeptides of the invention may also be useful in the treatment of osteoporosis. A variety of osteogenic, cartilage-inducing and bone inducing factors have been described. See, e.g., European Patent Applications 148,155 and 169,016 for discussions thereof.

The proteins of the invention may also be used in wound healing and related tissue repair. The types of wounds include, but are not limited to burns, incisions and ulcers. (See, e.g., PCT Publication WO84/01106 incorporated by reference herein for discussion of wound healing and related tissue repair).

Additionally, the proteins of the invention may increase neuronal survival and therefore be useful in transplantation and treatment of conditions exhibiting a decrease in neuronal survival.

In view of the usefulness of the heterodimers, therefore, a further aspect of the invention is a therapeutic method and composition for repairing fractures and other conditions related to cartilage and/or bone defects or periodontal diseases. In addition, the invention comprises therapeutic methods and compositions for wound healing and tissue repair. Such compositions comprise a therapeutically effective amount of a heterodimeric protein of the invention in admixture with a pharmaceutically acceptable vehicle, carrier or matrix. The preparation and formulation of such physiologically acceptable protein compositions, having due regard to pH, isotonicity, stability and the like, is within the skill of the art.

It is expected that the proteins of the invention may act in concert with other related proteins and growth factors. Therapeutic methods and compositions of the invention therefore comprise a therapeutic amount of a heterodimeric protein of the invention with a therapeutic amount of at least one of the other BMP proteins disclosed in co-owned and concurrently filed U.S. applications described above. Such combinations may comprise separate molecules of the BMP proteins or other heteromolecules of the present invention.

In further compositions, heterodimeric proteins of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-α and TGF-β), and insulin-like growth factor (IGF).

The therapeutic compositions are also presently valuable for veterinary applications due to the lack of species specificity in BMP proteins. Particularly domestic animals and thoroughbred horses, in addition to humans, are desired patients for such treatment with heterodimeric proteins of the present invention.

The therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than the heterodimeric proteins of the invention which may also optionally be included in the composition as described above, may alternatively or additionally, be administered simultaneously or sequentially with the heterodimeric BMP composition in the methods of the invention. Preferably for bone and/or cartilage formation, the composition would include a matrix capable of delivering the heterodimeric protein-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the heterodimeric BMP compositions will define the appropriate formulation. Potential matrices for the compositions may be biodegradable and chemically defined calcium sulfate, tricalciumphosphate, hydroxyapatite, polylactic acid, polyglycolic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

Presently preferred is a 50:50 (mole weight) copolymer of lactic acid and glycolic acid in the form of porous particles having diameters ranging from 150 to 800 microns. In some applicatons, it will be useful to utilize a sequestering agent, such as carboxymethyl cellulose or autologous blood clot, to prevent the BMP compositions from dissassociating from the matrix.

The dosage regimen of a heterodimeric protein-containing pharmaceutical composition will be determined by the attending physician considering various factors which modify the action of the heterodimeric proteins, e.g. amount of bone weight desired to be formed, the site of bone damage, the condition of the damaged bone, the size of a wound, type of damaged tissue, the patient's age, sex, and diet, the severity of any infection, time of administration and other clinical factors. The dosage may vary with the type of matrix used in the reconstitution and the BMP proteins in the heterodimer and any additional BMP or other proteins in the pharmaceutical composition. For example, the addition of other known growth factors, such as IGF I (insulin like growth factor I), to the final composition, may also effect the dosage. Progress can be monitored by periodic assessment of bone growth and/or repair, for example, X-rays, histomorphometric determinations and tetracycline labeling.

The following examples are illustrative of the present invention and do not limit its scope.

EXAMPLE 1

BMP Vector Constructs and Cell Lines

A. BMP-2 Vectors

The mammalian expression vector pMT2 CXM is a derivative of p91023 (b) [Wong et al, Science, 228:810–815 (1985)] differing from the latter in that it contains the ampicillin resistance gene (Amp) in place of the tetracycline resistance gene (Tet) and further contains a XhoI site for insertion of cDNA clones. The functional elements of pMT2 CXM have been described [R. J. Kaufman, *Proc. Natl. Acad. Sci. USA*, 82:689–693 (1985)] and include the adenovirus VA genes, the SV40 origin of replication including the 72 bp enhancer, the adenovirus major late promoter including a 5' splice site and the majority of the adenovirus tripartite leader sequence present on adenovirus late mRNAs, a 3' splice acceptor site, a DHFR insert, the SV40 early polyadenylation site (SV40), and pBR322 sequences needed for propagation in *E. coli*.

EcoRI digestion of pMT2-VWF, which has been deposited with the American Type Culture Collection (ATCC), Rockville, Md. (USA) under accession number ATCC 67122, excises the cDNA insert present in pMT2-VWF, yielding pMT2 in linear form. Plasmid pMT2 can be ligated and used to transform *E. coli* HB 101 or DH-5 to ampicillin resistance. Plasmid pMT2 DNA can be prepared by conventional methods.

Plasmid pMT2 CXM is then constructed using loopout/in mutagenesis [Morinaga et al, *Biotechnoloqy*, 84:636 (1984)]. This removes bases 1075 to 1145 relative to the HindIII site near the SV40 origin of replication and enhancer sequences of pMT2. In addition it inserts the following sequence:

5' PO$_4$-CATGGGCAGCTCGAG-3'    (SEQ ID NO: 15)

at nucleotide 1145. This sequence contains the recognition site for the restriction endonuclease XhoI.

A derivative of pMT2 CXM, termed plasmid pMT23, contains recognition sites for the restriction endonucleases PstI, EcoRI, SalI and XhoI.

Full length BMP-2 cDNA (FIG. 1) (SEQ ID NO: 1) is released from the λGT10 vector by digestion with EcoRI and subcloned into pSP65 [Promega Biotec, Madison, Wis.; see, e.g., Melton et al, *Nucl. Acids Res.*, 12:7035–7056 (1984)] in both orientations yielding pBMP-2 #39-3 or pBMP-2 #39-4.

The majority of the untranslated regions of the BMP-2 cDNA are removed in the following manner. The 5' sequences are removed between the SalI site in the adapter (present from the original cDNA cloning) and the SalI site 7 base pairs upstream of the initiator ATG by digestion of the pSP65 plasmid containing the BMP-2 cDNA with SalI and religation. The 3' untranslated region is removed using heteroduplex mutagenesis using the oligonucleotide

```
                                         (SEQ ID NO: 16)
5' GAGGGTTGTGGGTGTCGCTAGTGAGTCGACTACAGCAAAATT 3'.
                    End       SalI
```

The sequence contains the terminal 3' coding region of the BMP-2 cDNA, followed immediately by a recognition site for SalI. The sequence introduces a SalI site following the termination (TAG) codon.

The SalI fragment of this clone was subcloned into the expression vector pMT23, yielding the vector pMT23-BMP2ΔUT. Restriction enzyme sites flank the BMP-2 coding region in the sequence PstI-EcoRI-SalI-BMP-2 cDNA-SalI-EcoRI-XhoI.

The expression plasmid pED4 [Kaufman et al, *Nucl. Acids Res.*, 19:4485–4490 (1991)) was linearized by digestion with EcoRI and treated with calf intestinal phosphatase. The BMP-2 cDNA gene was excised from pMT23-BMP2ΔUT by digestion with EcoRI and recovery of the 1.2 kb fragment by electrophoresis through a 1.0% low melt agarose gel. The linearized pED4 vector and the EcoRI BMP-2 fragment were ligated together, yielding the BMP-2 expression plasmid pBMP2Δ-EMC.

Another vector pBMP-2Δ-EN contains the same sequences contained within the vector pBMP2Δ-EMC, except the DHFR gene has been replaced by conventional means with the neomycin resistance gene from the Tn5 transposable element.

B. BMP4 Vectors

A BMP-4 cDNA sequence set forth in FIG. 2 (SEQ ID NO: 3), in which the 3' untranslated region is removed, is made via heteroduplex mutagenesis with the mutagenic oligonucleotide:

```
                                          (SEQ ID NO: 17)
5' GGATGTGGGTGCCGCTGACTCTAGAGTCGACGGAATTC 3'
                    End              EcoRI
```

This deletes all of the sequences 3' to the translation terminator codon of the BMP-4 cDNA, juxtaposing this terminator codon and the vector polylinker sequences. This step is performed in an SP65 vector (Promega Biotech) and may also be conveniently performed in pMT2-derivatives containing the BMP-4 cDNA similar to the BMP2 vectors described above. The 5' untranslated region is removed using the restriction endonuclease BsmI, which cleaves within the eighth codon of BMP-4 cDNA.

Reconstruction of the first eight codons is accomplished by ligation to oligonucleotides:

```
                                          (SEQ ID NO: 18)
      EcoRI  Initiator           BsmI
5' AATTCACCATGATTCCTGGTAACCGAATGCT 3' and
                                          (SEQ ID NO: 19)
3'       GTGGTACTAAGGACCATTGGCTTAC   5'
```

These oligonucleotides form a duplex which has a BsmI complementary cohesive end capable of ligation to the BsmI restricted BMP-4 cDNA, and it has an EcoRI complementary cohesive end capable of ligation to the EcoRI restricted vector pMT2. Thus the cDNA for BMP-4 with the 5' and 3' untranslated regions deleted, and retaining the entire encoding sequence is contained within an EcoRI restriction fragment of approximately 1.2 kb.

The pMT2 CXM plasmid containing this BMP-4 sequence is designated pXMBMP-4ΔUT. It is digested with EcoRI in order to release the BMP-4 cDNA containing insert from the vector. This insert is subcloned into the EcoRI site of the mammalian expression vector pED4, resulting pBMP4Δ-EMC.

C. BMP-5 Vectors

A BMP-5 cDNA sequence comprising the nucleotide sequence from nucleotide #699 to #2070 of FIG. 5 (SEQ ID NO: 9) is specifically amplified as follows. The oligonucleotides CGACCTGCAGCCACCATGCATCTGACTGTA (SEQ ID NO: 20) and TGCCTGCAGTTTAATATTAGTG-GCAGC (SEQ ID NO: 21) are utilized as primers to allow the amplification of nucleotide sequence #699 to #2070 of FIG. 5 from the BMP-5 insert of λ-ZAP clone U2-16 [ATCC #68109]. This procedure introduces the nucleotide sequence CGACCTGCAGCCACC (SEQ ID NO: 22) immediately preceeding nucleotide #699 and the nucleotide sequence CTGCAGGCA immediately following nucleotide #2070. The addition of these sequences results in the creation of PstI restriction endonuclease recognition sites at both ends of the amplified DNA fragment. The resulting amplified DNA product of this procedure is digested with the restriction endonuclease PstI and subcloned into the PstI site of the pMT2 derivative pMT21 [Kaufman, *Nucl. Acids Res.*, 19:4485–4490 (1991)]. The resulting clone is designated H5/5/pMT.

The insert of H5/5/pMT is excised by PstI digestion and subcloned into the plasmid vector pSP65 [Promega Biotech] at the PstI site, resulting in plasmid BMP5/SP6. BMP5/SP6 and U2-16 are digested with the restriction endonucleases NsiI and NdeI to excise the portion of their inserts corresponding to nucleotides #704 to #1876 of FIG. 5. The resulting 1173 nucleotide NsiI-NdeI fragment of clone U2-16 is ligated into the NsiI-NdeI site of BMP5/SP6 from which the corresponding 1173 nucleotide NsiI-NdeI fragment had been removed. The resulting clone is designated BMP5mix/SP65.

Direct DNA sequence analysis of BMP5mix/SP65 is performed to confirm identity of the nucleotide sequences produced by the amplification to those set forth in FIG. 5. The clone BMP5mix/SP65 is digested with the restriction endonuclease PstI resulting in the excision of an insert comprising the nucleotides #699 to #2070 of FIG. 5 and the additional sequences containing the PstI recognition sites as described above. The resulting 1382 nucleotide PstI fragment is subcloned into the PstI site of the pMT2 derivative pMT21. This clone is designated BMP5mix/pMT21#2.

The same fragment is also subcloned into the PstI site of pED4 to yield the vector designated BMP5mix-EMC-11.

D. BMP-6 vectors

BMP-6 cDNA sequence comprising the nucleotide sequence from nucleotide #160 to #1706 of FIG. 4 (SEQ ID NO: 7) is produced by a series of techniques known to those skilled in the art. The clone BMP6C35 [ATCC 68245] is digested with the restriction endonucleases ApaI and TaqI, resulting in the excision of a 1476-nucleotide portion of the insert comprising nucleotide #231 to #1703 of FIG. 4. Synthetic oligonucleotides with SalI restriction endonuclease site converters are designed to replace those nucleotides corresponding to #160 to #230 and #1704 to #1706 which are not contained in the 1476 ApaI-TaqI fragment of the BMP-6 cDNA sequence.

Oligonucleotide/SalI converters conceived to replace the missing 5' (TCGACCCACCATGCCGGGGCTGGGGCGGAGGGC GCAGTGGCTGTGCTGGTGGTGGGGGCTGTGCTG CAGCTGCTGCGGGCC (SEQ ID NO: 23) and CGCAGC AGCTGCACAGCAGCCCCCACCACCAGCACAGCC ACTGCGCCCTCCGCCCCA GCCCCGGCATGGTGGG) (SEQ ID NO: 24) and 3' (TCGACTGGTTT (SEQ ID NO: 25) and CGAAACCAG (SEQ ID NO: 26) ) sequences are annealed to each other independently. The annealed 5' and 3' converters are then ligated to the 1476 nucleotide ApaI-TaqI described above, creating a 1563 nucleotide fragment comprising the nucleotide sequence from #160 to #1706 of FIG. 4 and the additional sequences contrived to create SalI restriction endonuclease sites at both ends. The resulting 1563 nucleotide fragment is subcloned into the SalI site of pSP64 [Promega Biotech, Madison, Wis.]. This clone is designated BMP6/SP64#15.

DNA sequence analysis of BMP6/SP64#15 is performed to confirm identity of the 5' and 3' sequences replaced by the converters to the sequence set forth in FIG. 4. The insert of BMP6/SP64#15 is excised by digestion with the restriction endonuclease SalI. The resulting 1563 nucleotide SalI fragment is subcloned into the XhoI restriction endonuclease site of pMT21 and designated herein as BMP6/pMT21.

The PstI site of pED4 is converted to a SalI site by digestion of the plasmid with PstI and ligation to the converter oligonucleotides:

5'-TCGACAGGCTCGCCTGCA-3'    (SEQ ID NO: 27)    and

3'-GTCCGAGCGG-5'             (SEQ ID NO: 28).

The above 1563 nucleotide SalI fragment is also subcloned into the SalI site of this pED4 vector, yielding the expression vector BMP6/EMC.

E. BMP-7 Vectors

A BMP-7 sequence comprising the nucleotide sequence from nucleotide #97 to #1402 of FIG. 3 (SEQ ID NO: 5) is specifically amplified as follows. The oligonucleotides CAGGTCGACCCACCATGCACGTGCGCTCA (SEQ ID NO: 29) and TCTGTCGACCTCGGAGGAGCTAGTGGC (SEQ ID NO: 30) are utilized as primers to allow the amplification of nucleotide sequence #97 to #1402 of FIG. 3 from the insert of clone PEH7-9 [ATCC #68182]. This procedure generates the insertion of the nucleotide sequence CAGGTCGACCCACC immediately preceeding nucleotide #97 and the insertion of the nucleotide sequence GTCGA-CAGA immediately following nucleotide #1402. The addition of these sequences results in the creation of a SalI restriction endonuclease recognition site at each end of the amplified. DNA fragment. The resulting amplified DNA product of this procedure is digested with the restriction endonuclease SalI and subcloned into the SalI site of the plasmid vector pSP64 [Promega Biotech, Madison, Wis.] resulting in BMP7/SP6#2.

The clones BMP7/SP6#2 and PEH7-9 are digested with the restriction endonucleases NcoI and StuI to excise the portion of their inserts corresponding to nucleotides #363 to #1081 of FIG. 3. The resulting 719 nucleotide NcoI-StuI fragment of clone PEH7-9 is ligated into the NcoI-StuI site of BMP7/SP6#2 from which the corresponding 719 nucleotide fragment is removed. The resulting clone is designated BMP7mix/SP6.

Direct DNA sequence analysis of BMP7mix/SP6 confirmed identity of the 3' region to the nucleotide sequence from #1082 to #1402 of FIG. 3, however the 5' region contained one nucleotide misincorporation.

Amplification of the nucleotide sequence (#97 to #1402 of FIG. 3) utilizing PEH7-9 as a template is repeated as described above. The resulting amplified DNA product of this procedure is digested with the restriction endonucleases SalI and PstI. This digestion results in the excision of a 747 nucleotide fragment comprising nucleotide #97 to #833 of FIG. 3 plus the additional sequences of the 5' priming oligonucleotide used to create the SalI restriction endonuclease recognition site described earlier. This 747 SalI-PstI fragment is subcloned into a SalI-PstI digested pSP65 [Promega Biotech, Madison, Wis.] vector resulting in 5'BMP7/SP65. DNA sequence analysis demonstrates that the insert of the 5'BMP7/SP65#1 comprises a sequence identical to nucleotide #97 to #362 of FIG. 3.

The clones BMP7mix/SP6 and 5'BMP7/SP65 are digested with the restriction endonucleases SalI and NcoI. The resulting 3' NcoI-SalI fragment of BMP7mix/SP6 comprising nucleotides #363 to #1402 of FIG. 3 and 5' SalI-NcoI fragment of 5'BMP7/SP65 comprising nucleotides #97 to #362 of FIG. 3 are ligated together at the NcoI restriction sites to produce a 1317 nucleotide fragment comprising nucleotides #97 to #1402 of FIG. 3 plus the additional sequences derived from the 5' and 3' oligonucleotide primers which allows the creation of SalI restriction sites at both ends of this fragment.

This 1317 nucleotide SalI fragment is ligated nto the SalI site of the pMT2 derivative pMT2Cla-2. pMT2Cla-2 is constructed by digesting pMT21 with EcoRV and XhoI, treating the digested DNA with Klenow fragment of DNA polymerase I and ligating ClaI linkers (NEBio Labs, CATCGATG). This removes bases 2171 to 2420 starting from the HindIII site near the SV40 origin of replication and enhancer sequences of pMT2 and introduces a unique ClaI site, but leaves the adenovirus VAI gene intact, resulting in pMT2Cla-2. This clone is designated BMP-7-pMT2.

The insert of BMP-7-pMT2 is excised by digestion with the restriction endonuclease SalI. The resulting 1317 nucleotide SalI fragment is subcloned into the XhoI restriction endonuclease site of pMT21 to yield the clone BMP-7/pMT21. This SalI fragment is also subcloned into the SalI site of the pED4 vector in which the PstI site was converted into a SalI site- as described above, resulting in the vector pBMP7/EMC#4.

F. BMP-8 Vectors

At present no mammalian BMP-8 vectors have been constructed. However, using the sequence of FIG. 6 (SEQ ID NO: 11), it is contemplated that vectors similar to those described above for the other BMPs may be readily constructed. A bacterial expression vector similar to the BMP-2 vector described in detail in Example 7 may also be constructed for BMP-8, by introducing a Met before the amino acid #284 Ala of FIG. 6. This sequence of BMP-8 is inserted into the vector pALBP2-781 in place of the BMP-2 sequence. See Example 7.

G. BMP Vectors containing the Adenosine Deaminase (Ada) Marker

BMP genes were inserted into the vector pMT3SV2Ada [R. J. Kaufman, Meth. Enz., 185:537–566 (1990)] to yield expression plasmids containing separate transcription units for the BMP cDNA gene and the selectable marker Ada. pMT3SV2Ada contains a polylinker with recognition sites for the enzymes PstI, EcoRI, SalI and XbaI that can be used for insertion of and expression of genes (i.e. BMP) in mammalian cells. In addition, the vector contains a second transcription unit encoding Ada which serves as a dominant and amplifiable marker in mammalian cells.

To construct expression vectors for BMP-5, BMP-6 and BMP-7, individually, the same general method was employed. The gene for BMP 5 (FIG. 5), 6 (FIG. 4) or 7

(FIG. 3) was inserted into the polylinker essentially as described above for the pED4 vector. These vectors can be used for transfection into CHO DUKX cells and subsequent selection and amplification using the Ada marker as previously described [Kaufman et al, *Proc. Natl. Acad. Sci. USA*, 83:3136–3140 (1986)]. Since each such vector does not contain a DHFR gene, the resultant transformed cells remain DHFR negative and can be subsequently transfected with a second vector containing a different BMP in conjunction with DHFR and amplified with methotrexate.

Alternatively, the pMT3SV2Ada/BMP vectors can be used to transfect stable CHO cell lines previously transfected with a different BMP gene and amplified using the DHFR/methotrexate system. The resultant transfectants can be subsequently amplified using the Ada system, yielding cell lines that coexpress two different BMP genes, and are amplified using both the DHFR and Ada markers.

H. BMP-Expressing Mammalian Cell Lines

At present, the most desirable mammalian cell lines for use in producing the recombinant homodimers and heterodimers of this invention are the following. These cell lines were prepared by conventional transformation of CHO cells using vectors described above.

The BMP-2 expressing cell line 2EG5 is a CHO cell stably transformed with the vector pBMP2delta-EMC.

The BMP-4 expressing cell line 4E9 is a CHO cell stably transformed with the vector pBMP4delta-EMC.

The BMP-5 expressing cell line 5E10 is a CHO cell stably transformed with the vector BMP5mix-EMC-11 (at a amplification level of 2 micromolar MTX).

The BMP-6 expressing cell line 6HG8 is a CHO cell stably transformed with the vector BMP6/EMC.

The BMP-7 expressing cell line 7MB9 is a CHO cell stably transformed with the vector BMP7/pMT21.

EXAMPLE 2

Transient Expression of BMP Heterodimers

The heterodimers of the present invention may be prepared by co-expression in a transient expression system for screening in the assays of Example 8 by two different techniques as follows.

In the first procedure, the pMT2-derived and EMC-derived -expression plasmids described in Example 1 and other similarly derived vectors were constructed which encoded, individually, BMP-2 through BMP-7, and transforming growth factor-beta (TGFβ1). All combinations of pairs of plasmids were mixed in equal proportion and used to co-transfect CHO cells using the DEAE-dextran procedure [Sompayrac and Danna, *Proc. Natl. Acad. Sci. USA*, 78:7575–7578 (1981); Luthman and Magnusson, *Nucl. Acids Res.*, 11:1295–1308 (1983)]. The cells are grown in alpha Minimal Essential Medium (α-MEM) supplemented with 10% fetal bovine serum, adenosine, deoxyadenosine, thymidine (100 μg/ml each), pen/strep, and glutamine (1 mM).

The addition of compounds such as heparin, suramin and dextran sulfate are desirable in growth medium to increase the amounts of BMP-2 present in the conditioned medium of CHO cells. Similarly responsive to such compounds is BMP-5. Therefore, it is expected that these compounds will be added to growth medium for any heterodimer containing these BMP components. Other BMPs may also be responsive to the effects of these compounds, which are believed to inhibit the interaction of the mature BMP molecules with the cell surface.

The following day, fresh growth medium, with or without 100 μg/ml heparin, was added. Twenty-four hours later, conditioned medium was harvested.

In some experiments, the conditioned medium was collected minus heparin for the 24–48 hour period post-transfection, and the same plates were then used to generate conditioned medium in the presence of heparin 48–72 hour post-transfection. Controls included transfecting cells with expression plasmids lacking any BMP sequences, transfecting cells with plasmids containing sequences for only a single BMP, or mixing conditioned medium from cells transfected with a single BMP with conditioned medium from cells transfected with a different BMP.

Characterizations of the coexpressed heterodimer BMPs in crude conditioned media, which is otherwise not purified, provided the following results. Transiently coexpressed BMP was assayed for induction of alkaline phosphatase activity on W20 stromal cells, as described in Example 8.

Co-expression of BMP-2 with BMP-5, BMP-6 and BMP-7, and BMP-4 with BMP-5, BMP-6 and BMP-7 yielded more alkaline phosphatase inducing activity in the W20 assay than either of the individual BMP homodimers alone or mixtures of-homodimers, as shown below. Maximal activity (in vitro), was obtained when BMP-2 was coexpressed with BMP-7. Increased activity was also found the heterodimers BMP-2/5; BMP-2/6; BMP-4/5; BMP-4/6; and BMP-4/7.

|       | TGF-β | BMP-7 | BMP-6 | BMP-5 | BMP-4 | BMP-3 | BMP-2 |
|-------|-------|-------|-------|-------|-------|-------|-------|
|       |       |       | Condition Medium |   |   |   |   |
| BMP-2 | 33    | 240   | 99    | 89    | 53    | 9     | 29    |
| BMP-3 | —     | —     | —     | —     | 14    | —     |       |
| BMP-4 | 12    | 115   | 25    | 22    | 24    |       |       |
| BMP-5 | —     | —     | —     | —     |       |       |       |
| BMP-6 | —     | —     | —     |       |       |       |       |
| BMP-7 | —     | —     |       |       |       |       |       |
| TGF-β | —     |       |       |       |       |       |       |
|       |       |       | Condition Medium + heparin |   |   |   |   |
| BMP-2 | 88    | 454   | 132   | 127   | 70    | 77    | 169   |
| BMP-3 | —     | —     | —     | —     | 7     | —     |       |
| BMP-4 | 7     | 119   | 30    | 41    | 37    |       |       |
| BMP-5 | —     | —     | —     | —     |       |       |       |
| BMP-6 | —     | —     | —     |       |       |       |       |

-continued

| | TGF-β | BMP-7 | BMP-6 | BMP-5 | BMP-4 | BMP-3 | BMP-2 |
|---|---|---|---|---|---|---|---|
| BMP-7 | — | — | | | | | |
| TGF-β | — | | | | | | |

Units: 1 unit of activity is equivalent to that of 1 ng/ml of rhBMP-2.
—: indicates activity below the detection limit of the assay.

These BMP combinations were subsequently expressed using various ratios of expression plasmids (9:1, 3:1, 1:1, 1:3, 1:9) during the CHO cell transient transfection. The performance of this method using plasmids containing BMP-2 and plasmids containing BMP-7 at plasmid number ratios ranging from 9:1 to 1:9, respectively, demonstrated that the highest activity in the W20 assay was obtained when approximately the same number of plasmids of each BMP were transfected into the host cell. Ratios of BMP-2 to BMP-7 plasmids of 3:1 to 1:3, respectively, also resulted in increased activity in W20 assay in comparison to host cells transfected with plasmids containing only a single BMP. However, these latter ratios produced less activity than the 1:1 ratio.

Similar ratios may be determined by one of skill in the art for heterodimers consisting of other than BMP-2 and BMP-7. For example, preliminary work on the heterodimer formed between BMP-2 and BMP-6 has indicated that a preferred ratio of plasmids for co-transfection is 3:1, respectively. The determination of preferred ratios for this method is within the skill of the art.

As an alternative means to transiently generate coexpressed BMPs, the stable CHO cell lines identified in Example 1 expressing each BMP-2, BMP-4, BMP-5, BMP-6 and BMP-7, are cocultured for one day, and are then fused with 46.7% polyethylene glycol (PEG). One day post-fusion, fresh medium is added and the heterodimers are harvested 24 hours later for the W20 assay, described in Example 8. The assay results were substantially similar to those described immediately above.

Therefore, all combinations of BMP-2 or 4 coexpressed with either BMP-5, 6 or 7 yielded greater activity than any of the BMP homodimers alone. In control experiments where each BMP homodimer was expressed alone and conditioned media mixed post harvest, the activity was always intermediate between the individual BMPs, demonstrating that the BMP co-expressed heterodimers yield higher activity than combinations of the individually expressed BMP homodimers.

EXAMPLE 3

Table Expression of BMP Heterodimers

A. BMP-2/7

Based on the results of the transient assays in Example 2, stable cell lines were made that co-express BMP-2 and BMP-7.

A preferred stable cell line, 2E7E-10, was obtained as follows: Plasmid DNA (a 1:1 mixture of PBMP-7-EMC and pBMP-2-EMC, described in Example 1) is transfected into CHO cells by electroporation [Neuman et al, *EMBO J.*, 1:841–845 (1982)].

Two days later, cells are switched to selective medium containing 10% dialyzed fetal bovine serum and lacking nucleosides. Colonies expressing DHFR are counted 10–14 days later. Individual colonies or pools of colonies are expanded and analyzed for expression of each heterodimer BMP component RNA and protein using standard procedures and are subsequently selected for amplification by growth in increasing concentrations of MTX. Stepwise selection of the preferred clone, termed 2E7E,. is carried out up to a concentration of 0.5 $\mu$M MTX. The cell line is then subcloned and assayed for heterodimer 2/7 expression.

Procedures for such assay include Western blot analysis to detect the presence of the component DNA, protein analysis and SDS-PAGE analysis of metabolically labelled protein, W20 assay, and analysis for cartilage and/or bone formation activity using the ectopic rat bone formation assay of Example 9. The presently preferred clonally-derived cell line is identified as 2E7E-10. This cell line secretes BMP-2/7 heterodimer proteins into the media containing 0.5 $\mu$M MTX.

The CHO cell line 2E7E-10 is grown in Dulbecco's modified Eagle's medium (DMEM)/Ham's nutrient mixture F-12, 1:1 (vol/vol), supplemented with 10% fetal bovine serum. When the cells are 80 to 100% confluent, the medium is replaced with serum-free DMEM/F-12. Medium is harvested every 24 hours for 4 days. For protein production and purification the cells are cultured serum-free.

While the co-expressing cell line 2E7E-10 preliminarily appears to make lower amounts of BMP protein than the BMP2-expressing cell line 2EG5 described in Example 2, preliminary evidence suggests that the specific activity of the presumptive heterodimer is at least 5-fold greater than BMP-2 homodimer (see Example 6).

To construct another heterodimer producing cell line, the stable CHO cell line 7MB9, previously transfected with pBMP-7-pMT2, and which expresses BMP-7, is employed. 7MB9 may be amplified and selected to 2 $\mu$M methotrexate resistance using the DHFR/MTX system. To generate a stable co-expressing cell line, cell line 7MB9 is transfected with the expression vector pBMP-2Δ-EN (EMC-Neo) containing BMP-2 and the neomycin resistance gene from the Tn5 transposable element. The resulting transfected stable cell line was selected for both G-418 and MTX resistance. Individual clones were picked and analyzed for BMP expression, as described above.

It is anticipated that stable cell lines co-expressing other combinations of BMPs which show enhanced activity by transient coexpression will likewise yield greater activity upon stable expression.

B. BMP-2/6.

Based on the results of the transient assays in Example 2, stable cell lines were made that co-express BMP-2 and BMP-6.

A preferred stable cell line, 12C07, was obtained as follows: Plasmid DNA (a 1:3 mixture of PBMP-6-EMC and pBMP-2-EMC, described in Example 1) is transfected into CHO cells by electroporation [Neuman et al, *EMBO J.*, 1:841–845 (1982)).

Two days later, cells are switched to selective medium containing 10% dialyzed fetal bovine serum and lacking nucleosides. Colonies expressing DHFR are counted 10–14 days later. Individual colonies or pools of colonies are expanded and analyzed for expression of each heterodimer BMP component RNA and protein using standard procedures and are subsequently selected for amplification by growth in increasing concentrations of MTX. Stepwise selection of the preferred clone, termed 12-C, is carried out up to a concentration of 2.0 $\mu$M MTX. The cell line is then subcloned and assayed for heterodimer 2/6 expression.

Procedures for such assay include Western blot analysis to detect the presence of the component DNA, protein analysis and SDS-PAGE analysis of metabolically labelled protein, W20 assay, and analysis for cartilage and/or bone formation activity using the ectopic rat bone formation assay of Example 9. The presently preferred clonally-derived cell line is identified as 12C07. This cell line secretes BMP-2/6 heterodimer proteins into the media containing 2.0 $\mu$M MTX.

The CHO cell line 12C07 is grown in Dulbecco's modified Eagle's medium (DMEM)/Ham's nutrient mixture F-12, 1:1 (vol/vol), supplemented with 10% fetal bovine serum. When the cells are 80 to 100% confluent, the medium is replaced with serum-free DMEM/F-12. Medium is harvested every: 24 hours for 4 days. For protein production and purification the cells are cultured serum-free.

While the co-expressing cell line 12C07 preliminarily appears to make lower amounts of BMP protein than the BMP2-expressing cell line 2EG5 described in Example 2, preliminary evidence suggests that the specific activity of the presumptive heterodimer is at least 3–5-fold greater than BMP-2 homodimer (see Example 6).

To construct another heterodimer producing cell line, the stable CHO cell line 2EG5, previously transfected with pBMP-2-EMC, and which expresses BMP-2, is employed. 2EG5 may be amplified and selected to 2 $\mu$M methotrexate resistance using the DHFR/MTX system. To generate a stable co-expressing cell line, cell line 2EG5 is transfected with the expression vector pBMP-6-ada (ada deaminase) containing BMP-6 and the ADA resistance gene. The resulting transfected stable cell line was selected for both DCF and MTX resistance. Individual clones are picked and analyzed for BMP expression, as described above.

It is anticipated that stable cell lines co-expressing other combinations of BMPs which show enhanced activity by transient coexpression will likewise yield greater activity upon stable expression.

EXAMPLE 4

Purification of BMP2/7 and BMP-2/6 Heterodimer

The same purification procedure is used for BMP-2/6 heterodimer and BMP-2/7 heterodimer. Conditioned media from cultures of cell line 2E7E-10 or 12C07 containing recombinantly produced BMP heterodimer 2/7V or 2/6, respectively, can be generated from either adherent or suspension cultures. For small to medium scale generation of coexpressed BMP, adherent cultures are seeded into roller bottles and allowed to grow to confluence in alpha-Minimal Eagles Medium [$\alpha$-MEM, Gibco, Grand Island, N.Y.] containing 10% dialyzed heat-inactivated fetal calf serum [Hazleton, Denver, Pa.]. The media is then switched to a serum-free, albumin free, low protein medium based on a 50:50 mixture of Delbecco's Modified Eagle's medium and Hams F-12 medium, optionally supplemented with 100 micrograms/ml dextran sulfate. Four or five daily harvests are pooled, and used to purify the recombinant protein.

Conditioned medium from roller bottle cultures obtained as described above was thawed slowly at room temperature and pooled. The pH of the pooled medium was adjusted to pH 8.0 using 1 M Tris, pH 8.0. A column was poured containing Matrex Cellufine Sulfate [Amicon] and equilibrated in 50 mM Tris, pH 8.0.

Upon completion of loading of the medium, the column was washed with buffer containing 50 mM Tris, 0.4 M NaCl, pH 8.0 until the absorbance at 280 nm reached baseline. The column was then washed with 50 mM Tris, pH 8.0 to remove NaCl from the buffer. The resin was then washed with 50 mM Tris, 0.2 M NaCl, 4 M Urea, pH 8.0 until a peak had eluted. The column was then washed into 50 mM Tris, pH 8.0 to remove the urea.

The bound BMP-2/7 or BMP-2/6 was then eluted using 50 mM Tris, 0.5 M NaCl, 0.5 M Arginine, pH 8.0. The eluate was collected as a single pool and may be optionally stored frozen prior to further purification. This Cellufine Sulfate eluate was diluted with 14 volumes of 6M urea and the pH of the sample was then adjusted to 6.0. A hydroxyapatite-Ultrogel [IBF] column was poured and equilibrated with 80 mM potassium phosphate, 6M urea, pH 6.0.

After the completion of sample loading, the column was washed with 10 bed volumes of the equilibration buffer. Bound BMP-2/7 or BMP-2/6 heterodiners were eluted with 5 bed volumes of 100 mM potassium phosphate, 6M urea, pH 7.4. This eluate was loaded directly onto a Vydac $C_4$ reverse-phase HPLC column equilibrated in water—0.1% TFA. BMP-2/7 or BMP-2/6 heterodimers were eluted with a gradient of 30–50% acetonitrile in water—0.1% trifluoroacetic acid.

Fractions containing BMPs are identified by SDS-PAGE in the presence or absence of reductant. The identity of the BMPs with respect to the heterodimers vs. homodimers is determined by 2D-PAGE (+/– reductant). Fractions with heterodimers gave bands which reduce to two spots. Bands from homodimer fractions reduce to a single spot for each BMP species.

The BMP-2/6 heterodimer subunits are analyzed on a protein sequenator. BMP-2/6 heterodimers of the following species are present: BMP-6 subunit beginning with amino acid #375 Ser-Ala-Ser-Ser in association with BMP-2 subunit beginning with amino acid #283 Gin-Ala-Lys or #249 Ser-Lev-His, though other less abundant species may be present.

It is contemplated that the same or substantially similar purification techniques may be employed for any recombinant BMP heterodimer of this invention. The hydroxyapatite-Ultrogel column may be unnecessary and that the purification scheme may be modified by loading the Cellufine Sulfate eluate directly onto the $C_4$ reverse-phase HPLC column without use of the former column for BMP2/7 or BMP-2/6 or the other heterodimers of this invention.

EXAMPLE 5

Protein Characterization

Total protein secreted from the co-expressing cell lines is analyzed after labelling with $^{35}$S-methionine or by Western blot analysis using antibodies raised against both BMPs of the heterodimer, e.g., BMP-2 and BMP-7. Together with the alkaline phosphatase assays, the data indicates the presence of the heterodimer and the specific activity. The following specific details are directed towards data collected for the BMP-2/7 and BMP-2/6 heterodimers; however, by application of similar methods to the other heterodimers described herein, similar results are expected.

A. $^{35}$S-Met labelling

Cell lines derived by cotransfection of BMP2Δ-EMC and BMP7Δ-EMC expression vectors were pulsed with $^{35}$S-methionine for 15 minutes, and chased for 6 hours in serum free media in the presence or absence of heparin. Total secreted protein was analyzed under reducing conditions by PAGE and fluorography. The results demonstrate that several cell lines secrete both BMP-2 and BMP-7 protein. There is a good correlation between the amount of alkaline phosphatase activity and the amount of coexpressed protein.

Several cell lines secrete less total BMP-2 and 7 than the BMP-2-only expressing cell line 2EG5, which produces 10 μg/ml BMP-2. Cell line 2E7E-10 (amplified at a level of 0.5 mM MTX) secretes equal proportions of BMP-2 and BMP-7 at about the same overall level of expression as the cell line 2EG5. Cell line 2E7E-10 produces the equivalent of 600 micrograms/ml of BMP-2 homodimer activity in one assay.

Total labelled protein was also analyzed on a two-dimensional non-reducing/reducing gel system to ascertain whether a heterodimer is made. Preliminary results demonstrate the presence of a unique spot in this gel system that is not found in either the BMP-2-only or BMP-7-only cell lines, suggesting the presence of 2/7 heterodimer. The same gel with purified material produced the same results (e.g., two unique spots on the gel) indicative of the presence of the 2/7 heterodimer. The homodimer of BMP2 produced distinct species on this gel system.

In contrast to the recombinant BMP-2/7 purification, BMP-2 homodimers are not detected during the BMP-2/6 preparation; however, significant amounts of BMP-6 homodimers are found. In addition, a significant amount of a −20 amino acid N-terminal truncated form of BMP-6 is found; this could be eliminated by the inclusion of protease inhibitors during cell culture. BMP-2/6 was found to elute two to three fractions later from C4 RP-HPLC than did BMP-2/7.

Amino acid sequencing indicates that the predominant BMP-2/7 heterodimer species comprises a mature BMP-2 subunit [amino acid #283(Gln)-#396(Arg)] and a mature subunit of BMP-7 [#293(Ser)-#431(His)]. BMP-2/6 heterodimer comprises the mature BMP-2 subunit (#283–396) and the mature BMP-6 subunit [#375(Ser)-#513(His)).

B. Immunoprecipitation Coupled to Western Blot Analysis

Conditioned media from a BMP-2-only (2EG5), a BMP-7-only (7MB9), or the 2E7E-10 co-expressing cell line were subjected to immunoprecipitation with either a BMP-2 or BMP-7 antibody (both conventional polyclonal antibodies raised in rabbits), then analyzed on Western blots probed with either an anti-BMP-2 or anti-BMP-7 antibody. The 2/7 heterodimer precipitates and is reactive on Western blots with both the BMP-2 and BMP-7 antibodies, while either BMP by itself reacts with its specific antibody, but not with the reciprocal antibody.

It has been demonstrated using this strategy that a protein in the co-expressing cell line that is precipitated by the anti-BMP-7 antibody W33 [Genetics Institute, Inc, Cambridge, Massachusetts] and reacts on a Western blot with the anti-BMP-2 antibody W12 or W10 [Genetics Institute, Inc.] is not present in the BMP-2 or 7-only expressing cell lines. This experiment indicates that this protein species is the heterodimeric protein. Conversely, precipitation with W12 and probing with W33 yielded similar results.

EXAMPLE 6

Specific Activity of Heterodimers

A. In vitro Assays

The specific activity of the BMP-2/7 or BMP-2/6 heterodimer and the BMP-2 homodimer secreted into growth medium of the stable cell lines 2E7E-10 and 2EG55, and 12C07 and 2EG5, respectively, were estimated as follows.

The amount of BMP protein in conditioned medium was measured by either Western blot analysis or by analyzing protein secreted from $^{35}$S-methionine labelled cells by PAGE and fluorography. The amount of activity produced by the same cell lines on W20 cells using either the alkaline phosphatase assay or osteocalcin-induction assay was then estimated. The specific activity of the BMP was calculated from the ratio of activity to protein secreted into the growth medium.

In one experiment 2E7E-10 and 2EG5 secreted similar amounts of total BMP proteins as determined by PAGE and fluorography. 2E7E-10 produced about 50-fold more alkaline phosphatase inducing activity the 2EG5, suggesting that the specific activity of the heterodimer is about 50-fold higher than the homodimer.

In another experiment the amount of BMP-2 secreted by 2EG5 was about 50% higher than BMP-2/7 secreted by 2E7E-10, however, 2E7E-10 produced about 10-fold more osteocalcin-inducing activity that 2EG5. From several different experiments of this type the specific activity of the BMP-2/7 heterodimer is estimated to be between 5 to 50 fold higher than the BMP-2 homodimer.

Figure 9:
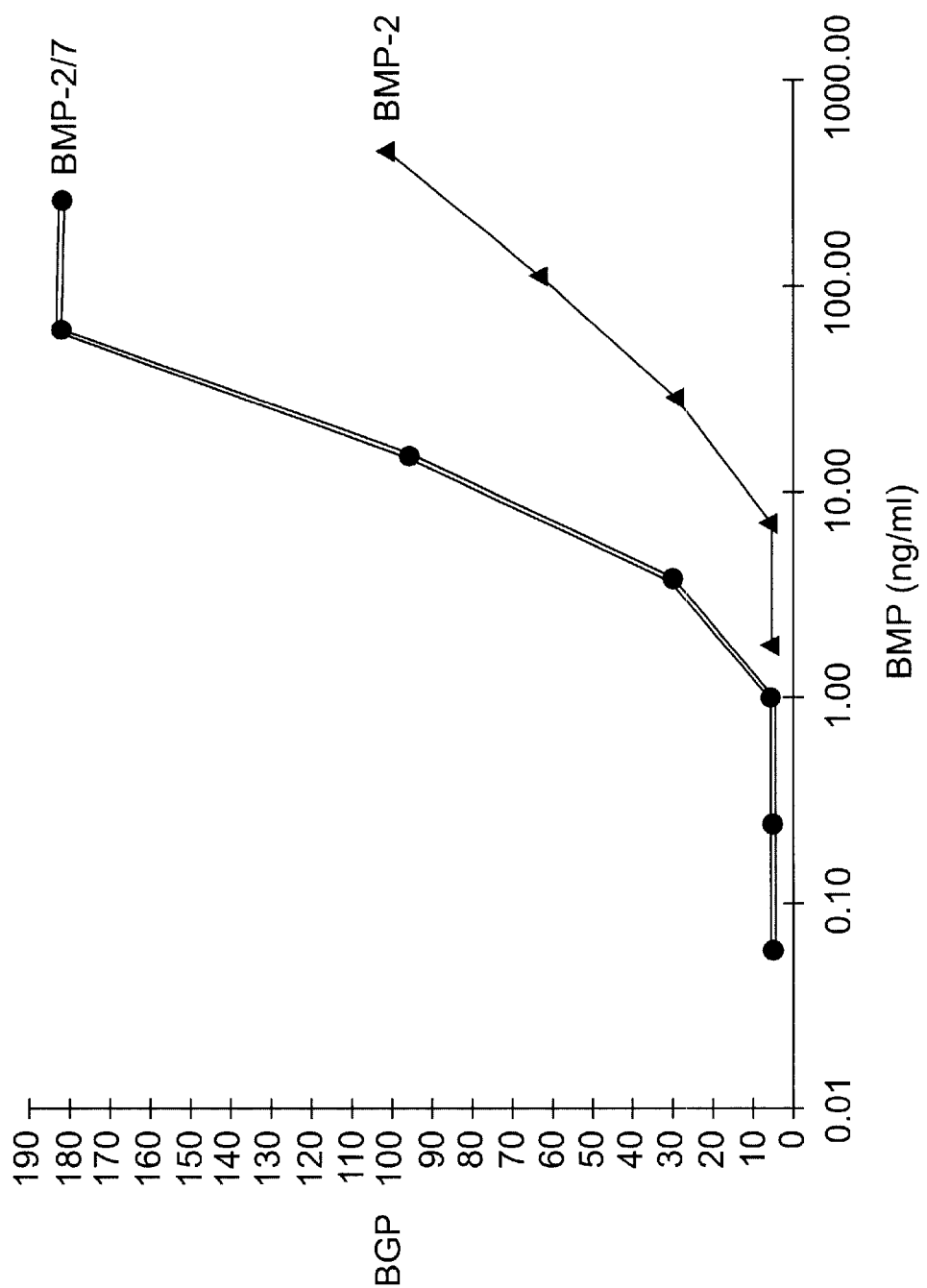
FIG. 9 compares the activity of CHO BMP-2 and CHO BMP-2/7 in the BGP (osteocalcin) assay.

FIGS. 8 and 9 compare the activity of BMP-2 and BMP-2/7 in the W20 alkaline phosphatase and BGP (Bone Gla Protein, osteocalcin) assays. BMP-2/7 has greatly increased specific activity relative to BMP-2 (FIG. 8). From FIG. 8, approximately 1.3 ng/ml of BMP-2/7 was sufficient to induce 50% of the maximal alkaline phosphatase response in W-20 cells. A comparable value for BMP-2 is difficult to calculate, since the alkaline phosphatase response did not maximize, but greater than 30 ng/ml is needed for a half-maximal response. BMP-2/7 thus has a 20 to 30-fold higher specific activity than BMP-2 in the W-20 assay.

As seen in FIG. 9, BMP-2/7 was also a more effective stimulator of BGP (bone gla protein, osteocalcin) production than BMP-2 in this experiment. Treating W-20–17 cells with BMP-2/7 for four days resulted in a maximal BGP response with 62 ng/ml, and 11 ng/ml elicits 50% of the maximal BGP response. In contrast, maximal stimulation of BGP synthesis by BMP-2 was not seen with doses up to 468 ng/ml of protein. The minimal dose of BMP-2/7 needed to elicit a BGP response by W-20–17 cells was 3.9 ng/ml, about seven-fold less than the 29 ng/ml required of BMP-2. These results were consistent with the data obtained in the W-20–17 alkaline phosphatase assays for BMP-2 and BMP-2/7.

Figure 12:
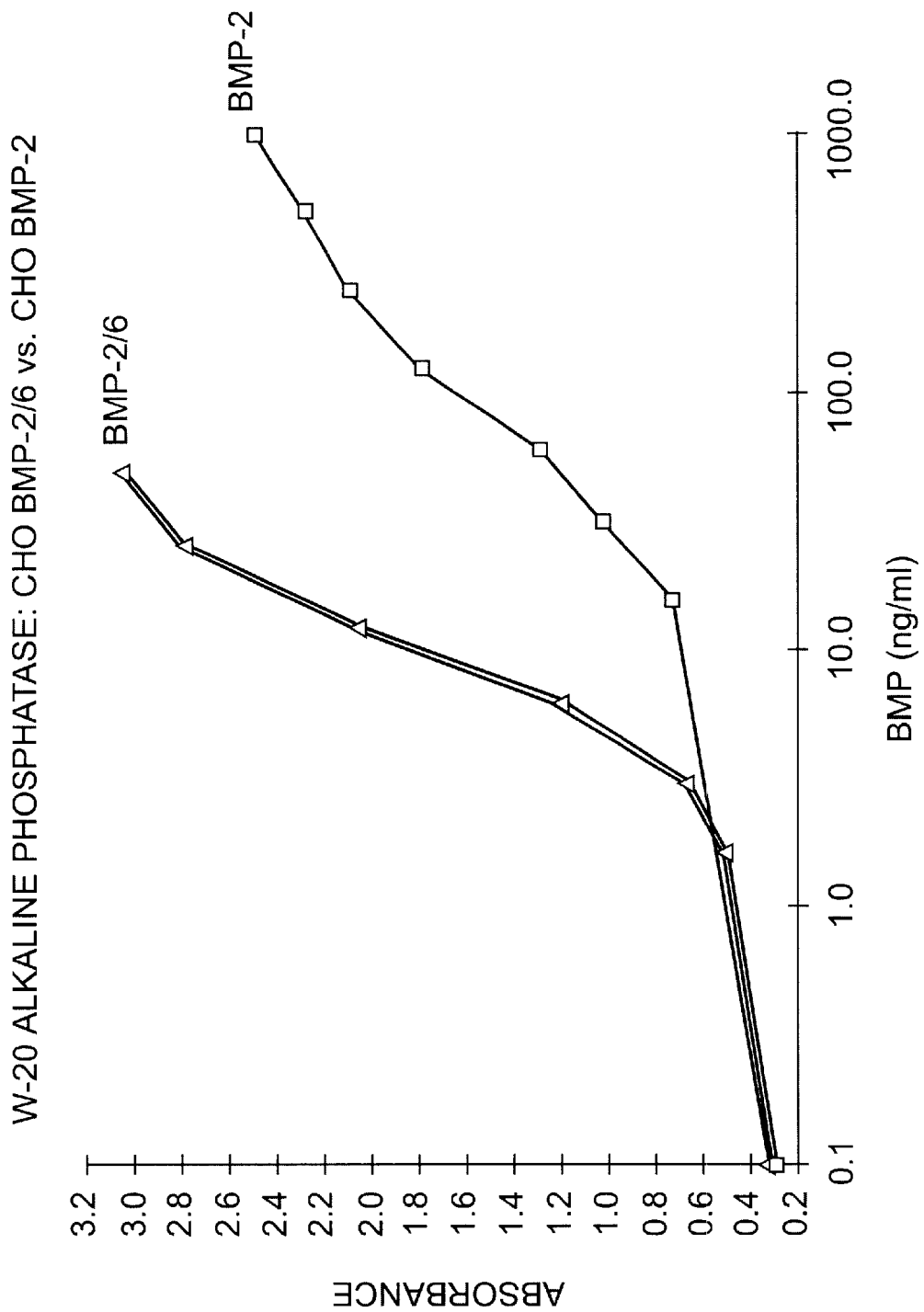
FIG. 12 provides a comparison of BMP-2 and BMP-2/6 in the W-20 assay.

Preliminary analysis indicates that BMP-2/6 has a specific activity in vitro similar to that of BMP-2/7. The potencies of BMP-2 and BMP-2/6 on induction of alkaline phosphatase production in W-20 is compared, as shown in FIG. 12, BMP-2/6 has a higher specific activity than BMP-2 in this assay system. This data is in good agreement with data obtained from the in vivo assay of BMP-2 and BMP-2/6).

B. In Vivo Assay (i) BMP-2/7

The purified BMP-2/7 and BMP-2 were tested in the rat ectopic bone formation assay. A series of different amounts of BMP-2/7 or BMP-2 were implanted in triplicate in rats. After 5 and 10 days, the implants were removed and examined histologically for the presence of bone and cartilage. The histological scores for the amounts of new cartilage and bone formed are summarized in Table A.

TABLE A

|      |     | 5 Day Implants | | 10 Day Implants | |
|------|-----|---------|-------|---------|-------|
|      |     | BMP-2/7 | BMP-2 | BMP-2/7 | BMP-2 |
| 0.04 | C   | ± – ±   | – – – | ± – ±   | – – – |
|      | B   | – – –   | – – – | ± – ±   | – – – |
| 0.02 | C   | ± 1 ±   | – – – | 2 1 2   | – ± ± |
|      | B   | – – –   | – – – | 1 ± 1   | – ± – |
| 1.0  | C   | 1 ± ±   | ± ± ± | 2 2 2   | 1 1 ± |
|      | B   | – – –   | – – – | 2 3 3   | 1 1 ± |
| 5.0  | C   | 2 2 1   | 1 ± 1 | 1 1 2   | 1 2 1 |
|      | B   | ± – 1   | – – – | 4 4 3   | 2 3 2 |
| 25.0 | C   |         |       | ± ± 2   | 2 2 2 |
|      | B   |         |       | 4 4 3   | 3 3 3 |

The amount of BMP-2/7 required to induce cartilage and bone in the rat ectopic assay is lower than that of BMP-2. Histologically, the appearance of cartilage and bone induced by BMP-2/7 and BMP-2 are identical.

(ii) BMP-2/6

The in vivo activity of BMP-2/6 was compared with that of BMP-2 by implantation of various amounts of each BMP for ten days in the rat ectopic bone formation assay. The results of this study (Table B, FIG. 13) indicate that BMP-2/6, similar to BMP-2/7, has increased in vivo activity relative to BMP-2. The specific activities of BMP-2, BMP-6, and BMP-2/6 are compared in the ectopic bone formation assay ten days after the proteins are implanted. The results of these experiments are shown in Table C and FIG. 14. BMP-2/6 is a more potent inducer of bone formation than either BMP-2 or BMP-6. The amount of bone formation observed with BMP-2/6 was comparable to that observed with equivalent doses of BMP-2/7. The appearance of BMP-2/6 implants is quite similar to implants containing BMP-2 or BMP-2/7.

TABLE B

Histological scores of Implants of BMP 2/6 and BMP-2 In rat ectopic assay (10 day implants).

| BMP (µg) | C/B | BMP-2/6 | BMP-2 |
|----------|-----|---------|-------|
| 0.04     | C   | – ± –   | – – – |
|          | B   | – – –   | – – – |
| 0.20     | C   | 1 1 ±   | – – – |
|          | B   | ± ± ±   | – – – |
| 1.0      | C   | 1 3 3   | 1 1 ± |
|          | B   | 1 2 2   | 1 1 ± |
| 5.0      | C   | 2 2 2   | 1 2 2 |
|          | B   | 2 3 3   | 2 2 2 |
| 25.      | C   | 1 1 1   | 2 2 1 |
|          | B   | 3 3 3   | 3 3 3 |

TABLE C

Histological scores of implants of BMP-2, BMP-6, and BMP-2/6 in rat ectopic assay (10 day implants).

| BMP (µg) | C/B | BMP-2 | BMP-6 | BMP-2/6 |
|----------|-----|-------|-------|---------|
| 0.04     | C   | – – – | – – – | – – ±   |
|          | B   | – – – | – – – | – – ±   |
| 0.20     | C   | – – 2 | – – – | 1 2 2   |
|          | B   | – – 1 | – – – | 2 2 2   |
| 1.0      | C   | – ± ± | 2 1 1 | 1 1 1   |
|          | B   | – ± ± | 1 ± ± | 3 3 2   |
| 5.0      | C   | 2 2 1 | 3 1 3 | ± ± 1   |
|          | B   | 1 1 1 | 2 ± 1 | 4 5 4   |
| 25.      | C   | ± ± ± | ± ± ± | ± ± ±   |
|          | B   | 5 4 5 | 4 4 5 | 4 5 3   |

EXAMPLE 7

Expression of DMP Dimer in E. coli

A biologically active, homodimeric BMP-2 was expressed in E. coli using the techniques described in European Patent Application 433,255 with minor modifications. Other-methods disclosed in the above-referenced European patent application may also be employed to produce heterodimers of the present invention from E. coli. Application of these methods to the heterodimers of this invention is anticipated to produce active BMP heterodimeric proteins from E. coli.

A. BMP-2 Expression Vector

An expression plasmid pALBP2–181 (FIG. 7) (SEQ ID NO: 13) was constructed containing the mature portion of the BMP-2 (SEQ ID NO: 14) gene and other sequences which are described in detail below. This plasmid directed the accumulation of 5–10% of the total cell protein as BMP-2,in an E. coli host strain, GI724, described below.

Plasmid pALBP2–781 contains the following principal features. Nucleotides 1–2060 contain DNA sequences originating from the plasmid pUC-18 [Norrander et al, Gene, 26:101–106.(1983)] including sequences containing the gene for β-lactamase which confers resistance to the antibiotic ampicillin in host E. coli strains, and a colEl-derived origin of replication. Nucleotides 2061–2221 contain DNA sequences for the major leftward promoter (pL) of bacteriophage λ [Sanger et al, J. Mol. Biol., 162:729–773 (1982)], including three operator sequences, $O_L1$, $O_L2$ and $O_L3$. The operators are the binding sites for λcI repressor protein, intracellular levels of which control the amount of transcription initiation from pL. Nucleotides 2222–2723 contain a strong ribosome binding sequence included on a sequence derived from nucleotides 35566 to 35472 and 38137 to 38361 from bacteriophage lambda as described in Sanger et al, J. Mol. Biol., 162:729–773 (1982). Nucleotides 2724–3133 contain a DNA sequence encoding mature BMP-2 protein with an additional 62 nucleotides of 3'-untranslated sequence.

Nucleotides 3134–3149 provide a "Linker" DNA sequence containing restriction endonuclease sites. Nucleotides 3150–3218 provide a transcription termination sequence based on that of the E. coli asnA gene [Takagi et al, Nucl. Acids Res., 13:2063–2074 (1985)]. Nucleotides 3219–3623 are DNA sequences derived from pUC-18.

As described below, when cultured under the appropriate conditions in a suitable E. coli host strain, pALBP2–781 can direct the production of high levels (approximately 10% of the total cellular protein) of BMP-2 protein.

pALBP2–781 was transformed into the E. coli host strain G1724 (F, lacI$^q$, lacP$^{L8}$, ampC::λcI$^+$) by the procedure of Dagert and Ehrlich, Gene, 6:23 (1979). (The untransformed host strain E. coli GI724 was deposited with the American Type Culture Collection, 12301 Parklawn Drive, Rockville, Md. on Jan. 31, 1991 under ATCC No. 55151 for patent purposes pursuant to applicable laws and regulations.] Transformants were-selected on 1.5% w/v agar plates containing IMC medium, which is composed of M9 medium [Miller, "Experiments in Molecular Genetics", Cold Spring Harbor Laboratory, New York (1972)] supplemented with 0.5%. w/v glucose, 0.2% w/v casamino acids and 100 µg/ml ampicillin.

GI724 contains a copy of the wild-type XcI repressor gene stably integrated into the chromosome at the ampC locus, where it has been placed under the transcriptional control of Salmonella typhimurium trp promoter/operator sequences. In GI724, XcI protein is made only during growth in tryptophan-free media, such as minimal media or a minimal medium supplemented with casamino acids such as IMC, described above. Addition of tryptophan to a culture of GI724 will repress the trp promoter and turn off synthesis of λcI, gradually causing the induction of transcription from pL promoters if they are present in the cell.

GI724 transformed with pALBP2–781 was grown at 37° C. to an $A_{550}$ of 0.5 (Absorbence at 550 nm) in IMC medium. Tryptophan was added to a final concentration of 100 µg/ml and the culture incubated for a further 4 hours. During this time BMP-2 protein accumulated to approximately 10% of the total cell protein, all in the "inclusion body" fraction.

BMP-2 is recovered in a non-soluble, monomeric form as follows. Cell disruption and recovery is performed at 4° C. Approximately 9 g of the wet fermented E. coli GI724/pALBP2–781 cells are suspended in 30 mL of 0.1 M Tris/HCl, 10 mM EDTA, 1 mM phenyl methyl sulphonyl fluoride (PMSF), pH 8.3 (disruption buffer). The cells are passed four times through a cell disrupter and the volume is brought to 100 mL with the disruption buffer. The suspension is centrifuged for 20 min. (15,000×g). The pellet obtained is suspended in 50 mL disruption buffer containing 1 M NaCl and centrifuged for 10 min. as above. The pellet is suspended in 50 mL disruption buffer containing 1% Triton X-100 (Pierce) and again centrifuged for 10 min. as above. The washed pellet is then suspended in 25 mL of 20 mM Tris/HCl, 1 mM EDTA, 1 mM PMSF, 1% DTT, pH 8.3 and homogenized in a glass homogenizer. The resulting suspension contains crude monomeric BMP-2 in a non-soluble form.

Ten mL of the BMP-2 suspension, obtained as described above, are acidified with 10% acetic acid to pH 2.5 and centrifuged in an Eppendorf centrifuge for 10 min. at room temperature. The supernatant is chromatographed. Chromatography was performed on a Sephacryl S-100 HR column (Pharmacia, 2.6×83 cm) in 1% acetic acid at a flow rate of 1.4 mL/minute. Fractions containing monomeric, BMP-2 are pooled. This material is used to generate biologically active, homodimer BMP-2.

Biologically active, homodimeric BMP-2 can be generated from the monomeric BMP-2 obtained following solubilization and purification, described above, as follows.

0.1, 0.5 or 2.5 mg of the BMP-2 is dissolved at a concentration of 20, 100 or 500 µg/mL, respectively, in 50 mM Tris/HCl, pH 8.0, 1 M NaCl, 5 mM EDTA, 2 mM reduced glutathione, 1 mM oxidized glutathione and 33 mM CHAPS [Calbiochem]. After 4 days at 4° C. or 23° C., the mixture is diluted 5 to 10 fold with 0.1% TFA.

Purification of biologically active BMP-2 is achieved by subjecting the diluted mixture to reverse phase HPLC on a a Vydac C4 214TP54 column (25×0.46 cm) [The NEST Group, USA] at a flow rate of 1 ml/minute. Buffer A is 0.1% TFA. Buffer B is 90% acetonitrile, and 0.1% TFA. The linear gradient was 0 to 5 minutes at 20% Buffer B; 5 to 10 minutes at 20 to 30% Buffer B; 10 to 40 minutes at 30 to 60% Buffer B; and 40 to 50 minutes at 60 to 100% Buffer B. Homodimeric BMP-2 is eluted and collected from the HPLC column.

The HPLC fractions are lyophilized to dryness, redissolved in sample buffer (1.5 M Tris-HCl, pH 8.45, 12% glycerol, 4% SDS, 0.0075% Serva Blue G, 0.0025% Phenol Red, with or without 100 mM dithiothreitol) and heated for five minutes at 95° C. The running buffer is 100 mM Tris, 100 mM tricine (16% tricine gel) [Novex], 0.1% SDS at pH 8.3. The SDS-PAGE gel is run at 125 volts for 2.5 hours.

The gel is stained for one hour with 200 ml of 0.5% Coomassie Brilliant Blue R-250, 25% isopropanol, 10% acetic acid, heated to 60° C. The gel is then destained with 10% acetic acid, 10% isopropanol until the background is clear.

The reduced material ran at approximately 13 kD; the non-reduced material ran at approximately 30 kD, which is indicative of the BMP-2 dimer. This material was later active in the W20.assay of Example 8.

B. BMP-7 Expression Vector

For high level expression of BMP-7 a plasmid pAlBMP7-981 was constructed. pAlBMP7-981 is identical to plasmid pALBP2-781 with two exceptions: the BMP-2 gene (residues 2724–3133 of pALBP2–781) is replaced by the mature portion of the BMP-7 gene, deleted for sequenced encoding the first seven residues of the mature BMP-7 protein sequence:

| | | | | |
|---|---|---|---|---|
| ATGTCTCATAATC | GTTCTAAAAC | TCCAAAAAAT | CAAGAAGCTC | TGCGTATGGC |
| CAACGTGGCA | GAGAACAGCA | GCAGCGACCA | GAGGCAGGCC | TGTAAGAAGC |
| ACGAGCTGTA | TGTCAGCTTC | CGAGACCTGG | GCTGGCAGGA | CTGGATCATC |
| GCGCCTGAAG | GCTACGCCGC | CTACTACTGT | GAGGGGGAGT | GTGCCTTCCC |
| TCTGAACTCC | TACATGAACG | CCACCAACCA | CGCCATCGTG | CAGACGCTGG |
| TCCACTTCAT | CAACCCGGAA | ACGGTGCCCA | AGCCCTGCTG | TGCGCCCACG |
| CAGCTCAATG | CCATCTCCGT | CCTCTACTTC | GATGACAGCT | CCAACGTCAT |
| CCTGAAGAAA | TACAGAAACA | TGGTGGTCCG | GGCCTGTGGC | TGCCACTAGC |
| TCCTCCGAGA | ATTCAGACCC | TTTGGGGCCA | AGTTTTTCTG | GATCCT | and the ribosome binding site found between residues 2707 and 2723 in pALBP2–781 is replaced by a different ribosome binding site, based on that found preceding the T7 phage gene 10, of sequence 5'-CAAGAAGGAGATATACAT-3'. The host strain and growth conditions used for the production of BMP-7 were as described for BMP-2.

C. BMP-3 Expression Vector

For high level expression of BMP-3 a plasmid pALB3-782 was constructed. This plasmid is identical to plasmid pALBP2-781, except that the BMP-2 gene (residues 2724–3133 of pALBP2-781) is replaced by a gene encoding a form of mature BMP-3. The sequence of this BMP-3 gene is:

| | | | | |
|---|---|---|---|---|
| ATGCGTAAAC | AATGGATTGA | ACCACGTAAC | TGTGCTCGTC | GTTATCTGAA |
| AGTAGACTTT | GCAGATATTG | GCTGGAGTGA | ATGGATTATC | TCCCCCAAGT |
| CCTTTGATGC | CTATTATTGC | TCTGGAGCAT | GCCAGTTCCC | CATGCCAAAG |
| TCTTTGAAGC | CATCAAATCA | TGCTACCATC | CAGAGTATAG | TGAGAGCTGT |
| GGGGGTCGTT | CCTGGGATTC | CTGAGCCTTG | CTGTGTACCA | GAAAAGATGT |
| CCTCACTCAG | TATTTTATTC | TTTGATGAAA | ATAAGAATGT | AGTGCTTAAA |
| GTATACCCTA | ACATGACAGT | AGAGTCTTGC | GCTTGCAGAT | AACCTGGCAA |
| AGAACTCATT | TGAATGCTTA | ATTCAAT | | |

The host strain and growth conditions used for the production of BMP-3 were as described for BMP-2.

D. Expression of a BMP-2/7 Heterodimer in *E. coli*

Denatured and purified *E. coli* BMP-2 and BMP-7 monomers were isolated from *E. coli* inclusion body pellets by acidification and gel filtration as previously as previously described above. 125 ug of each BMP in 1% acetic acid were mixed and taken to dryness in a speed vac. The material was resuspended in 2.5 ml 50 mM Tris, 1.0 NaCl, 5 mM EDTA, 33 mM CHAPS, 2 mM glutathione (reduced), 1 mM glutathione (oxidized), pH 8.0. The sample was incubated at 23 C for one week.

The BMP-2/7 heterodimer was isolated by HPLC on a 25×0.46 cm Vydac C4 column. The sample was centrifuged :in a microfuge for 5 minutes, and the supernatant was diluted with 22.5 ml 0.1% TFA.

| | |
|---|---|
| A buffer: | 0.1% TFA |
| B buffer: | 0.1% TFA, 95% acetonitrile |
| 1.0 ml/minute | |
| 0–5' | 20% B |
| 5–10' | 20–30% B |
| 10–90' | 30–50% B |
| 90–100' | 50–100% B |

By SDS-PAGE analysis, the BMP-2/7 heterodimer eluted at about 23'.

Figure 10:
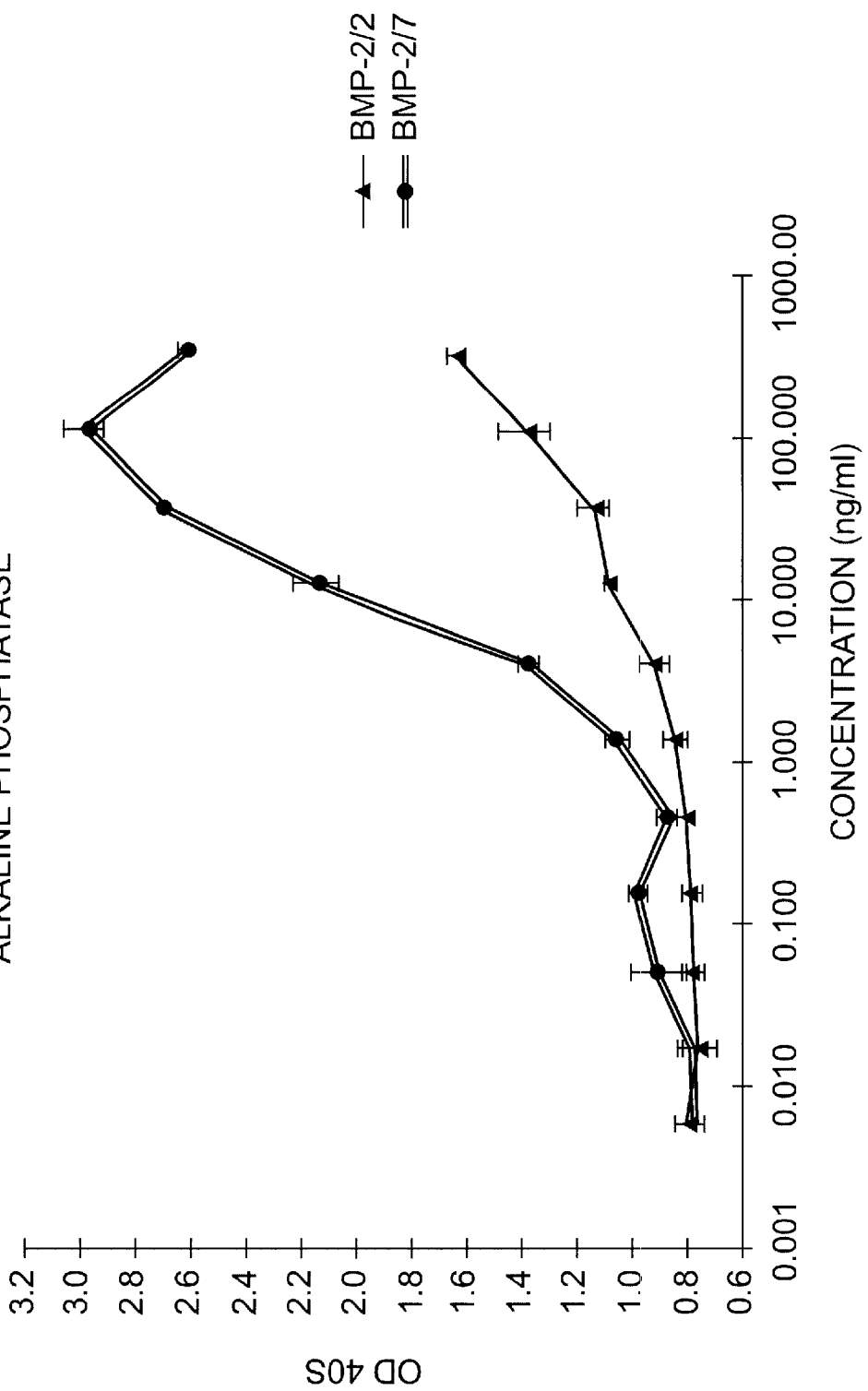
FIG. 10 provides a comparison of the W-20 activity of E. coli produced BMP-2 and BMP-2/7 heterodimer.

FIG. 10 is a comparison of the W-20 activity of *E. coli* BMP-2 and BMP-2/7 heterodimer, indicating greater activity of the heterodimer.

F. Expression of BMP-2/3 Heterodimer in *E. coli*

BMP-2 and BMP-3 monomers were isolated as follows: to 1.0 g of frozen harvested cells expressing either BMP-2 or BMP-3 was added 3.3 ml of 100 mM Tris, 10 mM EDTA, pH 8.3. The cells were resuspended by vortexing vigorously. 33 ul of 100 mM PMSF in isopropanol was added and the cells lysed by one pass through a French pressure cell. The lysate was centrifuged in a microfuge for 20 minutes at 4 C. The supernatant was discarded. The inclusion body pellet was taken up in 8.0 M quanidine hydrochloride, 0.25 M OTT, 0.5 M Tris, 5 mM EDTA, pH 8.5, and heated at 37 C for one hour.

The reduced and denatured BMP monomers were isolated by HPLC on a Supelco C4 guard column as follows:

| | |
|---|---|
| A buffer: | 0.1% TFA |
| B buffer: | 0.1% TFA, 95% acetonitrile |

-continued

| | |
|---|---|
| 1.0 ml/minute | |
| 0–5' | 1% B |
| 5–40' | 1–70% B |
| 40–45' | 70–100% B |

Monomeric BMP eluted at 28–30'. Protein concentration was estimated by A280 and the appropriate extinction coefficient.

10 ug of BMP-2 and BMP-3 were combined and taken to dryness in a speed vac. To this was added 50 ul of 50 mM Tris, 1.0 M NaCl, 5 mM EDTA, 33 mM CHAPS, 2 mM reduced glutathione, 1 mM oxidized glutathione, pH 8.5. The sample was incubated at 23 for 3 days. The sample was analyzed by SDS-PAGE on a 16% tricine gel under reducing and nonreducing conditions. The BMP-2/3 heterodimer migrated at about 35 kd nonreduced, and reduced to BMP-2 monomer at about 13 kd and BMP-3 monomer at about 21 kd.

BMP-2/3 heterodimer produced in *E. coli* is tested for in vivo activity. (20 µg) at (ten days) is utilized to compare the in vivo activity of BMP-2/3 to BMP-2. BMP-2/3 implants showed no cartilage or bone forming activity, while the BMP-2 control implants showed the predicted amounts of bone and cartilage formation. The in vivo data obtained with BMP-2/3 is consistent with the in vitro data from the W-20 assay.

EXAMPLE 8

W-20 Bioassays

A. Description of W-20 cells

Use of the W-20 bone marrow stromal cells as an indicator cell line is based upon the conversion of these cells to osteoblast-like cells after treatment with BMP-2 (R. S. Thies et al, "Bone Morphogenetic Protein alters W-20 stromal cell differentiation in vitro", *Journal of Bone and Mineral Research*, 5(2):305 (1990); and R. S. Thies et al, "Recombinant Human Bone Morphogenetic Protein 2 Induces Osteoblastic Differentiation in W-20-17 Stromal Cells", *Endocrinology*, in press (1992)]. Specifically, W-20 cells are a clonal bone marrow stromal cell line derived from adult mice by researchers in the laboratory of Dr. D. Nathan, Children's Hospital, Boston, Mass. BMP-2 treatment of W-20 cells results in (1) increased alkaline phosphatase production, (2) induction of PTH stimulated cAMP, and (3) induction of osteocalcin synthesis by the cells. While (1) and (2) represent characteristics associated with the osteoblast phenotype, the ability to synthesize osteocalcin is a phenotypic property only displayed by mature osteoblasts. Furthermore, to date we have observed conversion of W-20 stromal cells to osteoblast-like cells only upon treatment with BMPs. In this manner, the in vitro activities displayed by BMP treated W-20 cells correlate with the in vivo bone forming activity known for BMPS.

Below two in vitro assays useful in comparison of BMP activities of novel osteoinductive molecules are described.

B. W-20 Alkaline Phosphatase Assay Protocol

W-20 cells are plated into 96 well tissue culture plates at a density of 10,000 cells per well in 200 µl of media (DME with 10% heat inactivated fetal calf serum, 2 mM glutamine and 100 U/ml+100 µg/ml streptomycin. The cells are allowed to attach overnight in a 95% air, 5% $CO_2$ incubator at 37° C.

The 200 µl of media is removed from each well with a multichannel pipettor and replaced with an equal volume of test sample delivered in DME with 10% heat inactivated fetal calf serum, 2 mM glutamine and 1% penicillin-streptomycin. Test substances are assayed in triplicate.

The test samples and standards are allowed a 24 hour incubation period with the W-20 indicator cells. After the 24 hours, plates are removed from the 37° C. incubator and the test media are removed from the cells.

The W-20 cell layers are washed 3 times with 200 µl per well of calcium/magnesium free phosphate buffered saline and these washes are discarded.

50 µl of glass distilled water is added to each well and the assay plates are then placed on a dry ice/ethanol bath for quick freezing. Once frozen, the assay plates are removed from the dry ice/ethanol bath and thawed at 37° C. This step is repeated 2 more times for a total of 3 freeze-thaw procedures. Once complete, the membrane bound alkaline phosphatase is available for measurement.

50 µl of assay mix (50 mM glycine, 0.05% Triton X-100, 4 mM $MgCl_2$, 5 mM p-nitrophenol phosphate, pH =10.3) is added to each assay well and the assay plates are then incubated for 30 minutes at 37° C. in a shaking waterbath at 60 oscillations per minute.

At the end of the 30 minute incubation, the reaction is stopped by adding 100 µl of 0.2 N NaOH to each well and placing the assay plates on ice.

The spectrophotometric absorbance for each well is read at a wavelength of 405 nanometers. These values are then compared to known standards to give an estimate of the alkaline phosphatase activity in each sample. For example, using known amounts of p-nitrophenol phosphate, absorbance values are generated. This is shown in Table I.

TABLE I

Absorbance Values for Known Standards of P-Nitrophenol Phosphate

| P-nitrophenol phosphate umoles | Mean absorbance (405 nm) |
| --- | --- |
| 0.000 | 0 |
| 0.006 | 0.261 +/− .024 |
| 0.012 | 0.521 +/− .031 |
| 0.018 | 0.797 +/− .063 |
| 0.024 | 1.074 +/− .061 |
| 0.030 | 1.305 +/− .083 |

Absorbance values for known amounts of BMP-2 can be determined and converted to µmoles of p-nitrophenol phosphate cleaved per unit time as shown in Table II.

TABLE II

Alkaline Phosphatase Values for W-20 Cells Treating with BMP-2

| BMP-2 concentration ng/ml | Absorbance Reading 405 nmeters | umoles substrate per hour |
| --- | --- | --- |
| 0 | 0.645 | 0.024 |
| 1.56 | 0.696 | 0.026 |
| 3.12 | 0.765 | 0.029 |
| 6.25 | 0.923 | 0.036 |
| 12.50 | 1.121 | 0.044 |
| 25.0 | 1.457 | 0.058 |
| 50.0 | 1.662 | 0.067 |
| 100.0 | 1.977 | 0.080 |

These values are then used to compare the activities of known amounts of BMP heterodimers to BMP-2 homodimer.

C. Osteocalcin RIA Protocol

W-20 cells are plated at $10^6$ cells per well in 24 well multiwell tissue culture dishes in 2 mls of DME containing 10% heat inactivated fetal calf serum, 2 mM glutamine. The cells are allowed to attach overnight in an atmosphere of 95% air 5% $CO_2$ at 37° C.

The next day the medium is changed to DME containing 10% fetal calf serum, 2 mM glutamine and the test substance in a total volume of 2 ml. Each test substance is administered to triplicate wells. The test substances are incubated with the W-20 cells for a total of 96 hours with replacement at 48 hours by the same test medias.

At the end of 96 hours, 50 µl of the test media is removed from each well and assayed for osteocalcin production using a radioimmunoassay for mouse osteocalcin. The details of the assay are described in the kit manufactured by Biomedical Technologies Inc., 378 Page Street, Stoughton, Mass. 02072. Reagents for the assay are found as product numbers BT-431 (mouse osteocalcin standard), BT-432 (Goat anti-mouse Osteocalcin), BT-431R (iodinated mouse osteocalcin), BT-415 (normal goat serum) and BT-414 (donkey anti goat IgG). The RIA for osteocalcin synthesized by W-20 cells in response to BMP treatment is carried out as described in the protocol provided by the manufacturer.

The values obtained for the test samples are compared to values for known standards of mouse osteocalcin and to the amount of osteocalcin produced by W-20 cells in response to challenge with known amounts of BMP-2. The values for BMP-2 induced osteocalcin synthesis by W-20 cells is shown in Table III.

TABLE III

Osteocalcin Synthesis by W-20 Cells

| BMP-2 Concentration ng/ml | Osteocalcin Synthesis ng/well |
|---|---|
| 0 | 0.8 |
| 2 | 0.9 |
| 4 | 0.8 |
| 8 | 2.2 |
| 16 | 2.7 |
| 31 | 3.2 |
| 62 | 5.1 |
| 125 | 6.5 |
| 250 | 8.2 |
| 500 | 9.4 |
| 1000 | 10.0 |

EXAMPLE 9

Rosen Modified Sampath-Reddi Assay

A modified version of the rat bone formation assay described in Sampath and Reddi, *Proc. Natl. Acad. Sci. USA*, 80:6591–6595 (1983) is used to evaluate bone and/or cartilage activity of BMP proteins. This modified assay is herein called the Rosen-modified Sampath-Reddi assay. The ethanol precipitation step of the Sampath-Reddi procedure is replaced by dialyzing (if the composition is a solution) or diafiltering (if the composition is a suspension) the fraction to be assayed against water. The solution or suspension is then redissolved in 0.1% TFA, and the resulting solution added to 20 mg of rat matrix. A mock rat matrix sample not treated with the protein serves as a control. This material is frozen and lyophilized and the resulting powder enclosed in #5 gelatin capsules. The capsules are implanted subcutaneously in the abdominal thoracic area of 21–49 ay old male Long Evans rats. The implants are removed after 7–14 days. Half of each implant is used for alkaline phosphatase analysis [see, A. H. Reddi et al, *Proc. Natl. Acad. Sci.*, 69:1601 (1972)].

The other half of each implant is fixed and processed for histological analysis. 1 µm glycolmethacrylate sections are stained with Von Kossa and acid fuschin to score the amount of induced bone and cartilage formation present in each implant. The terms +1 through +5 represent the area of each histological section of an implant occupied by new bone and/or cartilage cells and matrix. A score of +5 indicates that greater than 50% of the implant is new bone and/or cartilage produced as a direct result of protein in the implant. A score of +4, +3, +2, and +1 would indicate that greater than 40%, 30%, 20% and 10% respectively of the implant contains new cartilage and/or bone.

The heterodimeric BMP proteins of this invention may be assessed for activity on this assay.

Numerous modifications and variations in practice of this invention are expected to occur to those skilled in the art. Such modifications and variations are encompassed within the following claims.

What is claimed is:

1. A method for producing a heterodimeric protein having bone stimulating activity comprising culturing under suitable conditions to produce said protein a selected host cell containing a first DNA sequence encoding a BMP selected from the group consisting of BMP-2 and BMP-4 and a second DNA sequence encoding BMP-8, said sequences each being under the control of a suitable regulatory sequence capable of directing co-expression of said proteins, and isolating said heterodimeric protein from the culture medium.

2. The method according to claim 1 wherein said first DNA is present on a first vector transfected into said host cell and said second DNA is present on a second vector transfected into said host cell.

3. The method according to claim 1 wherein both said BMPs are integrated into a chromosome of said host cell.

4. The method according to claim 1 wherein both BMPs are present on a single vector.

5. The method according to claim 2 wherein more than a single copy of the gene encoding each said BMP is present on each vector.

6. The method according to claim 1 wherein said host cell is a hybrid cell prepared by culturing two fused selected, stable host cells, each host cell transfected with a DNA sequence encoding said selected first or second BMP, said sequences under the control of a suitable regulatory sequence capable of directing expression of each protein, and isolating said heterodimer protein from the culture medium.

7. The method according to claim 1 wherein said host cell is a mammalian cell.

8. The method according to claim 1 wherein said host cell is an insect cell.

9. The method according to claim 1 wherein said host cell is a yeast cell.

10. A method for producing a heterodimeric protein having bone stimulating activity in a bacterial cell comprising culturing a selected host cell containing a first DNA sequence encoding a BMP selected from the group consisting of BMP-2 and BMP-4 under the control of a suitable regulatory sequence capable of directing expression of the protein under conditions suitable for the formation of a soluble, monomeric protein; isolating said monomeric protein from inclusion bodies and/or said culture medium; culturing a selected host cell containing a second DNA sequence encoding BMP-8 under the control of a suitable regulatory sequence capable of directing expression of the protein or protein fragment under said conditions to form a second soluble, monomeric protein; isolating said monomeric protein from inclusion bodies and/or said culture medium; and mixing said soluble monomeric proteins under conditions permitting the formation of dimeric proteins associated by at least one covalent disulfide bond; and isolating from the mixture a heterodimeric protein.

11. The method according to claim 10 wherein said host cell is *E. coli*.

12. The method according to claim 10 wherein said conditions comprise treating said protein with a solubilizing agent.

13. A cell line comprising a nucleotide sequence encoding a first BMP selected from the group consisting of BMP-2 and BMP-4 under control of a suitable expression regulatory system and a nucleotide sequence encoding a BMP-8 under control of a suitable expression regulatory system, said regulatory systems capable of directing the co-expression of said BMPs and the formation of heterodimeric protein.

14. The cell line according to claim 13 wherein said nucleotide sequences encoding BMP proteins are present in a single DNA molecule.

15. The cell line according to claim 13 wherein said nucleotide sequence encoding said first BMP is present on a first DNA molecule and said nucleotide sequence encoding said second BMP is present on a second DNA molecule.

* * * * *

UNITED STATES PATENT AND TRADEMARK OFFICE
CERTIFICATE OF CORRECTION

PATENT NO. : 6,593,109 B1
DATED : July 15, 2003
INVENTOR(S) : David Israel and Neil M. Wolfman It is certified that error appears in the above-identified patent and that said Letters Patent is hereby corrected as shown below:

<u>Title page,</u>
Item [57], ABSTRACT,
Line 1, "to a methods" should read -- to methods --.

Signed and Sealed this

Ninth Day of September, 2003

JAMES E. ROGAN
*Director of the United States Patent and Trademark Office*